(12) United States Patent
Spitler et al.

(10) Patent No.: US 7,618,442 B2
(45) Date of Patent: Nov. 17, 2009

(54) IMPLANT ASSEMBLY AND METHOD FOR USE IN AN INTERNAL STRUCTURE STABILIZATION SYSTEM

(75) Inventors: James Spitler, Frisco, TX (US); Scott Schorer, Longmont, CO (US); Dennis Colleran, Frisco, TX (US)

(73) Assignee: Theken Spine, LLC, Akron, OH (US)

( * ) Notice: Subject to any disclaimer, the term of this patent is extended or adjusted under 35 U.S.C. 154(b) by 236 days.

(21) Appl. No.: 10/990,272

(22) Filed: Nov. 16, 2004

(65) Prior Publication Data
US 2006/0036244 A1  Feb. 16, 2006

Related U.S. Application Data

(63) Continuation-in-part of application No. 10/690,211, filed on Oct. 21, 2003, now Pat. No. 7,588,588.

(51) Int. Cl.
*A61B 17/58* (2006.01)
(52) U.S. Cl. .............. 606/266; 606/261; 606/258; 606/270; 606/279; 606/86 A
(58) Field of Classification Search ............ 606/61, 606/71–72, 86 A, 916, 914
See application file for complete search history.

(56) References Cited

U.S. PATENT DOCUMENTS

| | | | |
|---|---|---|---|
| 1,522,927 A * | 1/1925 | Wickstrom et al. ........... 81/453 |
| 2,248,054 A | 7/1941 | Becker |
| 2,302,691 A | 11/1942 | Green |
| 2,329,398 A | 9/1943 | Duffy |
| 2,952,285 A | 9/1960 | Roosli |
| 3,842,825 A | 10/1974 | Wagner |
| 3,989,284 A | 11/1976 | Blose |
| 4,140,111 A | 2/1979 | Morrill |
| 4,361,141 A | 11/1982 | Tanner |
| 4,433,677 A | 2/1984 | Ulrich |
| 4,719,905 A | 1/1988 | Steffee |
| 4,771,767 A | 9/1988 | Steffee |
| 4,790,297 A | 12/1988 | Luque |
| 4,827,918 A | 5/1989 | Olerud |
| 4,917,409 A | 4/1990 | Reeves |

(Continued)

FOREIGN PATENT DOCUMENTS

DE  8910080  12/1989

(Continued)

OTHER PUBLICATIONS

U.S. Appl. No. 10/805,967, Colleran et al.

(Continued)

*Primary Examiner*—Eduardo C Robert
*Assistant Examiner*—Mary Hoffman
(74) *Attorney, Agent, or Firm*—Middleton Reutlinger; Robert H. Eichenberger

(57) ABSTRACT

An assembly for use in spinal stabilization procedures having first and second bone anchor assemblies. Embodiments of the first bone anchor assembly may include an anchor, a poly-axial head, including a cavity, mated with the anchor such that the anchor is movable relative to the poly-axial head. Embodiments of the second bone anchor assembly may include an anchor, a poly-axial head mated with the second anchor such that the anchor is movable relative to the poly-axial head, a slide ring rotatably mated in the second poly-axial head, and a connector slideably mated in the slide ring along a distal end, and having a proximal end having an enlarged portion. The connector may be movable from a first position axially inline with the second bone anchor to a second position wherein the enlarged portion of the connector rests in the cavity of the first poly-axial head.

18 Claims, 43 Drawing Sheets

U.S. PATENT DOCUMENTS

| | | | |
|---|---|---|---|
| 4,950,269 A | 8/1990 | Gaines, Jr. | |
| 5,042,982 A | 8/1991 | Harms | |
| 5,047,029 A * | 9/1991 | Aebi et al. | 606/61 |
| 5,102,412 A | 4/1992 | Rogozinski | |
| 5,116,337 A | 5/1992 | Johnson | |
| 5,120,171 A | 6/1992 | Lasner | |
| 5,171,279 A | 12/1992 | Mathews | |
| 5,176,680 A | 1/1993 | Vignaud et al. | |
| 5,196,014 A * | 3/1993 | Lin | 606/61 |
| 5,196,015 A | 3/1993 | Neubardt | |
| 5,207,678 A | 5/1993 | Harms | |
| 5,258,016 A | 11/1993 | DiPoto et al. | |
| 5,261,913 A | 11/1993 | Marnay | |
| 5,304,179 A | 4/1994 | Wagner | |
| 5,312,438 A | 5/1994 | Johnson | |
| 5,330,472 A | 7/1994 | Metz-Stavenhagen | |
| 5,360,431 A * | 11/1994 | Puno et al. | 606/61 |
| 5,375,823 A | 12/1994 | Navas | |
| 5,387,212 A * | 2/1995 | Yuan et al. | 606/61 |
| 5,387,213 A | 2/1995 | Breard | |
| 5,409,488 A | 4/1995 | Ulrich | |
| 5,425,732 A | 6/1995 | Ulrich | |
| 5,458,608 A | 10/1995 | Wortrich | |
| 5,466,237 A | 11/1995 | Byrd, III et al. | |
| 5,468,241 A | 11/1995 | Metz-Stavenhagen | |
| 5,474,555 A | 12/1995 | Puno et al. | |
| 5,480,440 A | 1/1996 | Kambin | |
| 5,486,174 A | 1/1996 | Fournet-Fayard | |
| 5,496,321 A | 3/1996 | Puno | |
| 5,507,211 A | 4/1996 | Wagner | |
| 5,520,689 A * | 5/1996 | Schlapfer et al. | 606/61 |
| 5,526,812 A | 6/1996 | Dumoulin et al. | |
| 5,536,268 A | 7/1996 | Griss | |
| 5,540,688 A | 7/1996 | Navas | |
| 5,569,246 A | 10/1996 | Ojima | |
| 5,571,102 A | 11/1996 | Cavagna | |
| 5,605,457 A | 2/1997 | Bailey et al. | |
| 5,605,458 A | 2/1997 | Bailey et al. | |
| 5,607,304 A | 3/1997 | Bailey et al. | |
| 5,607,425 A | 3/1997 | Rogozinski | |
| 5,628,740 A | 5/1997 | Mullane | |
| 5,643,260 A | 7/1997 | Doherty | |
| 5,662,658 A | 9/1997 | Wenstrom | |
| 5,667,513 A | 9/1997 | Torrie et al. | |
| 5,672,176 A | 9/1997 | Biedermann et al. | |
| 5,681,319 A | 10/1997 | Biedermann et al. | |
| 5,690,630 A | 11/1997 | Errico et al. | |
| 5,704,936 A | 1/1998 | Mazel | |
| 5,716,355 A * | 2/1998 | Jackson et al. | 606/61 |
| 5,716,357 A | 2/1998 | Rogozinski | |
| 5,720,751 A | 2/1998 | Jackson | |
| 5,725,527 A | 3/1998 | Biedermann et al. | |
| 5,725,581 A * | 3/1998 | Brånemark | 606/73 |
| 5,733,286 A | 3/1998 | Errico et al. | |
| 5,735,851 A | 4/1998 | Errico et al. | |
| 5,741,268 A | 4/1998 | Schutz | |
| 5,800,435 A | 9/1998 | Errico et al. | |
| 5,814,046 A | 9/1998 | Hopf | |
| 5,863,293 A | 1/1999 | Richelsoph | |
| 5,873,878 A | 2/1999 | Harms et al. | |
| 5,876,403 A | 3/1999 | Shitoto | |
| 5,885,299 A | 3/1999 | Winslow et al. | |
| 5,904,682 A | 5/1999 | Rogozinski | |
| 5,910,141 A | 6/1999 | Morrison et al. | |
| 5,910,142 A | 6/1999 | Tatar | |
| 5,941,885 A | 8/1999 | Jackson | |
| 5,944,720 A | 8/1999 | Lipton | |
| 5,954,725 A | 9/1999 | Sherman et al. | |
| 5,961,516 A | 10/1999 | Graf | |
| 5,984,923 A | 11/1999 | Breard | |
| 6,010,504 A | 1/2000 | Rogozinski | |
| 6,017,343 A | 1/2000 | Rogozinski | |
| 6,074,391 A | 6/2000 | Metz-Stavenhagen et al. | |
| 6,077,262 A * | 6/2000 | Schlapfer et al. | 606/61 |
| 6,090,113 A | 7/2000 | Le Couedic et al. | |
| 6,113,604 A | 9/2000 | Whittaker et al. | |
| 6,123,707 A | 9/2000 | Wagner | |
| 6,132,433 A | 10/2000 | Whelan | |
| 6,139,549 A | 10/2000 | Keller | |
| 6,183,472 B1 | 2/2001 | Lutz | |
| 6,235,028 B1 | 5/2001 | Brumfield et al. | |
| 6,248,105 B1 | 6/2001 | Schlapfer et al. | |
| 6,251,112 B1 | 6/2001 | Jackson | |
| 6,254,146 B1 | 7/2001 | Church | |
| 6,264,658 B1 | 7/2001 | Lee et al. | |
| 6,267,765 B1 | 7/2001 | Taylor et al. | |
| 6,273,914 B1 | 8/2001 | Papas | |
| 6,280,442 B1 | 8/2001 | Barker et al. | |
| 6,296,642 B1 | 10/2001 | Morrison et al. | |
| 6,296,644 B1 | 10/2001 | Saurat | |
| 6,302,888 B1 | 10/2001 | Mellinger et al. | |
| 6,340,363 B1 | 1/2002 | Bolger et al. | |
| 6,342,056 B1 | 1/2002 | Mac-Thiong et al. | |
| RE37,665 E | 4/2002 | Ralph et al. | |
| 6,371,957 B1 | 4/2002 | Amerin et al. | |
| 6,440,133 B1 | 8/2002 | Beale et al. | |
| 6,482,207 B1 * | 11/2002 | Errico | 606/61 |
| 6,485,491 B1 * | 11/2002 | Farris et al. | 606/61 |
| 6,488,681 B2 | 12/2002 | Martin et al. | |
| 6,488,682 B2 | 12/2002 | Kikuchi | |
| 6,511,484 B2 | 1/2003 | Torode et al. | |
| 6,530,929 B1 | 3/2003 | Justis et al. | |
| 6,530,939 B1 | 3/2003 | Hopkins et al. | |
| 6,537,276 B2 | 3/2003 | Metz-Stavenhagen | |
| 6,540,748 B2 | 4/2003 | Lombardo | |
| 6,546,277 B1 | 4/2003 | Franck et al. | |
| 6,551,316 B1 | 4/2003 | Rinner et al. | |
| 6,551,318 B1 * | 4/2003 | Stahurski | 606/61 |
| 6,565,565 B1 * | 5/2003 | Yuan et al. | 606/272 |
| 6,620,167 B2 | 9/2003 | Deslauriers et al. | |
| 6,626,904 B1 | 9/2003 | Jammet et al. | |
| 6,660,006 B2 | 12/2003 | Markworth et al. | |
| 6,726,689 B2 | 4/2004 | Jackson | |
| 6,726,692 B2 | 4/2004 | Bette | |
| 6,743,231 B1 | 6/2004 | Gray et al. | |
| 6,749,613 B1 | 6/2004 | Conchy | |
| 6,755,829 B1 | 6/2004 | Bono et al. | |
| 6,770,075 B2 | 8/2004 | Howland | |
| 6,786,907 B2 * | 9/2004 | Lange | 606/61 |
| 6,793,656 B1 | 9/2004 | Mathews | |
| 6,802,844 B2 | 10/2004 | Ferree | |
| 6,827,722 B1 | 12/2004 | Schoenefeld | |
| 6,832,999 B2 | 12/2004 | Ueyama et al. | |
| 6,837,889 B2 | 1/2005 | Shluzas | |
| 6,884,241 B2 | 4/2005 | Bertranou et al. | |
| 6,932,822 B2 | 8/2005 | Oribe | |
| 6,964,666 B2 | 11/2005 | Jackson | |
| 6,979,334 B2 | 12/2005 | Dalton | |
| 7,083,621 B2 | 8/2006 | Shaolian et al. | |
| 2001/0034526 A1 | 10/2001 | Kuslich et al. | |
| 2002/0058942 A1 | 5/2002 | Biedermann | |
| 2002/0095153 A1 | 7/2002 | Jones et al. | |
| 2002/0123754 A1 | 9/2002 | Holmes et al. | |
| 2002/0138077 A1 | 9/2002 | Ferree | |
| 2003/0018342 A1 | 1/2003 | Oribe et al. | |
| 2003/0032965 A1 | 2/2003 | Schneiderman | |
| 2003/0105460 A1 | 6/2003 | Crandall et al. | |
| 2003/0153911 A1 | 8/2003 | Shluzas | |
| 2003/0176871 A1 | 9/2003 | Pavlov et al. | |
| 2003/0199872 A1 | 10/2003 | Markworth | |
| 2003/0208203 A1 | 11/2003 | Lim et al. | |
| 2004/0039384 A1 | 2/2004 | Boehm, Jr. et al. | |
| 2004/0049191 A1 | 3/2004 | Markworth | |
| 2004/0049196 A1 | 3/2004 | Jackson | |

| | | | | | | |
|---|---|---|---|---|---|---|
| 2004/0068269 A1 | 4/2004 | Bonati et al. | DE | 29903342 U1 | | 7/1999 |
| 2004/0133203 A1 | 7/2004 | Young et al. | DE | 29810798 U1 | | 12/1999 |
| 2004/0138662 A1 | 7/2004 | Landry et al. | EP | 159007 A3 | | 4/1986 |
| 2004/0143265 A1 | 7/2004 | Landry et al. | EP | 954247 A1 | | 11/1999 |
| 2004/0147936 A1 | 7/2004 | Rosenberg et al. | EP | 1072228 | * | 1/2001 |
| 2004/0158257 A1 | 8/2004 | Bonati et al. | EP | 1187568 A2 | | 3/2002 |
| 2004/0158258 A1 | 8/2004 | Bonati et al. | EP | 1281365 A1 | | 2/2003 |
| 2004/0172022 A1 | 9/2004 | Landry et al. | EP | 1190678 A3 | | 3/2003 |
| 2004/0176766 A1 | 9/2004 | Shluzas | EP | 1317215 A2 | | 6/2003 |
| 2004/0215190 A1 | 10/2004 | Nguyen | EP | 1604618 A1 | | 11/2005 |
| 2004/0243139 A1 | 12/2004 | Lewis et al. | EP | 1603469 A1 | | 12/2005 |
| 2004/0254576 A1 | 12/2004 | Dunbar | EP | 1604617 A1 | | 12/2005 |
| 2004/0260283 A1 | 12/2004 | Wu et al. | EP | 1605844 A2 | | 12/2005 |
| 2004/0260287 A1 | 12/2004 | Ferree | FR | 2659546 A1 | | 9/1991 |
| 2004/0267264 A1 | 12/2004 | Konieczynski et al. | FR | 2697428 | | 11/1992 |
| 2004/0267275 A1 | 12/2004 | Cournoyer et al. | FR | 2698533 | | 6/1994 |
| 2004/0267279 A1 | 12/2004 | Casutt et al. | FR | 2697428 | | 9/1997 |
| 2005/0010220 A1 | 1/2005 | Casutt et al. | FR | 2775583 | | 8/2000 |
| 2005/0027292 A1* | 2/2005 | Bernard et al. ............... 606/61 | FR | 2795622 | | 9/2001 |
| 2005/0033299 A1 | 2/2005 | Shluzas | GR | 1003754 | | 1/2002 |
| 2005/0070917 A1 | 3/2005 | Justis | WO | WO98/48717 | | 11/1998 |
| 2005/0070918 A1 | 3/2005 | Zwirnmann et al. | WO | WO0128436 A1 | | 4/2001 |
| 2005/0080418 A1 | 4/2005 | Simonson | WO | WO02/24087 A1 | | 3/2002 |
| 2005/0085813 A1 | 4/2005 | Spitler et al. | WO | WO03094741 A3 | | 11/2003 |
| 2005/0090824 A1 | 4/2005 | Shluzas | WO | WO 2004/017847 A2 | | 3/2004 |
| 2005/0107788 A1 | 5/2005 | Beaurain | WO | WO 2004/041100 A1 | | 5/2004 |
| 2005/0131408 A1 | 6/2005 | Sicvol et al. | WO | WO2004047650 A3 | | 6/2004 |
| 2005/0131419 A1 | 6/2005 | McCord | WO | WO2004082464 A3 | | 9/2004 |
| 2005/0131420 A1 | 6/2005 | Techiera | WO | WO2004084744 | | 10/2004 |
| 2005/0131421 A1 | 6/2005 | Anderson | WO | WO2005041799 A1 | | 5/2005 |
| 2005/0131422 A1 | 6/2005 | Anderson | WO | WO03/026523 | | 11/2005 |
| 2005/0137593 A1 | 6/2005 | Gray | WO | WO2005/104970 | | 11/2005 |
| 2005/0149023 A1 | 7/2005 | Ritland | WO | WO2005/110257 A1 | | 11/2005 |
| 2005/0149036 A1 | 7/2005 | Varieur | WO | WO2005102195 A1 | | 11/2005 |
| 2005/0149048 A1 | 7/2005 | Leport et al. | WO | WO2005/117731 A1 | | 12/2005 |
| 2005/0149053 A1 | 7/2005 | Varieur | WO | WO2005/122926 A1 | | 12/2005 |
| 2005/0154389 A1 | 7/2005 | Selover | WO | WO2005/122930 A2 | | 12/2005 |
| 2005/0171540 A1 | 8/2005 | Lim | WO | WO2005122928 A2 | | 12/2005 |
| 2005/0171549 A1 | 8/2005 | Boehm, Jr. | WO | WO2005122929 A1 | | 12/2005 |
| 2005/0261687 A1 | 11/2005 | Garamszegi et al. | WO | WO2006009753 A1 | | 1/2006 |
| 2005/0273099 A1 | 12/2005 | Baccelli et al. | | | | |
| 2005/0277919 A1 | 12/2005 | Slivka | | | | |
| 2005/0283153 A1 | 12/2005 | Poyner et al. | | | | |
| 2005/0283157 A1 | 12/2005 | Coates et al. | | | | |
| 2005/0283244 A1 | 12/2005 | Gordon et al. | | | | |
| 2006/0036244 A1 | 2/2006 | Spitler et al. | | | | |
| 2006/0149252 A1 | 7/2006 | Markworth et al. | | | | |

FOREIGN PATENT DOCUMENTS

DE 9402695 5/1994

OTHER PUBLICATIONS

International Search Report issued for PCT/US2004/035000, dated Mar. 2, 2005.
Partial International Search Report issued for PCT/US2005/036339 dated Jan. 23, 2006.
Hoffman, Mary C.; USPTO Office Action in U.S. Appl. No. 10/690,211 dated Nov. 29, 2007.

* cited by examiner

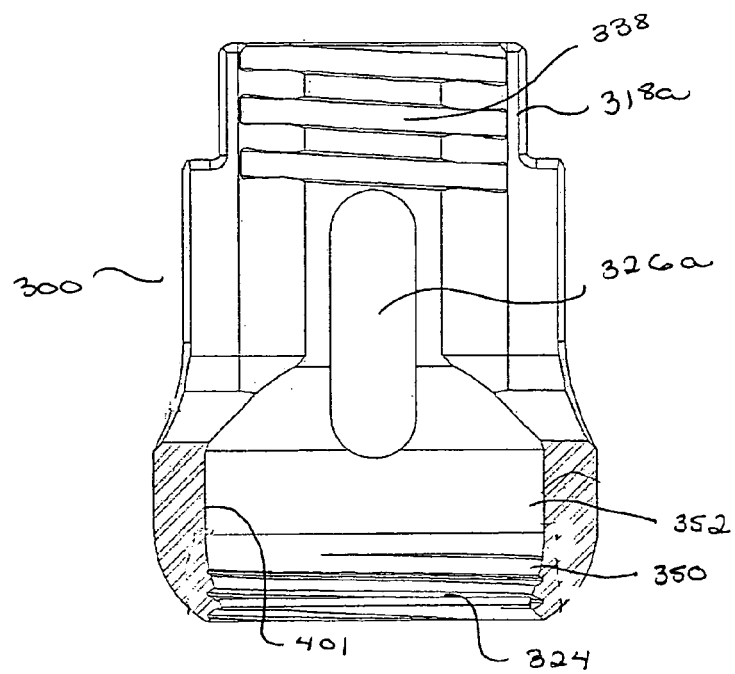
FIG. 4
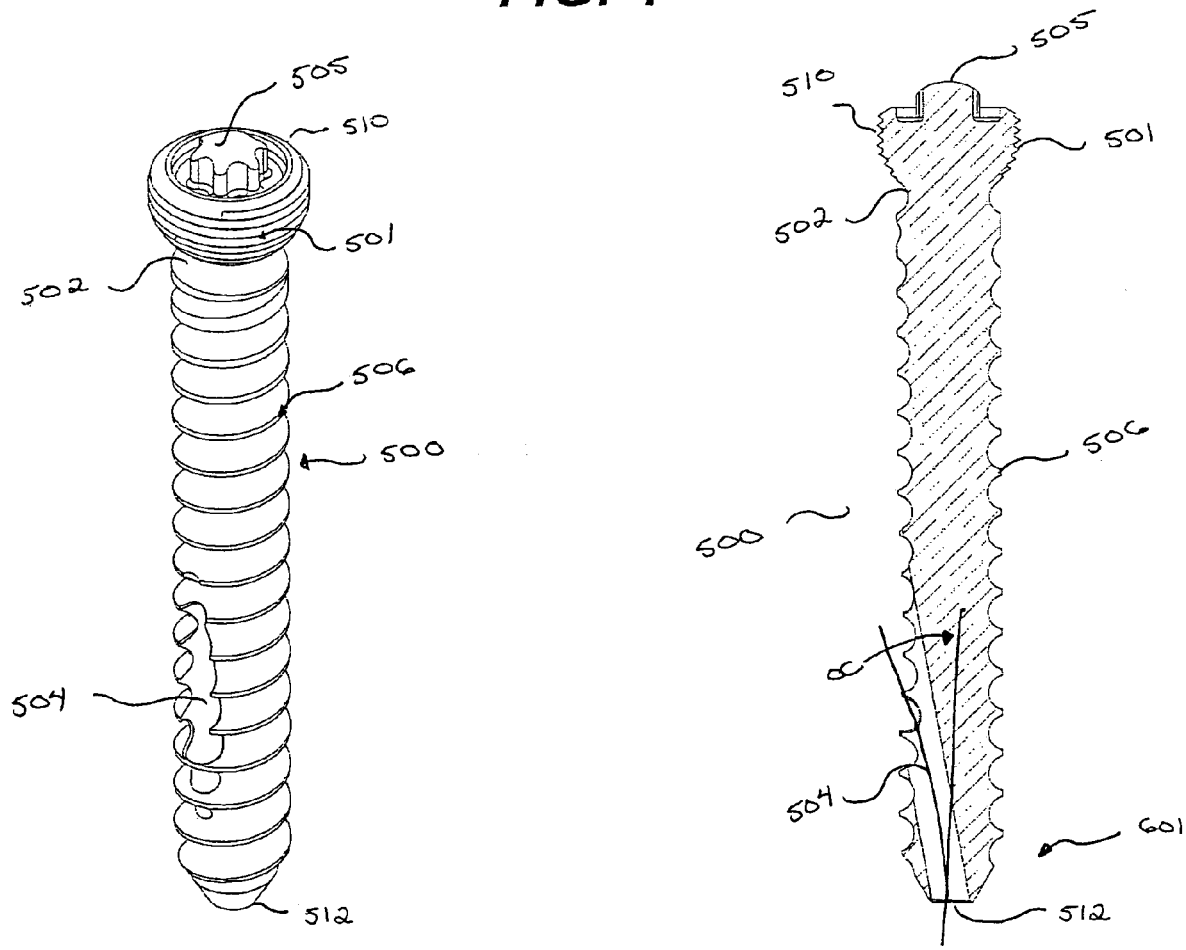
FIG. 5  FIG. 6

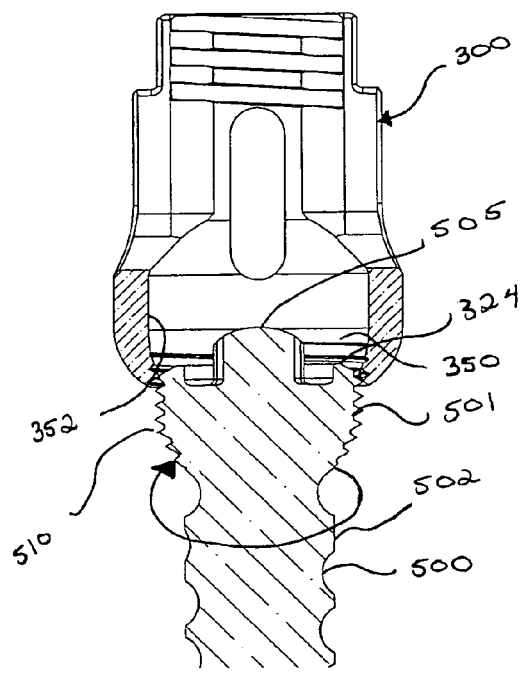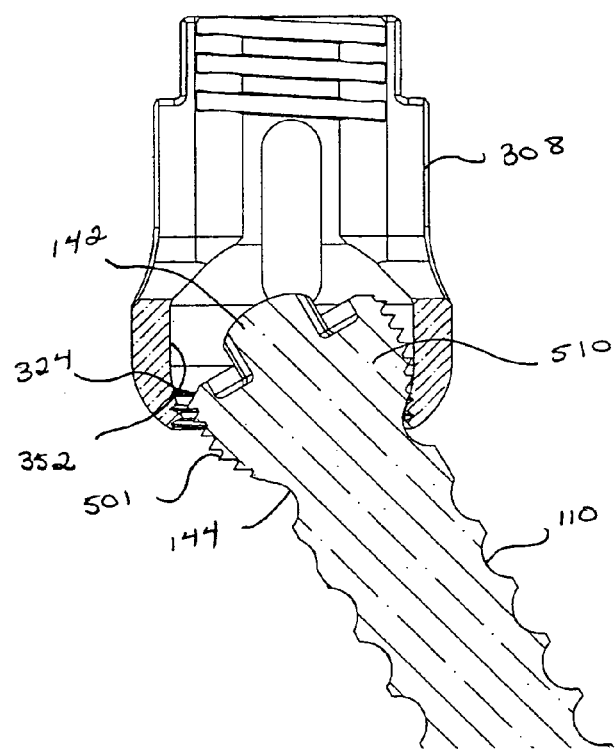
FIG. 10a
FIG 10b

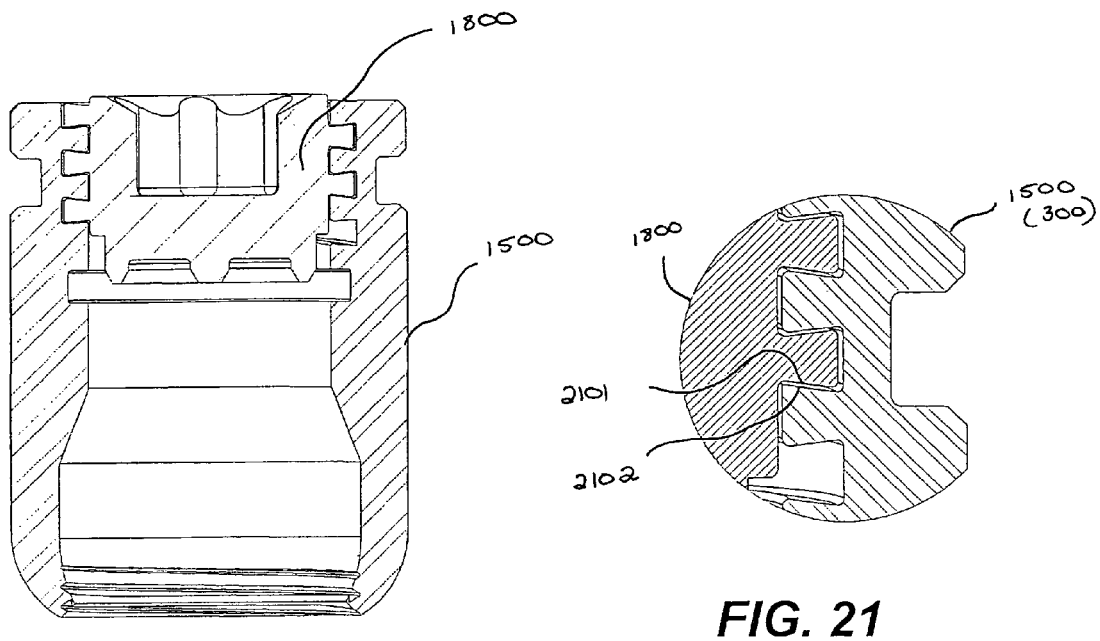
FIG. 20
FIG. 21
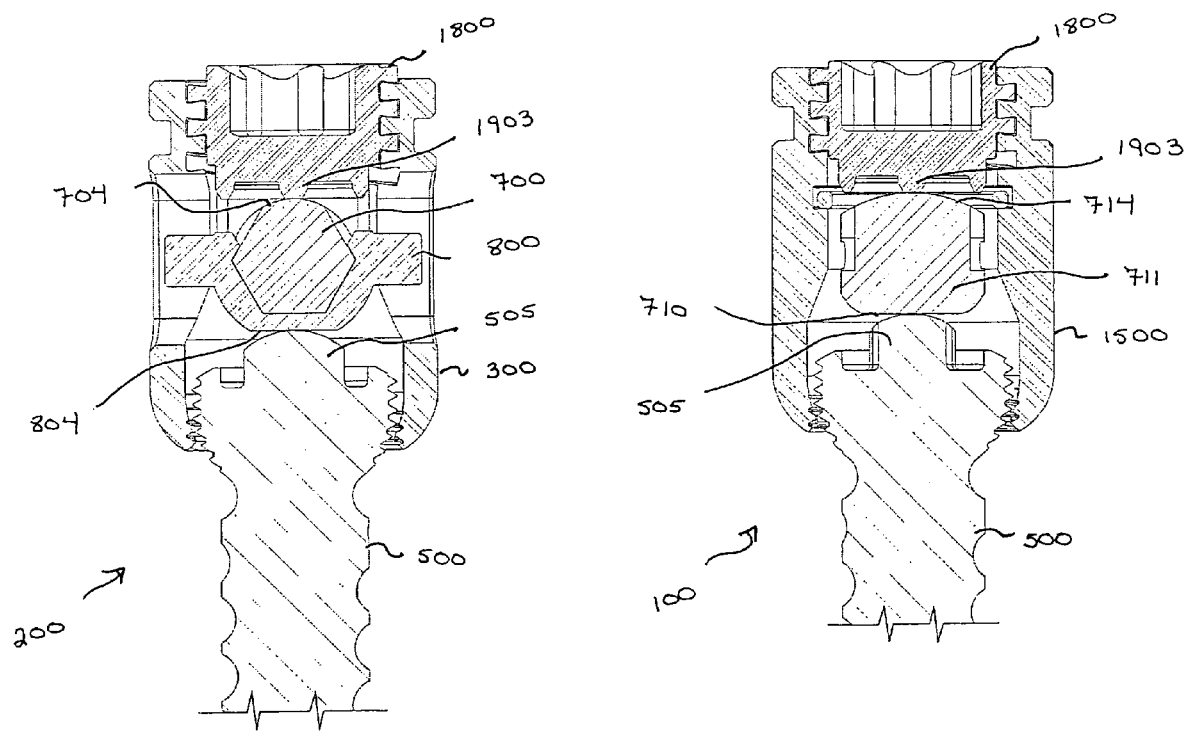
FIG. 22a
FIG. 22b

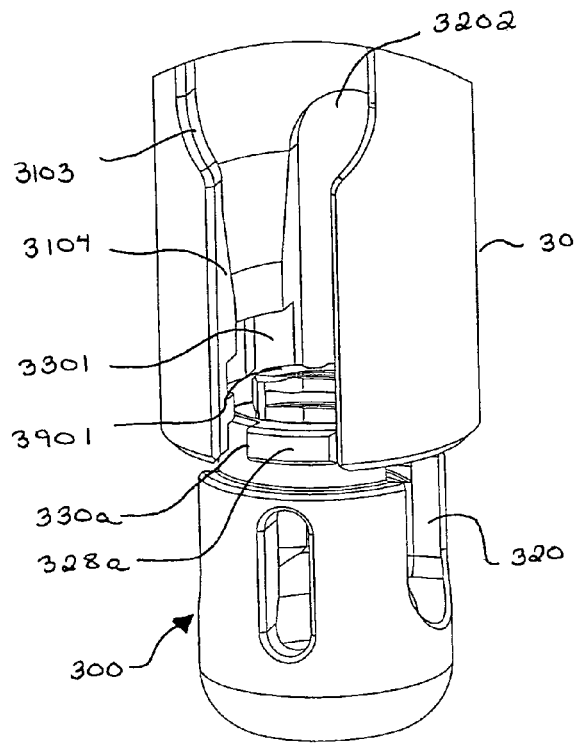
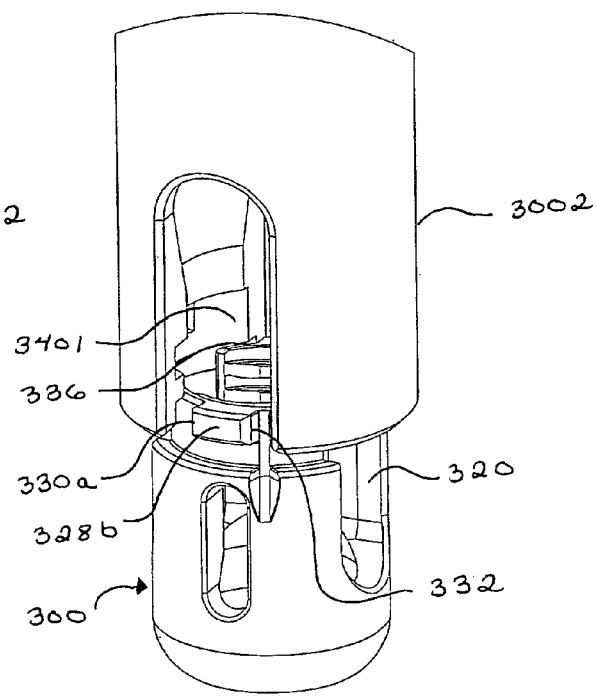
FIG. 39　　　　FIG. 40
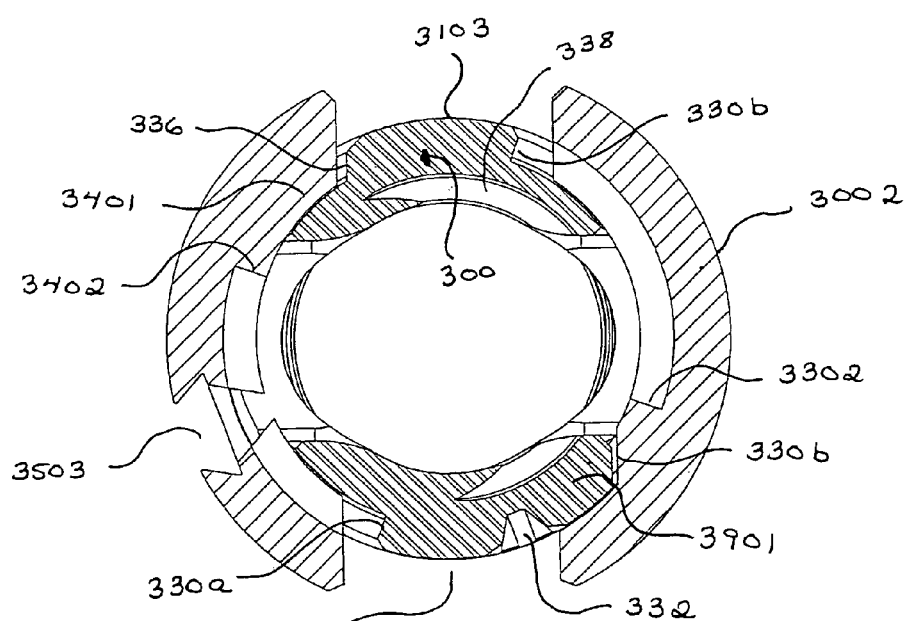
FIG. 41

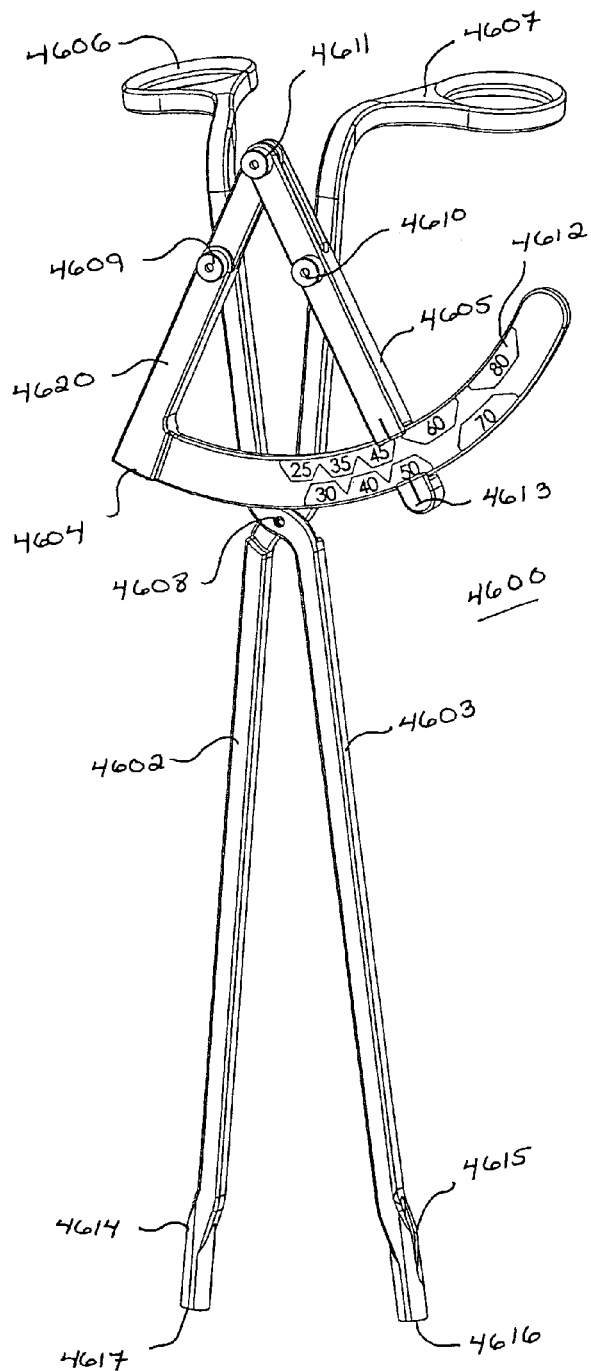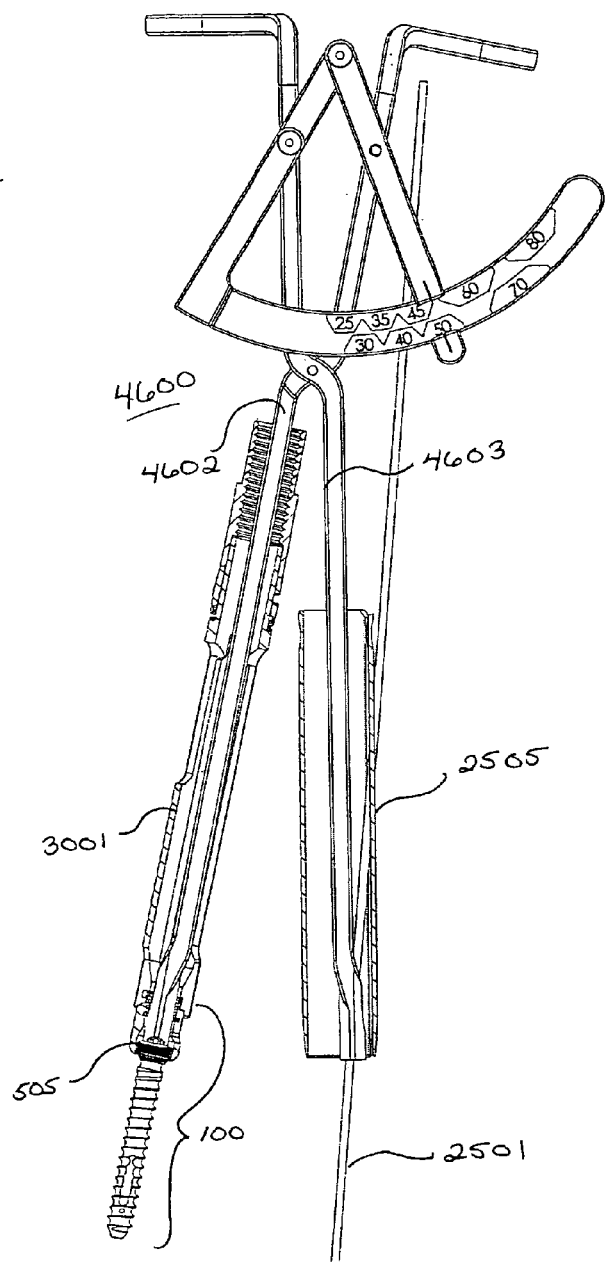
FIG. 46
FIG. 47

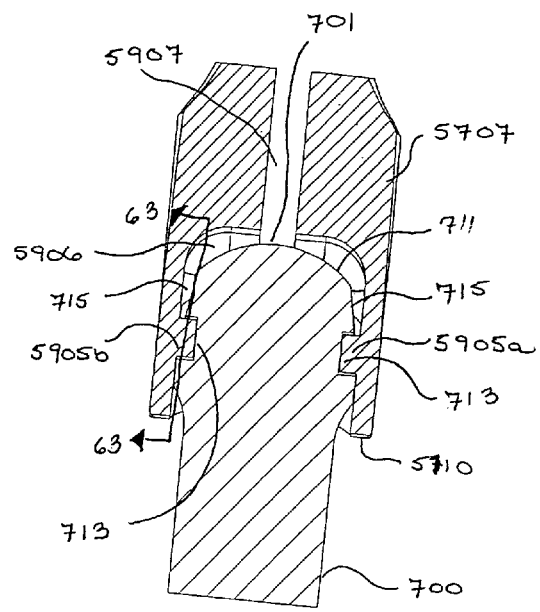
FIG. 62
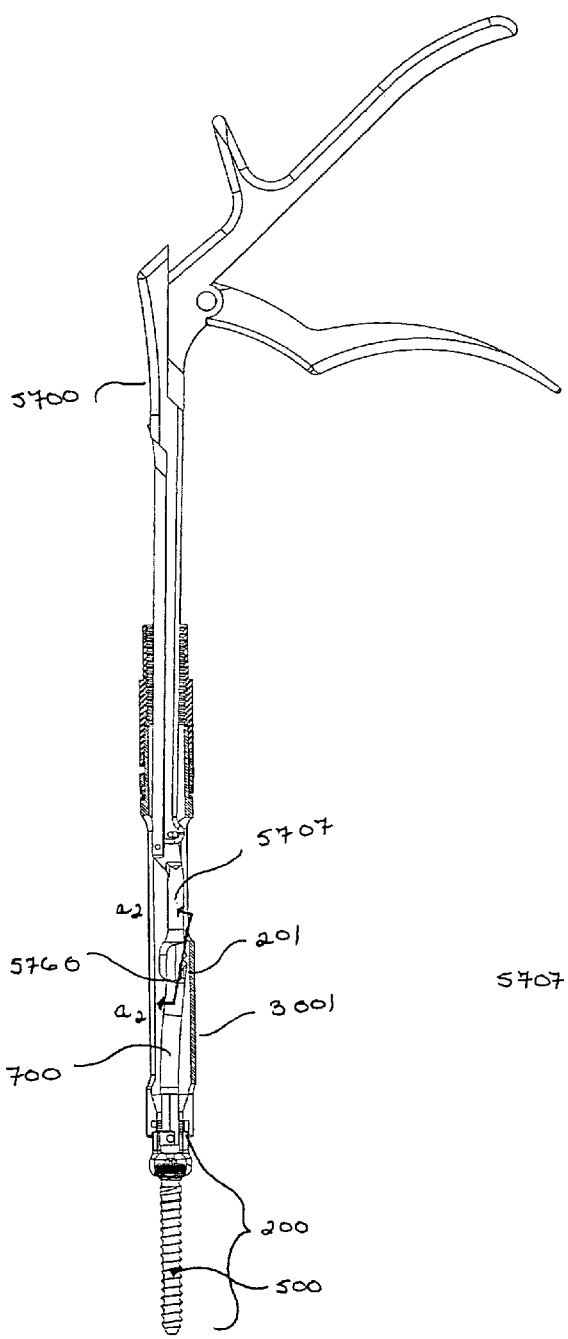
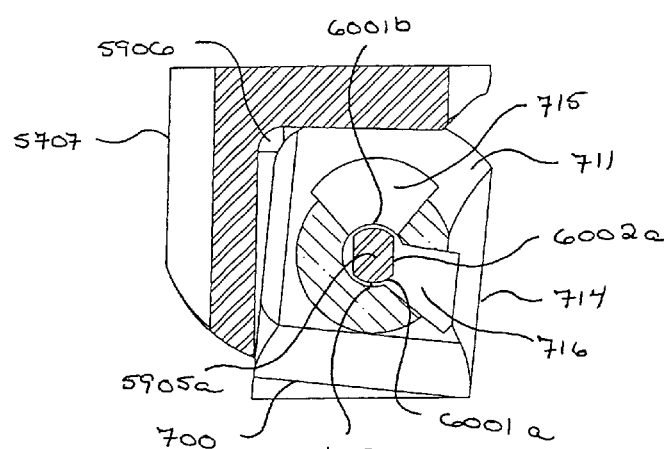
FIG. 63
FIG. 61

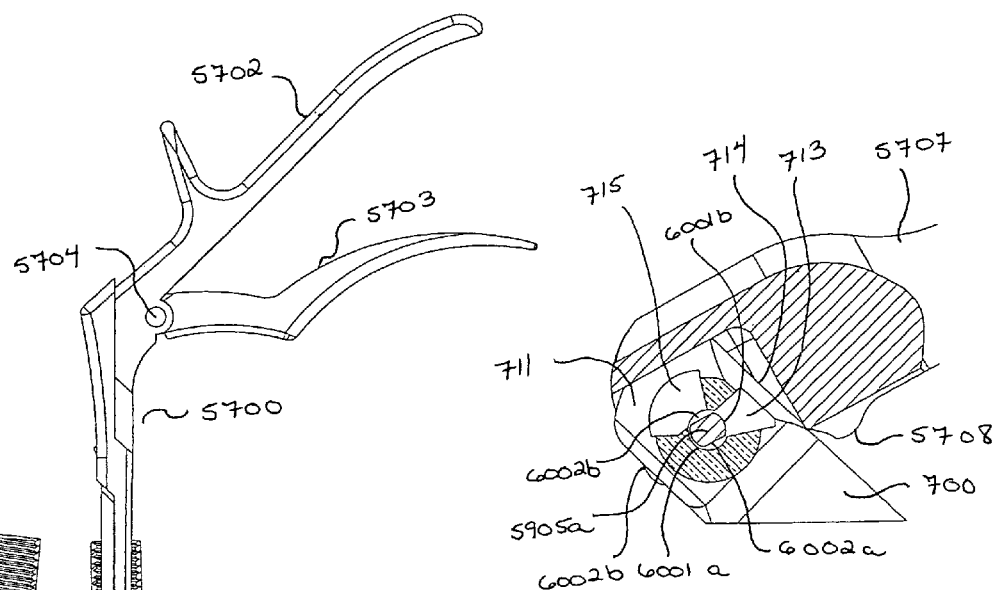
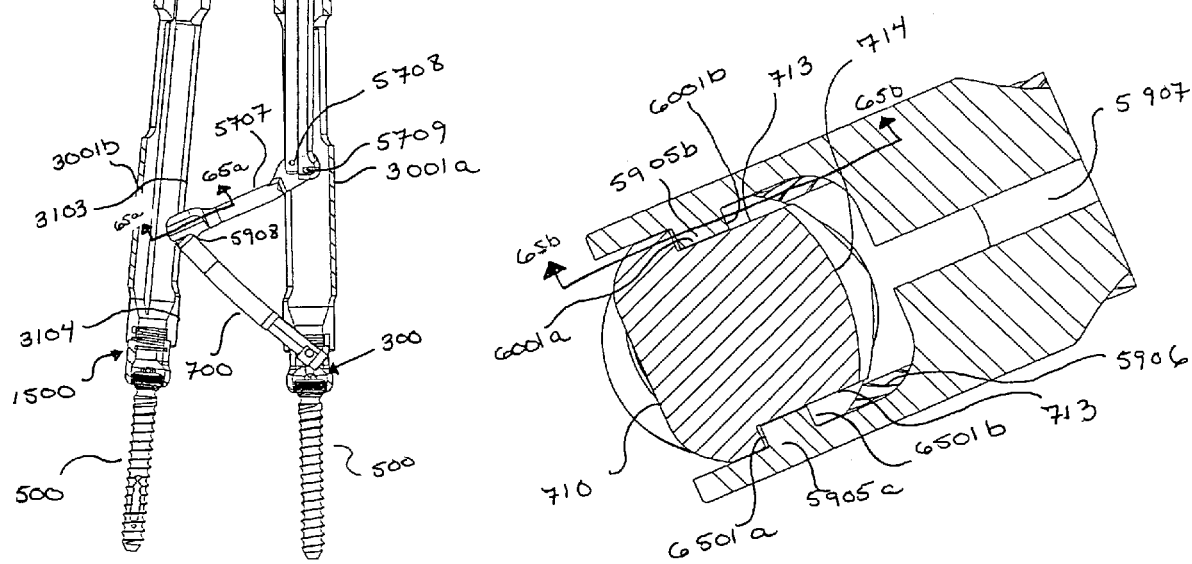
FIG. 64
FIG. 65a

IMPLANT ASSEMBLY AND METHOD FOR USE IN AN INTERNAL STRUCTURE STABILIZATION SYSTEM

CROSS-REFERENCE TO RELATED APPLICATIONS

The present application is a continuation-in-part of Utility patent application Ser. No. 10/690,211, filed Oct. 21, 2003 entitled "SYSTEM AND METHOD FOR STABILIZATION OF INTERNAL STRUCTURES," the disclosure of which is hereby incorporated herein by reference.

TECHNICAL FIELD

This invention relates to bone stabilization systems, and more particularly to implant assemblies and their components for stabilizing bony structures such as vertebrae.

BACKGROUND OF THE INVENTION

The human spine provides a vast array of functions, many of which are mechanical in nature. The spine is constructed to allow nerves from the brain to pass to various portions of the middle and lower body. These nerves, typically called the spinal cord, are located in a region within the spine called the spinal canal. Various nerve bundles emerge from the spine at different locations along the lateral length of the spine. In a healthy spine, these nerves are protected from damage and/or undue pressure thereon by the structure of the spine itself.

The spine has a complex curvature made up of a plurality (24 in all) of individual vertebrae separated by intervertebral discs. These discs hold the vertebrae together in a flexible manner so as to allow a relative movement between the vertebrae from front to back and from side to side. This movement then allows the body to bend forward and backward, to twist from side to side, and to rotate about a vertical axis. Throughout this movement, when the spine is operating properly the nerves are maintained clear of the hard structure of the spine.

Over time, or because of accidents, the intervertebral discs loose height, become cracked, dehydrated, or herniated. The result is that the disc height is reduced leading to compression of the nerve bundles, causing pain and in some cases damage to the nerves.

Currently, there are many systems and methods at the disposal of a physician for reducing, or eliminating, the pain by minimizing the stress on the nerve bundles. In some instances, the existing disk is removed and an artificial disk is substituted therefore. In other instances, two or more vertebrae are fused together to prevent relative movement between the fused discs.

Often there is required a system and method for maintaining, or recreating, proper space for the nerve bundles that emerge from the spine at a certain location. In some cases a cage or bone graft is placed in the disc space to preserve, or restore, height and to cause fusion of the vertebral level. As an aid in stabilizing the vertebrae, one or more rods or braces are placed between the fused vertebrae with the purpose of the rods being to support the vertebrae, usually along the posterior of the spine while fusion takes place. These rods are often held in place by anchors which are fitted into the pedicle of the vertebrae. One type of anchor is a pedicle screw, and such screws come in a variety of lengths, diameters, and thread types.

One problem when connecting the braces to the anchors is to position the braces in place as quickly as possible and without doing more damage to the surrounding tissue and muscle of the patient as is absolutely necessary. For that reason, procedures have been developed that allow the physician to secure the anchors in the bony portion of the spine and to then connect the brace between the anchors. Techniques have been developed to allow the surgeon to perform this procedure in a minimally invasive manner, utilizing a percutaneous method.

In one such procedure, a first pedicle screw is inserted in a first vertebra to be stabilized. This screw is inserted using a tube, or cannula, extending through the patient's skin to the pedicle portion of the vertebrae. A second pedicle screw is inserted through a second cannula into the second vertebrae to be stabilized. Under current practice, the physician then must work the brace, or other supporting device, so that each brace end is positioned properly with respect to the preplaced pedicle screws. In order to properly position the brace ends fluoroscope pictures are taken as the brace is worked into position. It is difficult for the physician to know the exact orientation of the brace and even to know for certain when the brace ends have been properly positioned. U.S. Pat. No. 6,530,929 shows one instrument for positioning a stabilization brace between two preplaced anchors.

Another problem with both of the approach discussed above, is that the braces must be made significantly longer than the distance between the pedicle screws to allow for proper attachment of the brace ends to the screws. Placement of the brace is sensitive to anchor alignment since the adjustment establishes the trajectory of the brace. If this trajectory is not established properly, the brace would have to pass through tissue or would be blocked by bone. Also, the design of the brace necessitates a separate incision in the back of the patient, and the learning curve for manipulation the insertion device of the '929 patent is difficult.

A more recent approach has been to insert cannulae over the respective pedicle areas of the vertebrae to be stabilized, and then measure the distance between the cannulae. This measurement is then used to select, or cut a rod, adding a bit to the dimension to ensure that the rod can be rigidly affixed to each anchor. In addition, each rod must be bent a certain amount (or a pre-bent rod utilized) to reflect the curvature of the spine. Once the proper rod dimension and shape is obtained each end of the rod is positioned in its respective cannulae and the rod is worked downward toward the anchors passing through a separation of muscle and tissue from the skin line to the pedicle site. This placement of the rod is facilitated by a long handheld gripper which must then be manipulated to position the rod ends over the respective anchors so as to capture the rod end with set screws in the tops of the respective anchors. Proper positioning of the rod ends is difficult, and requires repeated use of fluoroscopy to insure that the rod is fully seated and in a correct position. If the rod is not fully seated, the construct will not assemble correctly and will most likely fail. Further, the failure of the construct will most likely not be immediately apparent.

What is needed is a stabilization assembly which uses a rod with a predefined bend, the rod being preassembled with a bone anchor and movable to span from one bone anchor to another bone anchor using extensions and tools designed to work with the assembly.

BRIEF SUMMARY OF THE INVENTION

The present invention describes an assembly for use in spinal stabilization procedures. The assembly includes a first and second bone anchor assemblies inserted into a first and second bony structure, such as the pedicle of a vertebra. The first bone anchor assembly is formed by an anchor, a polyaxial head connected to the anchor such that the anchor has a conical range of motion in relation to the head, and a snap ring mounted in the poly-axial head. The second bone anchor assembly is formed by an anchor, a poly-axial head connected to the anchor, a slide ring rotatably mounted in the poly-axial head, and a connector slideably mounted in the slide ring. By rotating the connector and slide ring, the connector of the second bone anchor assembly is movable between two positions. The first position, where the connector is axially inline with the bone anchor, corresponds to the connector being mated with a drive mechanism on the anchor such that a drive tool can be engaged with the connector and used to turn the anchor. The end of the connector is then rotated through an arc from in an extension connected to the bone anchor assembly to the second position. In the second position, the connector has a proximal end engaged with a cavity in the poly-axial head of the first bone anchor assembly, thereby connecting the assembly and allowing the entire assembly to be held in a fixed rigid orientation when locking caps are installed in the poly-axial heads. Once the end of the connector is in the cavity of the poly-axial connector-capturing assembly, or even in an opening of the extension holding the poly-axial connector-capturing assembly, the position of the connector end is known.

A method for assembling a spinal stabilization assembly is also described where a first bone anchor assembly is attached to an extension and the bone anchor assembly is inserted into a first bony structure along a guide wire passing through an off-axis guide in the first bone anchor assembly. The first bone anchor assembly is tightened into place by a drive mechanism inserted into the extension and fitted with the anchor of the bone anchor assembly. A distance is then measured between the first bone anchor and a second bony structure, the distance determining the length of connector to be used. A second guide wire is inserted followed by a tap. A second bone anchor assembly is then attached to another anchor, inserted down the second guide wire, and driven into the bony structure as well. The connector is then rotated from the second bone anchor assembly so that an end of the connector is captured by a cavity in the second bone anchor assembly. Locking caps are installed in the bone anchor assemblies to hold the entire assembly in a fixed orientation.

As part of the stabilization assembly, an assembly is described that includes a connector and a bracket, the connector having flat surfaces along its length that mate with flat surfaces in the bracket, creating an assembly that allows the connector to slide along a portion of its length inside the bracket.

Also as part of the stabilization assembly a poly-axial head is described that includes a cavity in the center of the head with a groove in the cavity for accepting a snap ring. The snap ring is operable to lock the end of a connector in place when the end is inserted into the cavity, creating an audible and tactile feedback upon seating.

An anchor for use with the stabilization assembly is described, the anchor having a threaded shank portion and an off-axis guide formed in the shank. The off-axis guide being formed by a hollow bore from the tip of the shank toward the head of the shank, with the bore exiting out the side of the shank somewhere between the tip and the head.

Further, a locking cap for use with the stabilization assembly is described. The locking cap formed by a locking ring which is threaded into a poly-axial head, the locking ring operable to cause the poly-axial head and anchor to assume a fixed, rigid relationship with one another, effectively locking out the conical freedom of the anchor with respect to the head while still allowing the connector to slide within the slide ring. The compression cap threads into the locking ring and acts to compress the connector and slide ring locking the connector into position, and preventing the connector from sliding within the slide ring.

BRIEF DESCRIPTION OF THE DRAWINGS

For a more complete understanding of the present invention, reference is now made to the following descriptions taken in conjunction with the accompanying drawing, in which:

FIG. 4 shows a sectional view of FIG. 3 taken along line 3-3;

FIG. 5 is a perspective view of an embodiment of the anchor from FIG. 1;

FIG. 6 is a cross-section of the anchor from FIG. 5 showing partially cannulated channel 504;

FIG. 10A is a cut-away view showing the drive mechanism of the rod of FIG. 7 mated with the anchor of FIG. 5.

FIG. 10B is an alternate cut-away view of the rod of FIG. 7 capturing the anchor of FIG. 5 in a pocket beyond the receiving threads of the rod;

FIG. 20 is a cross-sectional view of the locking cap of FIG. 18 threaded into the capturing head of FIG. 15;

FIG. 21 is a cross-sectional view of an embodiment of the locking cap and capturing head employing helical dovetail interlocking threads according to the present invention;

FIG. 22a is a cross-sectional view of an anchor, head, rod, and locking cap assembly;

FIG. 22b is a cross-sectional view of an anchor, capturing head, rod, and locking cap assembly;

FIG. 46 is a perspective view of an angular measurement tool in accordance with the present invention;

FIG. 47 is a side view of the tool of FIG. 46 in relation to a cut-away view of the assembly of FIG. 30 mated to the head of FIG. 4 and anchor of FIG. 5;

FIG. 64 is a side view the rod transfer tool of FIG. 57 operating to transfer a rod from the assembly of FIG. 11 into the capturing head of the assembly of FIG. 14 using the assemblies of FIG. 30;

FIG. 65a shows a cross-section through section 65a-65a of FIG. 64;

FIG. 65b shows a cross-section through 65b-65b of FIG. 65a;

DETAILED DESCRIPTION OF THE INVENTION

To better understand the devices, assemblies, tools, and methods described below, and understanding of the procedure through which the back stabilization of the present invention is placed into the vertebrae of a patient is required.

Reference is made to the figure numbers where specific embodiments of the devices, assemblies, tools and methods are described in greater detail to aid in the understanding of those particular items.

An operation to insert a pedicle screw assembly into a patient's back to immobilize certain vertebrae in order to allow bone grafts to ultimately fuse those vertebrae begins with the surgeon inserting a standard bone biopsy needle into the pedicle of a first vertebra and using the bone biopsy needle to place a guide wire where the first pedicle screw should be inserted. Using the guide wire, progressively larger tissue expanders are inserted into the patient to expand, or dilate, the incision to the size necessary to accommodate the instruments to be used, with the final cannula being left in the incision after the smaller ones are removed. (see, FIGS. 25-27). Next, an awl (FIG. 28) is used to enlarge the hole in the pedicle made by the bone biopsy needle with the awl being inserted over the guide wire to ensure proper placement in the pedicle. A tap (FIG. 29), having a diameter slightly smaller than the pedicle screw to be used, is inserted down the guide wire and used to tap the hole started by the bone biopsy needle and the awl, making it ready to accept the first pedicle screw.

Figures 52, 53:
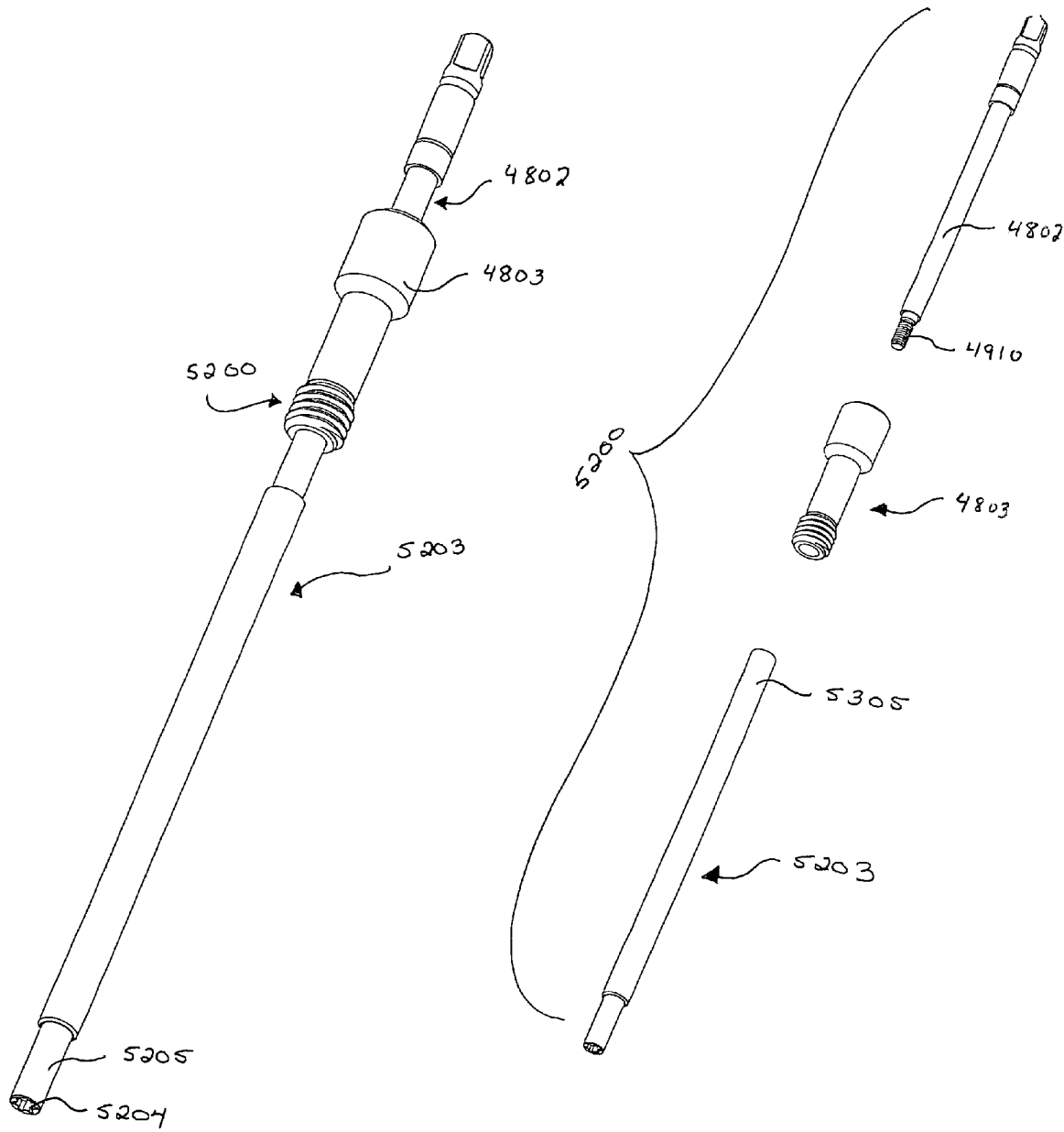
FIG. 52 is a perspective view of an embodiment of a drive tool with a torque screw head in accordance with the present invention.
FIG. 53 is an exploded view of the drive tool of FIG. 52.

A first pedicle screw (FIG. 5) with a poly-axial rod-capturing head (FIG. 15) attached to form a rod-capturing pedicle screw assembly (FIG. 14) is inserted down the guide wire using the off-axis screw guide of the pedicle screw and into the hole left by the tap. Attached to this pedicle screw assembly are an extension (FIGS. 30-32) and drive mechanism with a torque head attachment (FIGS. 52 and 53). The extension allows access to the pedicle screw assembly once it is in place. The drive mechanism is used to screw the pedicle screw assembly in place and is removed from the extension once the pedicle screw assembly is set to the desired depth.

A tissue separator is used to make a path from the first and second, and potentially additional, vertebra where the second pedicle screw assembly will be inserted. As described above a bone biopsy needle is used to insert a guide wire into the second vertebra where the second pedicle screw assembly is to be placed. Once the guide wire is in place a measurement tool (FIGS. 46 and 47) is used measure the distance between the first pedicle screw assembly and the guide wire, the measurement determining the length of the rod to be used. The second pedicle screw assembly (FIG. 11) is then chosen according to the proper length of the rod. The second pedicle screw assembly is formed by a pedicle screw identical to the pedicle screw of the first assembly, a poly-axial rod-assembly head (FIG. 3), a slide ring (FIG. 8), and a rod (FIGS. 7 and 9) all connected to another extension. A drive mechanism with a head to accept the end of the rod (FIGS. 48 and 49) is used to drive the second pedicle screw assembly into the pedicle of the second vertebra, using the rod to transfer torque from the drive mechanism to the pedicle screw. As before the pedicle screw is sent along the guide wire using the off-axis screw guide in the pedicle screw. The screw is then inserted to the desired depth using the drive mechanism, which is then removed leaving the extension attached to the pedicle screw assembly.

Figure 59:
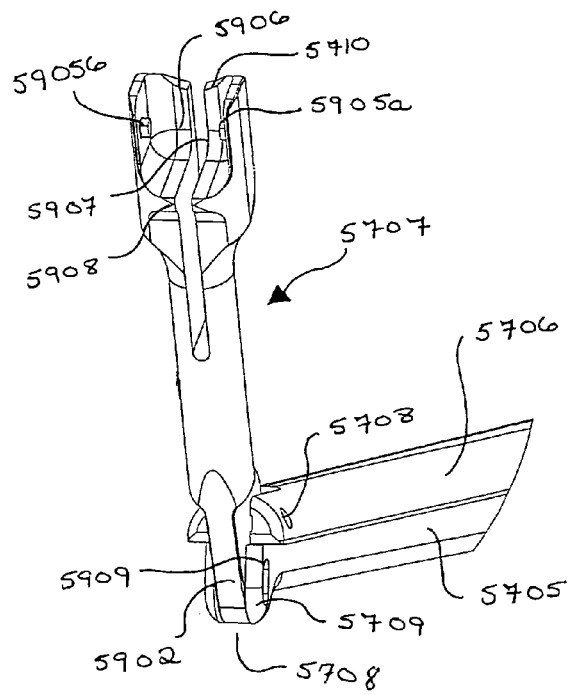
FIG. 59 shows is a perspective view of the distal arm end of the rod transfer tool of FIG. 57.
Figure 60:
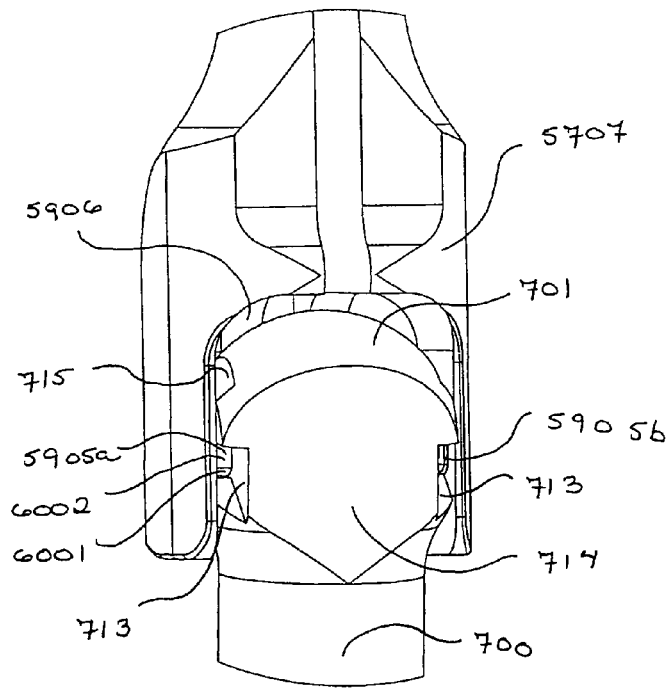
FIG. 60 is a side view of the tip of the distal arm of the rod transfer tool of FIG. 57.
Figure 61:
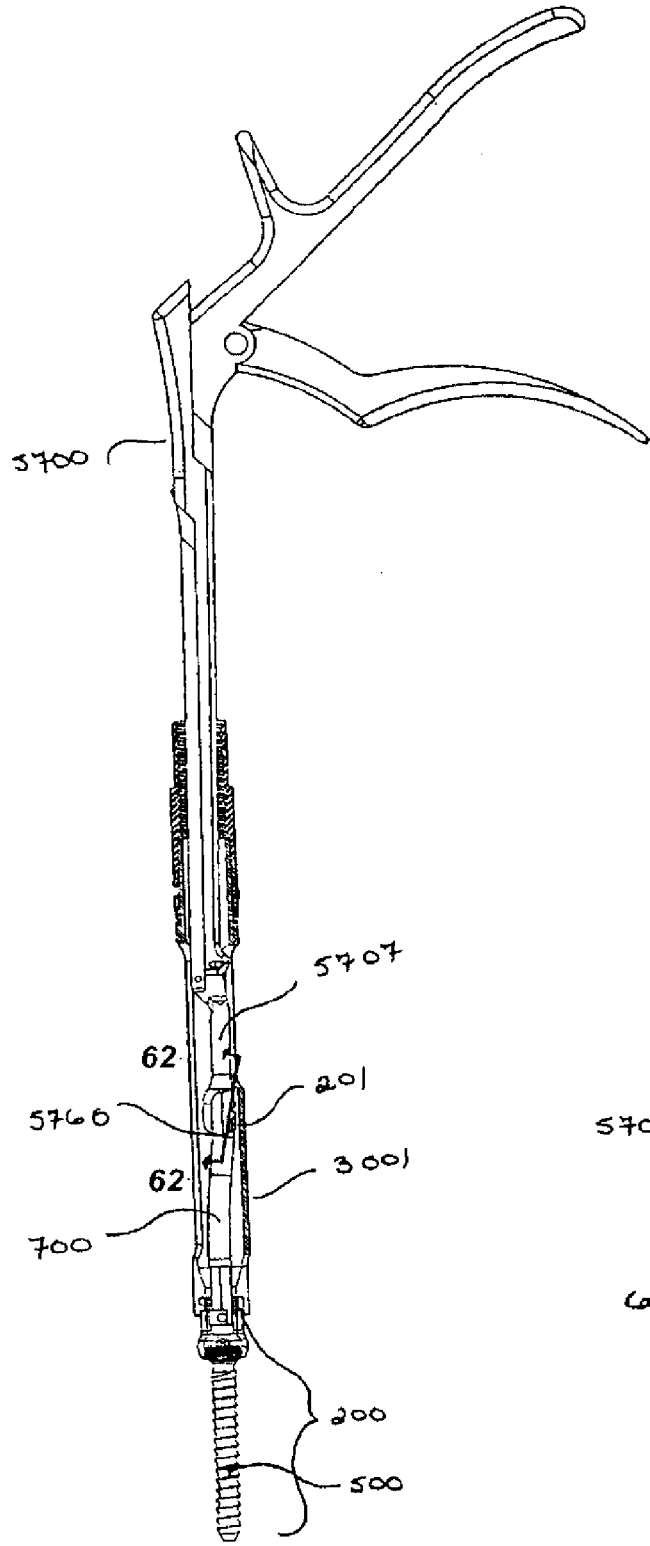
FIG. 61 is a side view of the rod transfer tool of FIG. 57 in operation with the assemblies of FIGS. 11 and 30.

A rod transfer tool (FIGS. 57 and 58) is then inserted into the extension which is attached to the pedicle screw assembly with the poly-axial rod-assembly head until the distal end of the rod transfer tool (FIG. 59) locks with the end of the rod (FIGS. 60 and 61). The rod transfer tool is then used to disengage the rod from the drive mechanism of the pedicle screw, and guide the rod down into the extension holding the pedicle screw assembly with the poly-axial rod-capturing head, the end of rod ultimately being pressed down into the poly-axial rod-capturing head, where it is held in place by a clip ring (FIG. 16) in the rod-capturing head.

After the rod is pressed into the poly-axial rod-capturing head, the rod transfer tool is removed and locking caps (FIG. 18) are screwed into each of the poly-axial heads using a drive tool and counter torque handle assembly (FIG. 65c). The counter torque handle is used to provide a counter torque force to the torque applied by the drive tool, thereby preventing the loading of the rod assembly with torque when the locking caps are tightened into place.

After the locking caps are tightened appropriately, the extensions are removed leaving the stabilization system (FIG. 1) in place. Bone grafts can then be placed between the two stabilized vertebrae which will then grow to fuse the vertebrae together while the stabilization system holds the vertebral segment.

Figure 73:
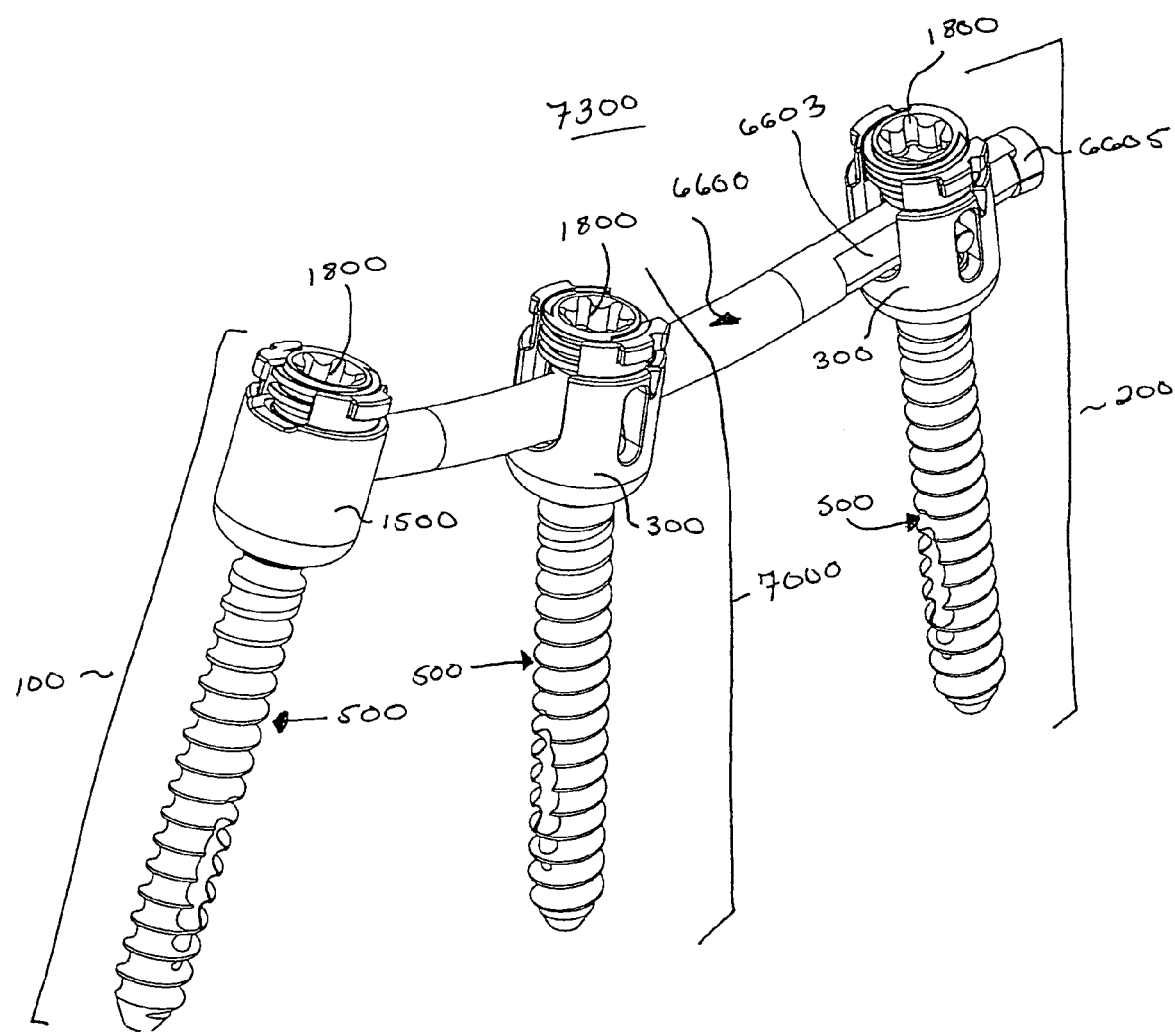
FIG. 73 is a perspective view of the three pedicle assembly with locking caps installed.

In addition to stabilization systems connection two bony structures, such as vertebrae, stabilization systems my be employed that rigidly connect three or more vertebrae. (FIG. 73). In a three pedicle stabilization system, the outer polyaxial head assemblies are inserted into the first and second vertebrae, which surround the third vertebra, as described above. To position the third poly-axial head assembly, an arc defining tool (FIG. 74) is required since the rod has a predefined curvature and the third, or middle, poly-axial head assembly must be precisely located to capture the middle of the rod when it is transferred. Additionally, because of the additional length and curvature of the three pedicle rod over the two pedicle rod, the end of the rod with the drive mechanism is formed with an angle to the drive mechanism to minimize the diameter of the extension required. The additional length of the rod also requires a different rod transfer tool to move the rod into position in the poly-axial head assemblies (FIG. 70), and an extension for the middle poly-axial head assembly (FIG. 71).

Figure 1:
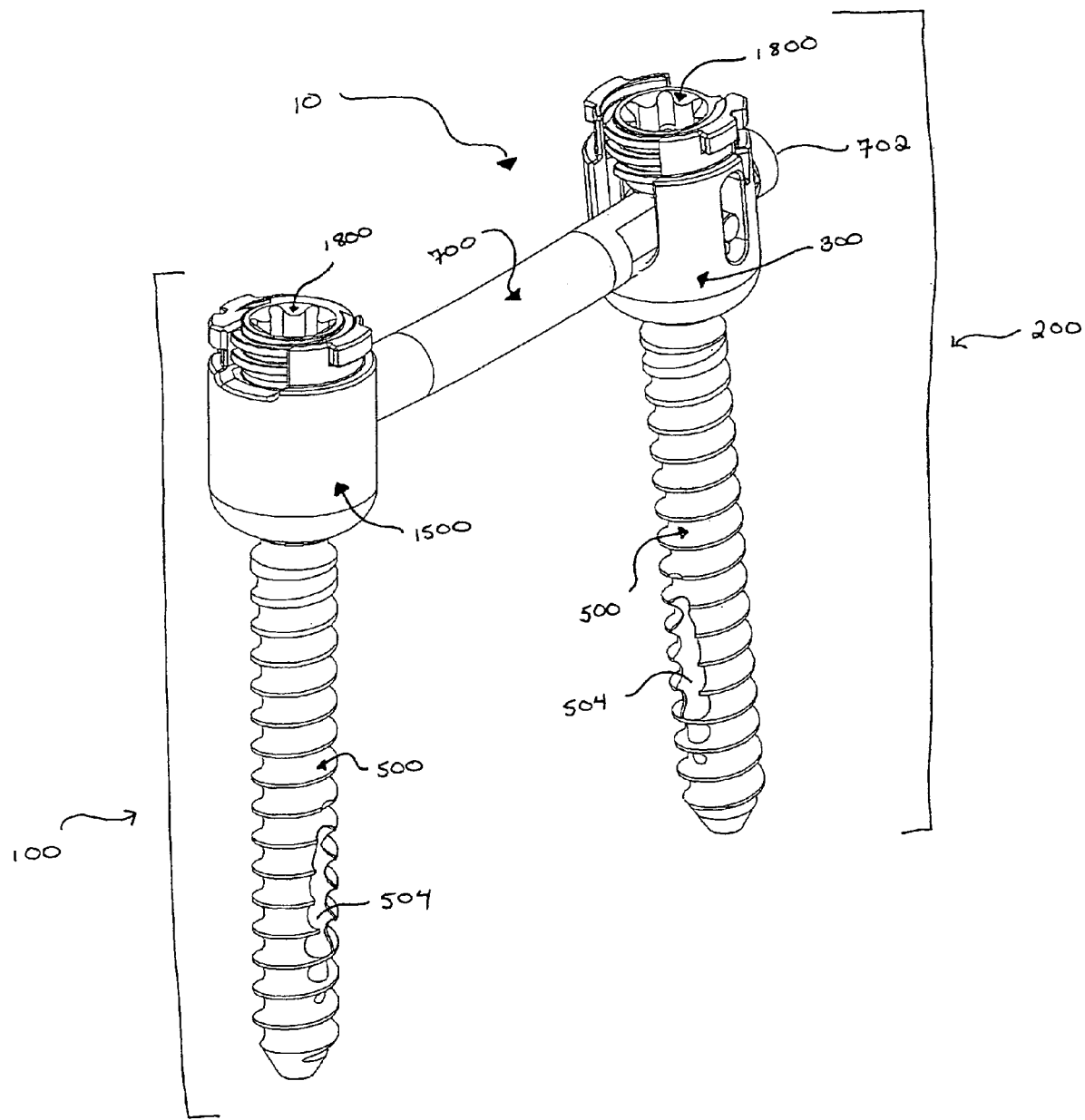
FIG. 1 is a perspective view of an embodiment of an internal stabilization system in accordance with the present invention.

FIG. 1 shows stabilization assembly 10 which includes poly-axial head assemblies 100 and 200 shown interconnected by rod 700. Rod 700 is shown fastened securely to assemblies 100 and 200 by locking caps 1800. As described above, poly-axial rod capturing assembly 100 is anchored in the patient's pedicle by anchor 500 along a guide wire which passes through off axis screw guide 504 in anchor 500. When assembly 100 is positioned, a measurement is taken to the pedicle where the second assembly is to be positioned. This measurement determines the length of rod 700. The polyaxial rod-assembly 200 with proper size rod 700 is chosen and assembly 200, with anchor 500 attached to head 300, is positioned in the selected other pedicle with torque being applied to anchor 500 through drive mechanism in distal end 702 of rod 700 which, at that point, is in-line with the longitudinal axis of assembly 200. From the in-line position, rod 700 is rotated such that it has and end captured by poly-axial rod-capturing head 1500.

While stabilization assembly 10 is shown connected by rod 700, any type of connector for connecting anchor assemblies 100 and 200 could be used and is within the scope of the present invention. Such connectors could include any rod, implant, fastener, or brace used for the purpose of connecting anchors mounted in bony structures. Further such connectors may be rigid, as rod 700, may be elastic, as bands, cables or artificial ligaments, or may be dynamic such as the dynamic brace described in U.S. patent application, Ser. No. 10/914, 751 filed Aug. 9, 2004 and entitled SYSTEM AND METHOD FOR DYNAMIC SKELETAL STABILIZATION, which is herein incorporated by reference.

Figure 2:
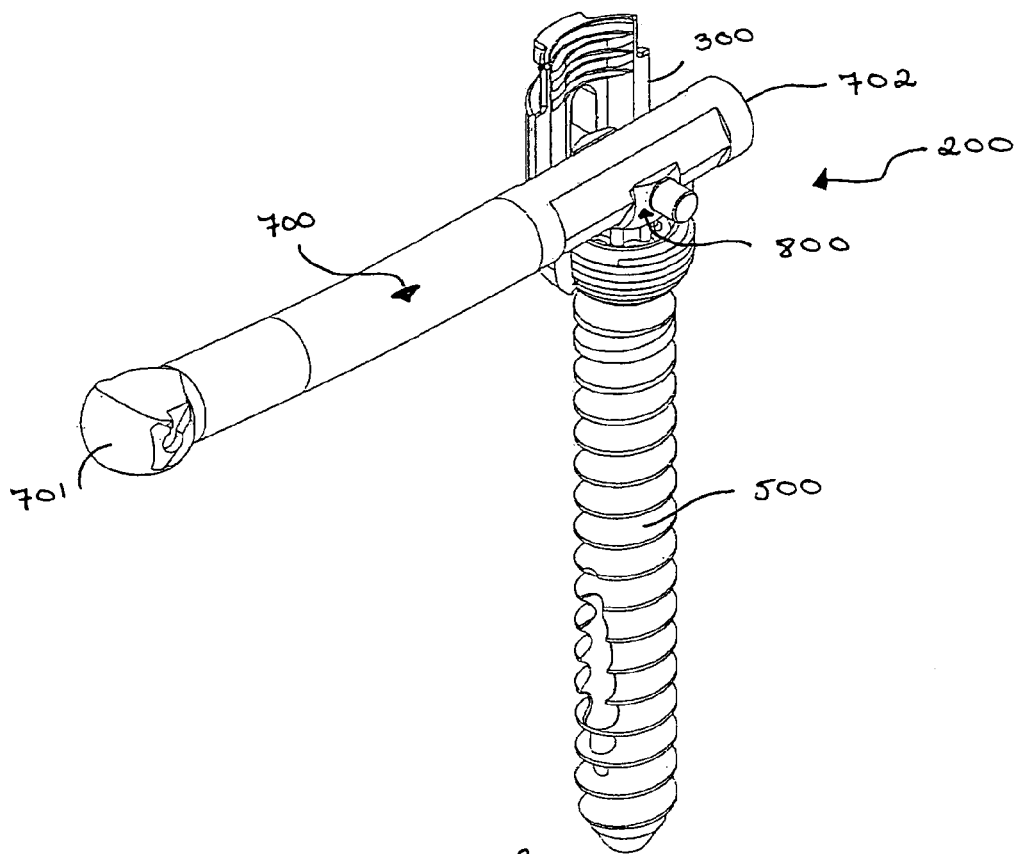
FIG. 2 is a perspective view showing a cut-away of the head holding the rod from FIG. 1.

FIG. 2 shows assembly 200 and it has poly-axial head 300, anchor 500, rod 700 and slide ring 800. Slide ring 800 allows rod 700 to translate in position so that proximal end 701 can be carefully adjusted to fit into poly-axial rod capturing head 1500 of assembly 100 as shown in FIG. 1. Rod 700 includes a distal end 702 with a drive mechanism, and a proximal end 701 shaped such that is can be captured by poly-axial rod-capturing head 1500 shown in FIG. 1.

Figure 3:
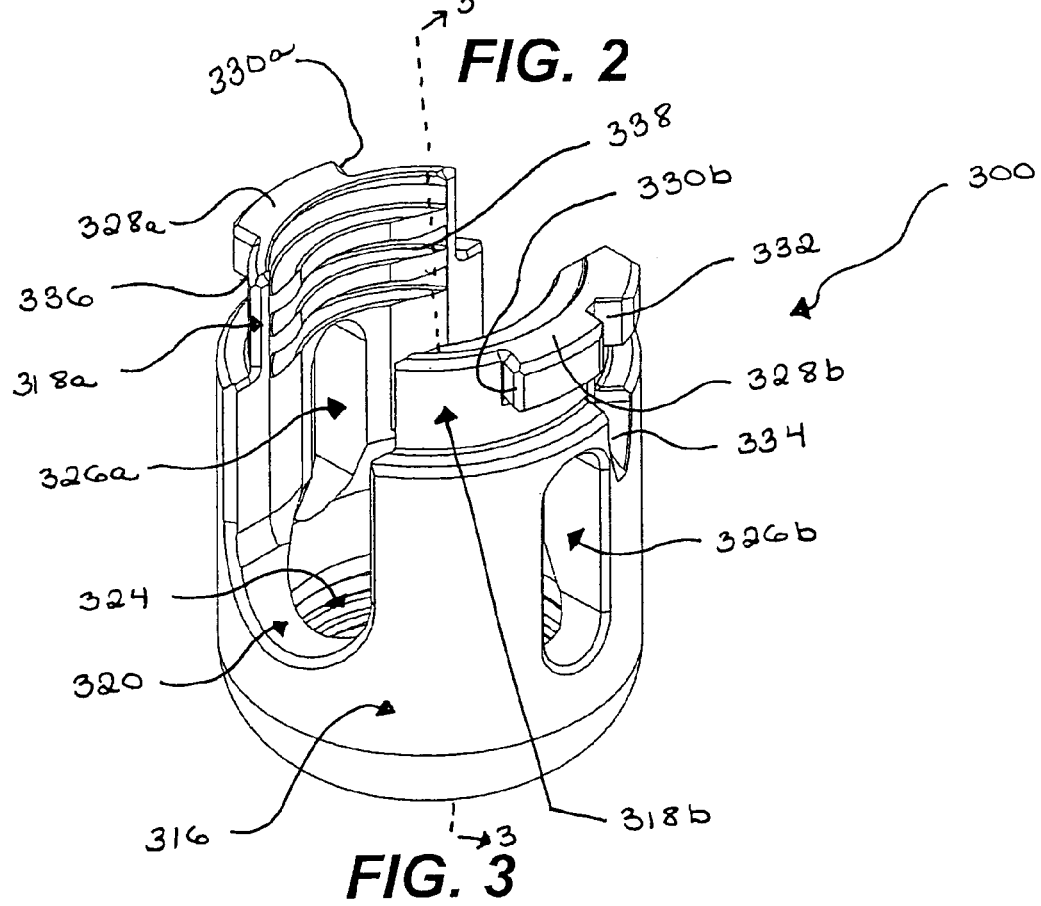
FIG. 3 is a perspective view of the head shown in FIG. 2.

FIG. 3 shows poly-axial rod-assembly head 300 having main body 316 and arms 318a and 318b. Arms 318a, b are created by channel 320 on the center line of poly-axial head 300. A bore extends through the longitudinal center line of poly-axial head 300 and the bore has a spherical portion having threads 324 cut therein. As will be seen with reference to FIGS. 10a and 10b, the spherical portion allows the head to rotate about the top of a bone anchor while threads 324 allow head 300 to gain access to, and interconnect to the head of the bone screw.

Head 300 also has channels 326a and 326b in opposing arms 318a, b, which arms receive slide ring pins of bracket 800 as will be described. Head 300 also has machined surfaces 328a and 328b. These surfaces allow for locking onto a guide tip or extensions to be described hereinafter. Surfaces 328a, b have torquing surfaces 330a and 330b for locking purposes, also to be described hereinafter. Arm 318b also has cuts 332 and 334, which accept locking member 3700, shown in FIG. 37 to enable locking of extensions to head 300 as will be described in greater detail with reference to FIGS. 30-32. Machined surface 328a also includes a recessed area 336 which is positioned as a keyway to allow an extension to be locked onto head 300 in only one direction. Therefore surface 336 is constructed only on surface 328a and not on surface 328b. Head 300 also includes screw threads 338 for receiving locking cap 1800 of FIG. 18.

FIG. 4 shows a sectional view of FIG. 3 taken along line 3-3, and illustrates spherical portion 350 with threads 324, and cylindrical portion 352 formed by interior wall 401. Spherical portion 350 with threads 324 allow the threaded portion of anchor 500 from FIGS. 1 and 5, to be threaded onto head 300. When anchor 500 is threaded beyond threads 324, the threaded portion of anchor 500 becomes captured in cylindrical portion 352, thereby allowing anchor 500 to move in relation to head 300 up to a 30° angle from the center line, which translates into 60 degrees of conical freedom. While 60 degrees of conical freedom is described with reference to the preferred embodiment, any amount of poly axial movement is well within the scope of the present invention.

FIG. 5 illustrates anchor 500, which in this embodiment is a screw having threads 506 which are inserted into the pedicle or other bony structure. While anchor 500 is shown as a screw, any other type of anchor that could be inserted into a pedicle of a vertebra is within the scope of the present invention. Anchor 500 also includes screw threads 501 which thread in the opposite direction from threads 506 for attaching anchor 500 to head 300 shown in FIG. 4. Anchor 500 also includes a torque transfer drive mechanism 505, which mates with torque transfer drive 706 shown in FIG. 7, used in driving anchor 500 into the pedicle of the spine. Anchor 500 also includes stop limiting collar 502, which is slightly larger in diameter then spherical portion 350 of head 300 shown in FIG. 4, allowing head 510 with threads 501 of anchor 500 to be movably held by cylindrical portion 352 of head 300, thereby allowing rotation of head 300 in relation to anchor 500.

As discussed, anchor 500 also includes threads 506 which are bone threads used to purchase anchor 500 into a pedicle. Included near the distal end of anchor 500 is off-axis screw guide 504, which is a cylindrical bore passing through the treads 506 of anchor 500 and out tip 512. This bore is used to pass anchor 500 down a guide wire to direct the anchor into a pre-tapped hole in the pedicle as discussed.

FIG. 6 is a cross-section of anchor 500 showing off-axis screw guide 504. This channel, at its distal end 601, receives a guide wire, the end of which is positioned within the tapped hole in the bone. The screw is passed down the guide wire until distal end 601 enters the tapped hole in the pedicle. Off-axis screw guide 504 is at angle alpha from the center line of anchor 500. Alpha can be any small angle, but is preferably in the range of 10°-15°. As a bore, or cannulation, through the entire screw, as is commonly practiced in the industry, weakens the screw and limits the size of guide wire that can be employed, the off-axis screw guide 504, allows for the benefit of placing the screw in the tapped hole using a guide wire, while preserving the strength of a non-cannulated screw. After the screw has been delivered, the guide wire is removed and the screw can then be screwed into the pre-tapped hole in the pedicle.

Figure 7:
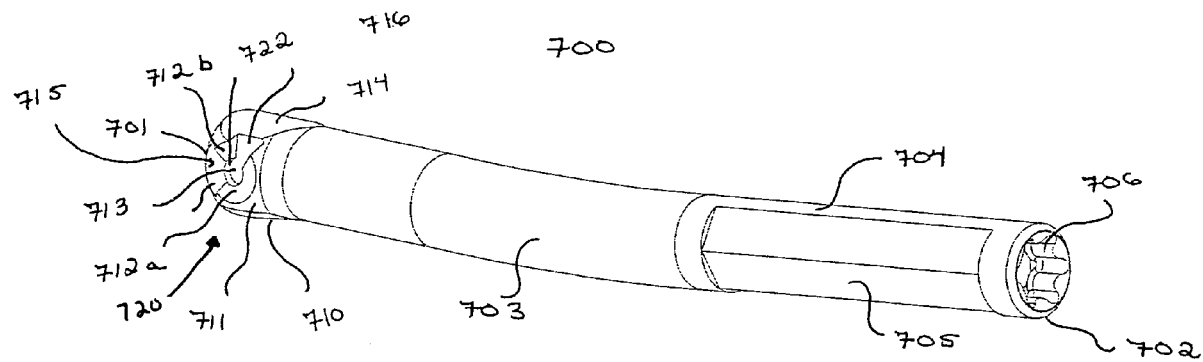
FIG. 7 is a perspective view of the rod from FIG. 1 showing the distal end with a drive mechanism.

FIG. 6 also illustrates drive mechanism 505 for engagement by drive surfaces of tightening tools, such as the drive tool shown in FIG. 52 or the drive mechanism of rod 700 shown in FIG. 7, for driving anchor 500 into the bone. Stop limiting collar 502 allows a mated head, such as poly-axial rod-assembly head 300 from FIG. 3 or poly-axial rod-capturing head 1500 from FIG. 15, to have a poly-axial motion with respect to anchor 500.

As discussed above, to create a tapped hole in a pedicle, the surgeon inserts a bone biopsy needle into the bone. Then the top portion of the bone biopsy needle is removed and pulled out leaving a cannula (an open tube) extending from outside the patient down to the newly created hole in the bone. A guide wire, which can have a diameter on the order of two millimeters, is passed down inside the cannula and over the guide wire and dilators are sent down to create a passageway between the muscle tissue.

Next, the anchor, or bone screw, must be inserted into the hole. Typically, a cannulated screw is used with a hole all the way through the longitudinal axis. Because some of the screws an be as small as 5.5 millimeters on the major diameter, the minor diameter is extremely small. Consequently, only a very small hole will work because otherwise the screw loses strength. Thus, the holes tend to be small, on the order of 1 millimeter. However, even with a cannulation of 1 millimeter the screws may break, either as a result of misplacement, or when they are used on heavy or active patients. Also, a small cannulation diameter requires a small guide wire, which in turn creates several problems for the surgeon. Small wires can kink, or become bent, or get caught when the screw is being advanced.

When a guide wire is caught inside a screw it begins to advance with the screw and can move beyond the plane of the vertebral body thereby puncturing through the anterior portion of the vertebral body causing trauma to the soft tissue and vessels anterior to the vertebral body. The anchor of the present invention, which is formed with the off-axis screw guide, together with a cannula with a groove down its entire length allows the guide wire to remain outside the cannula while the screw is within the cannula. This allows for much thicker guide wires to be used, for example 2 millimeters in diameter, without sacrificing the strength of the screw or having guide wire issues of kinking or wire advancement while the screw is being positioned.

Figure 8:
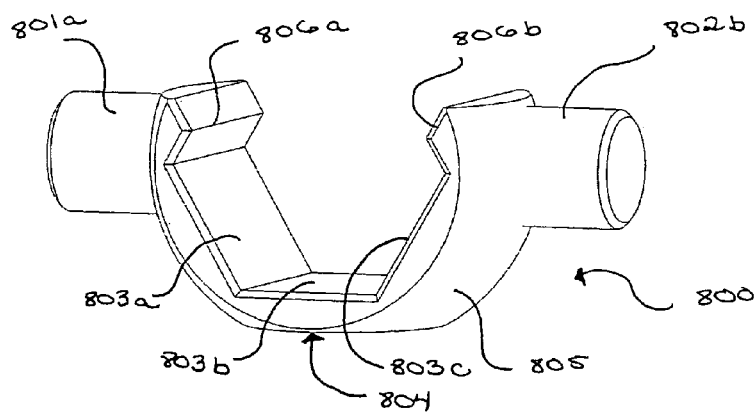
FIG. 8 is a perspective view of an embodiment of the slide ring from FIG. 1.
Figure 12:
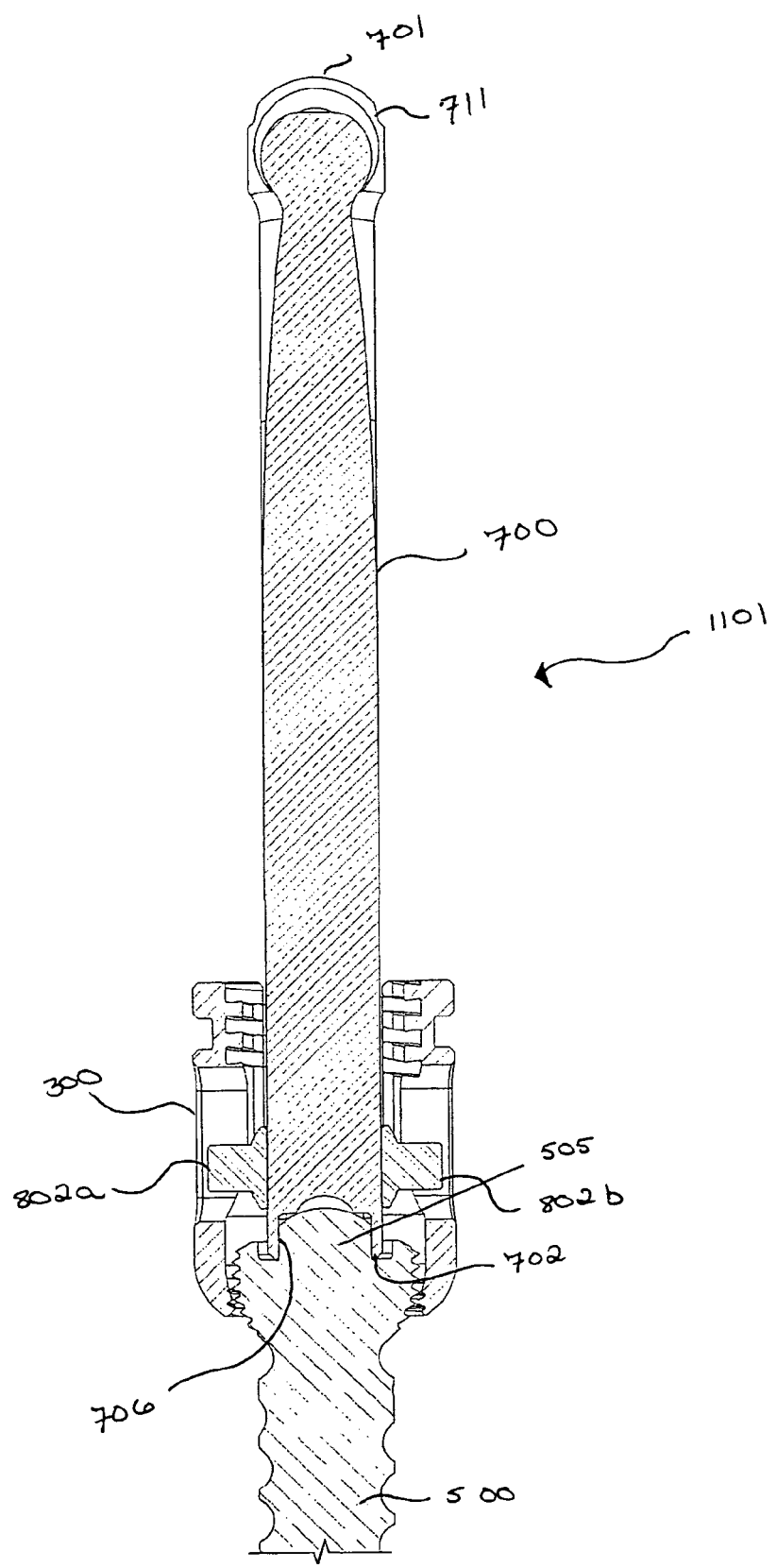
FIG. 12 is a cross-sectional view of FIG. 11.

FIG. 7 illustrates rod 700 which has distal end 702 in which drive mechanism 706 is positioned. Drive mechanism 706 mates with drive mechanism 505 as shown in FIG. 12. Rod 700 also includes rod curved body portion 703 in which the rod is partially curved to conform to a patient. Sliding surfaces 705 are constructed to engage with slide ring 800 (FIG. 8).

Figure 11:
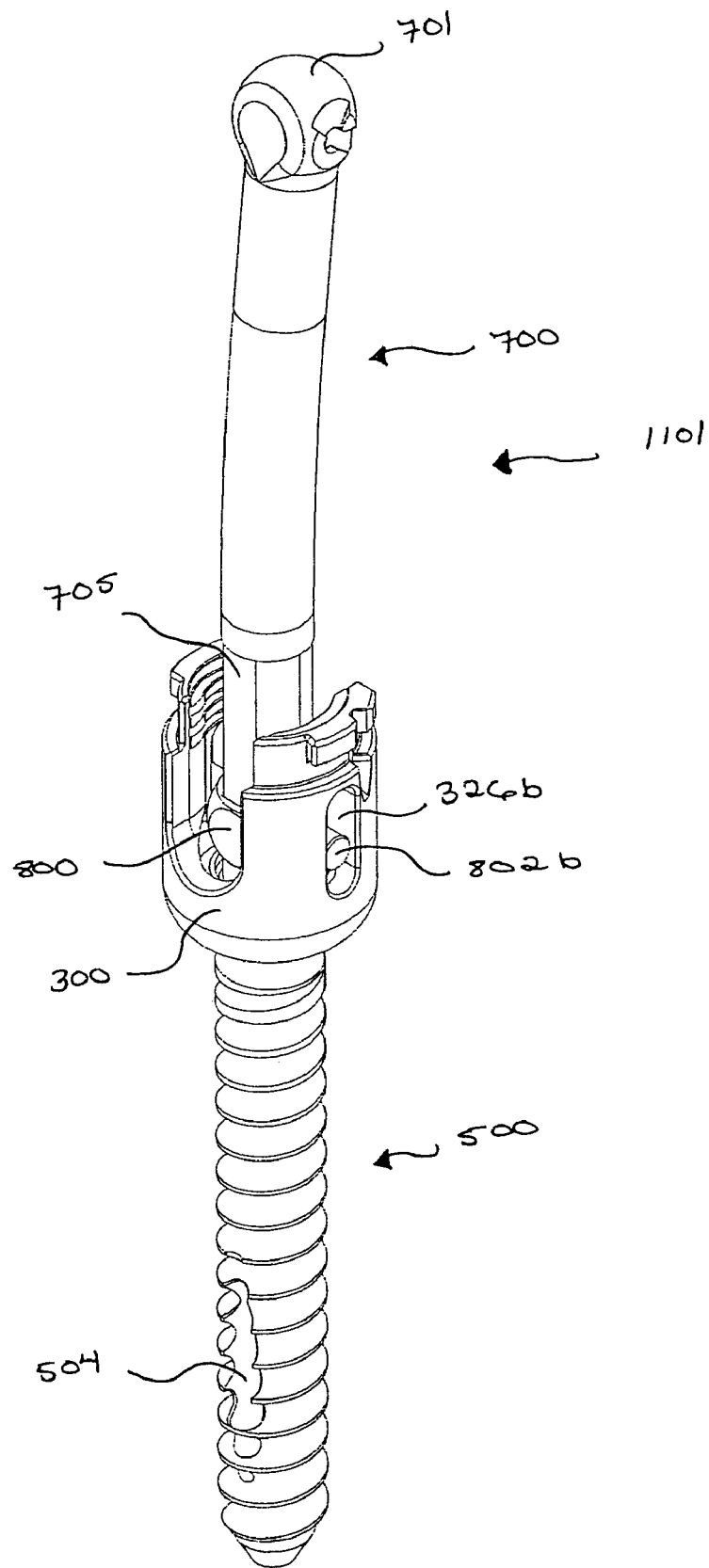
FIG. 11 is a perspective view of the rod and anchor assembly of FIG. 10A mounted with the head of FIG. 3.
Figure 15:
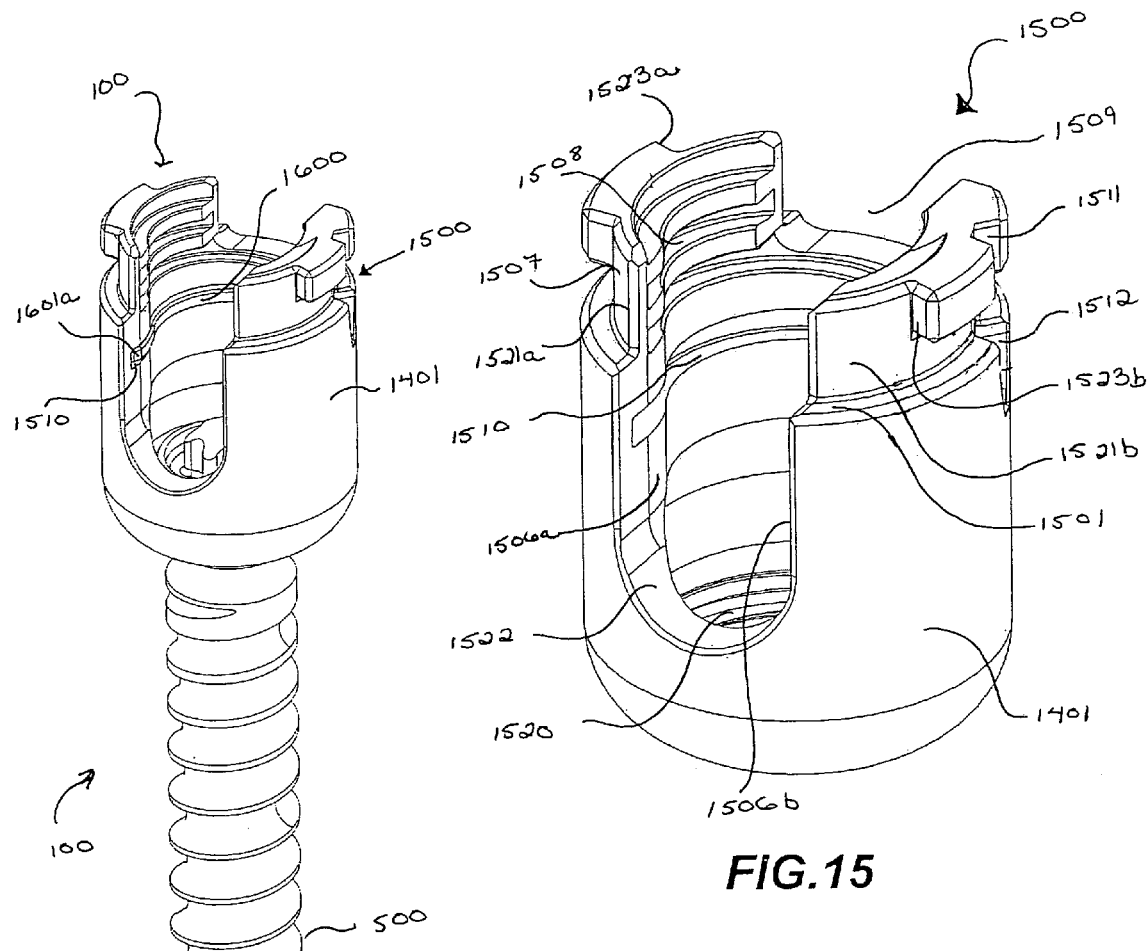
FIG. 15 is a detailed perspective view of the capturing head of FIG. 14.
Figures 48, 49:
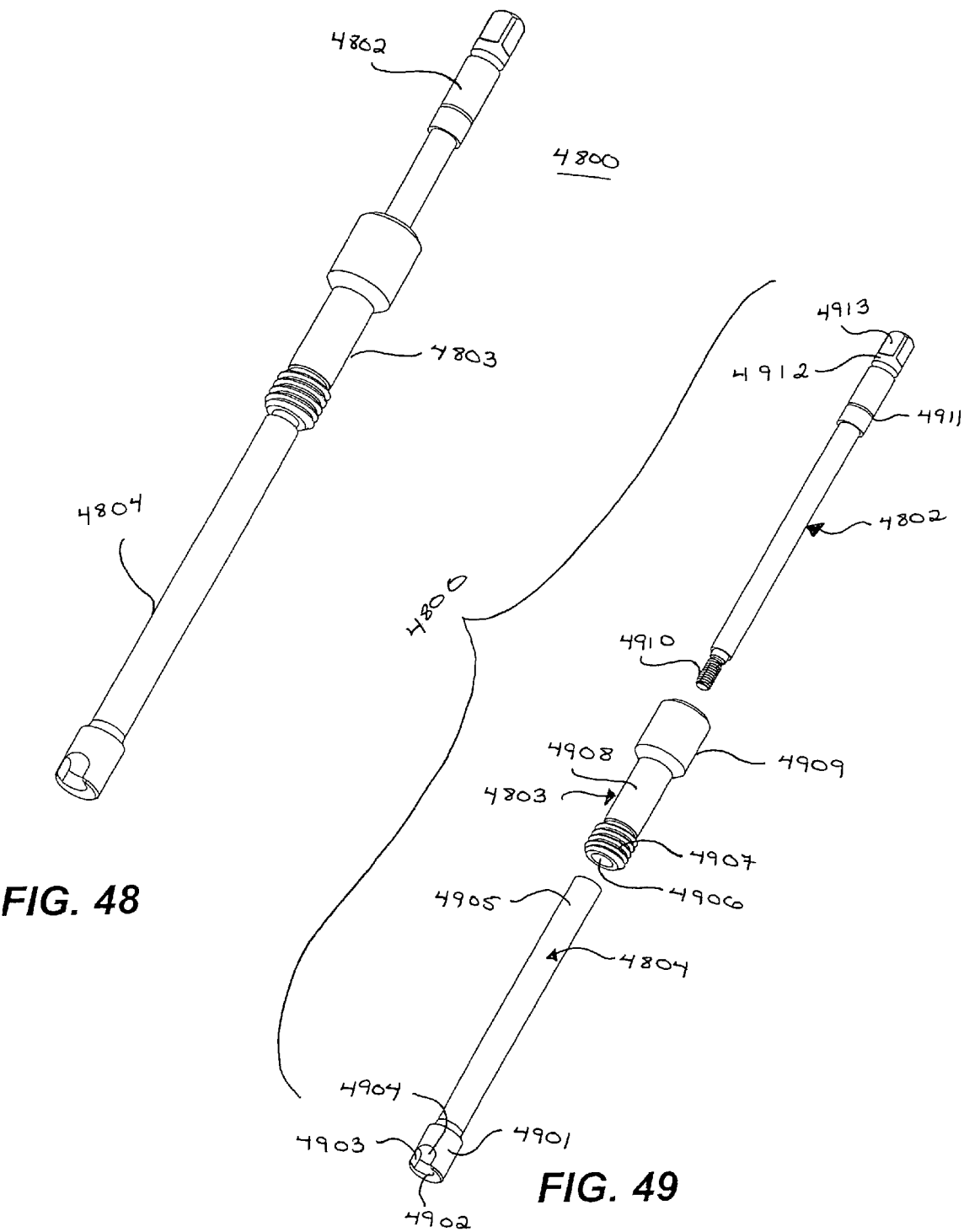
FIG. 48 is a perspective view of a driver in accordance with the present invention.
FIG. 49 is an exploded view of the driver of FIG. 48.

Proximal end 701 of rod 700 must accomplish at least two functions, first driving the rod/poly-axial head assembly as an extension of a driver, such as the one shown in FIG. 48, and second being captured by poly-axial rod-capturing assembly 1500 shown in FIG. 15, which allows for the repositioning of rod 700 from the in-line position shown in FIG. 11 to the "horizontal" position for mating with assembly 100 as shown in FIG. 1. Specifically, rod 700 has driving surface 710 to engage a special head of the driving tool shown as head 4901 in FIG. 49. Driving surface 710 engages with the head of the driving tool and allows torque to be transferred from the driving tool through rod 700 and into anchor 500 which is then screwed into a pedicle or other bony structure. Opposing drive surface 710 is locking surface 714 which is designed to engage with the bottom surface of locking cap 1800 from FIG. 18. The locking of rod 700 using locking caps 1800 will be discussed in greater detail with reference to FIGS. 22 and 23

Proximal end 701 of rod 700 also includes spherical portion 711 having a diameter larger than the diameter of rod 700 for the purposes of allowing the cavity of poly-axial rod-capturing head 1500 (FIG. 15) to capture rod 700 and to keep the spherical portion 711 engaged with head 1500 as will be discussed with greater detail with respect to FIG. 15.

Figure 57:
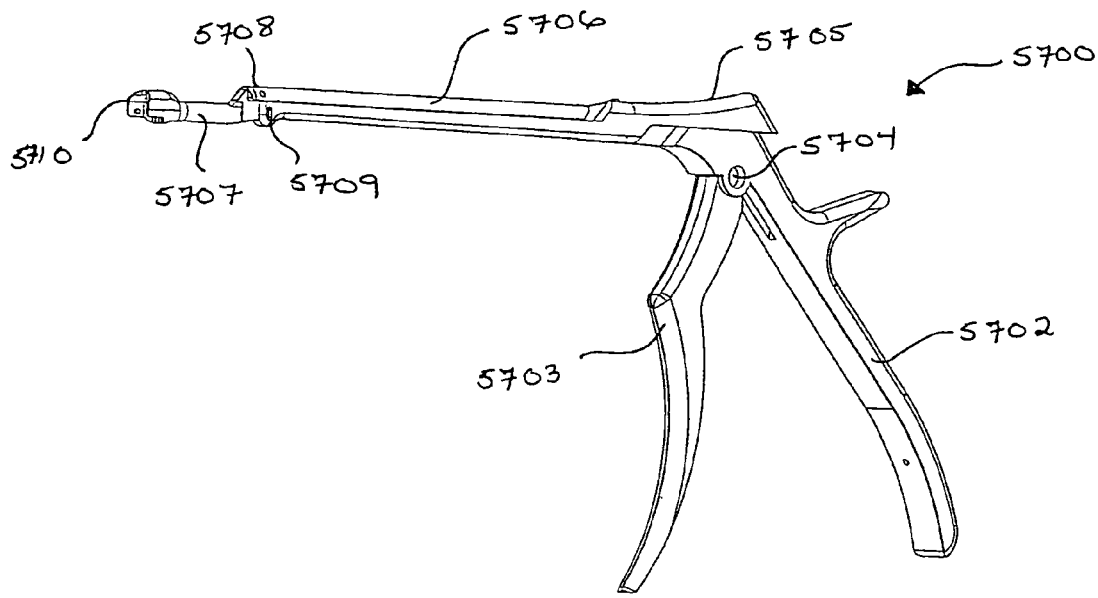
FIG. 57 is a perspective view of a rod transfer tool in accordance with the present invention.

Proximal end of rod 700 must also be capable of being captured by rod transfer tool 5700 shown in FIG. 57, such that the rod transfer tool is engaged with rod 700 until it is nearing the horizontal position at which point rod 700 must disengage from the rod transfer tool so that it may be engaged with the poly-axial rod-capturing head. Rod transfer tool engagement mechanism 720, which is duplicated on the opposing side of spherical portion 711 includes ramp 715 which allows tines 5905*a* and *b* from FIG. 59 of the rod transfer tool to slide up, over lip 722, and into recess 713, thereby engaging end 701 with the rod transfer tool until tines 5905*a* and *b* of rod transfer tool 5700 are turned to the point that they can slide out of exit ramp 716, which controls the release of the tine from end 701. While engaged in recess 713, tines 5905*a* and *b* are free to rotate about an axis normal to flats 712*a* and 712*b*.

As the tool pushes on proximal end 701, that end rotates toward assembly 100 (FIG. 1) until end 701 of rod 700 is in position to be captured by head 1500. At that point, the angle of rod 700 with the pushing instrument is such that the tines of the instrument are pushed out of cylindrical recess 713 and out through exit ramp 716 thereby releasing proximal end 701 to be engaged into head 1500. The operation of rod transfer engagement mechanism, along with the distal end of the rod transfer tool of FIG. 57 will be discussed with greater detail with reference to FIGS. 63 and 65*a*.

Once engaged with both heads 300 and 1500, locking caps can be inserted into each of heads 300 and 1500, such that the ends of the locking caps are engaged with locking surfaces 714 and 704. Locking surfaces 714 and 704 are preferably curved to have locking cap 1800, shown in FIG. 18, not force rod 700 into a position that is normal to the bottom of the locking cap, but rather a position that allows rod 700 to assume its natural rotation. Thereby allowing for installation of the rod in positions that accounts for variations in anatomical positioning of the vertebral bodies.

FIG. 8 illustrates slide ring 800 which includes main body cylindrical portion 805, and extension dog-ear tines 802*a* and 802*b*. Dog-ear tines 802*a*, and b allow rod 700 to register with racetrack openings 326*a*, *b* of head 300 as shown in FIG. 3. This facilitates up-down movement of rod 700 with respect to assembly 200 (FIG. 1). This then allows for a variation in height of the rod to occur when the rod is in process of being translated from an in-line position to an approximately 90 degree position for engaging rod-capturing assembly 100.

Also, as shown in FIG. 8, slide ring 800 includes a portion having flats 803*a*, 803*b* and 803*c* and partial flats 806*a* and 806*b* forming a hexagonal saddle in which sliding surfaces 705 rest. While a hexagonal saddle is shown, any shape of saddle may be used that captures rod 700 in a manner that prevents rotation of rod 700 within the slide ring and allows rod 700 to slide freely therein. As stated, these surfaces are constructed to allow slide ring 800 to mate with flats 705 of rod 700 and to allow rod 700 to slide in head 300 while being held by slide ring 800 which in turn is held by ears 802*a* and 802*b* inside openings 326*a* and 326*b*, respectively, of head 300. Surface 804 is used to contact anchor 500 from FIG. 5 during the locking of the poly-axial head assembly, which will be discussed in greater detail with reference to FIG. 22*a*

Figure 9:
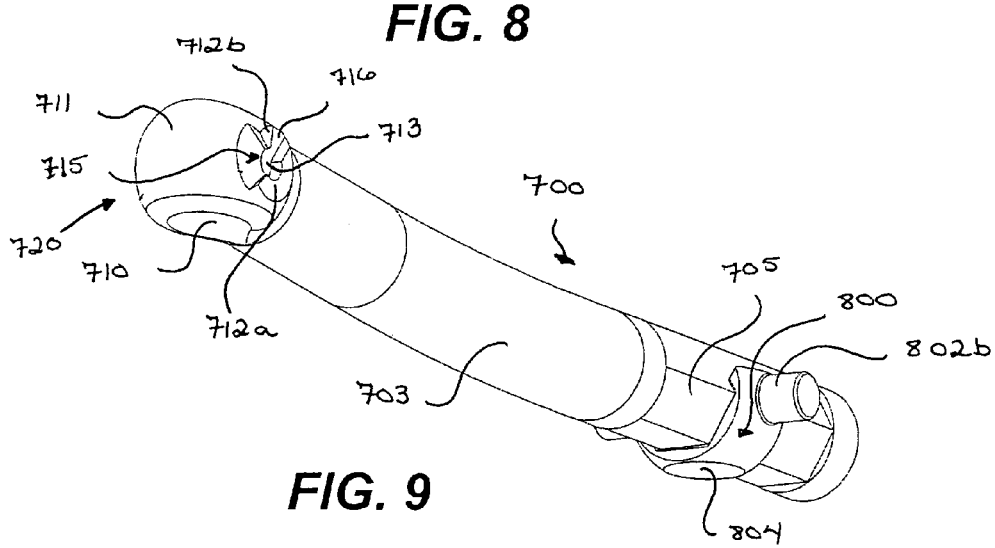
FIG. 9 is a perspective view of the rod of FIG. 7 mated with the slide ring of FIG. 8.

FIG. 9 shows rod 700 mated with slide ring 800 which allows rod 700 to move laterally with respect to slide ring 800. The preferred distance of such movement, approximately 1 centimeter of translation, is allowed along track 705. For multilevel procedures, discussed with reference FIGS. 67-77, approximately 15 millimeters of translation is required.

Figure 18:
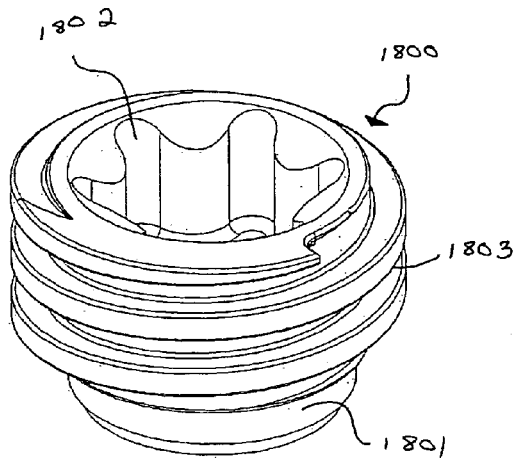
FIG. 18 is a perspective view of a locking cap according to the present invention.

FIGS. 10*a* and *b* show the mating of head 300 with anchor 500, with the following description applying also to the mating of head 1500 from FIG. 15 with anchor 500. Anchor 500 has stop limiting collar 502 and threads 501. As threads 324 in spherical portion 350 of head 300 advance beyond threads 501, spherical portion 510 of anchor 500 becomes captured by cylindrical portion 352 of head 300. This allows angulation, shown in FIG. 10*b*, between head 300 and anchor 500 with the preferred angulation to be about 30 degrees from centerline, yielding 60 degrees conical motion. An interesting feature to note is that screw threads 501 of anchor 500 and screw threads 324 of spherical portion 350 essentially bind creating a cold weld type of mate when pressure is applied from the top in an axial direction through the rod and slide ring to drive 505, such as when locking cap 1800 from FIG. 18 is tightened into head 300.

FIG. 11 shows a complete poly-axial rod assembly 1101 formed by anchor 500 mated with poly-axial rod assembly head 300 which is in turn holding rod 700, where rod 700 is shown in its in-line orientation with anchor 500.

FIG. 12 is a cross-sectional view of FIG. 11 showing that in the in-line orientation, drive mechanism 706 of the rod 700 is mated with drive mechanism 505 of anchor 500, such that assembly 1101 is ready to be delivered into the pedicle as discussed above.

Figure 13:
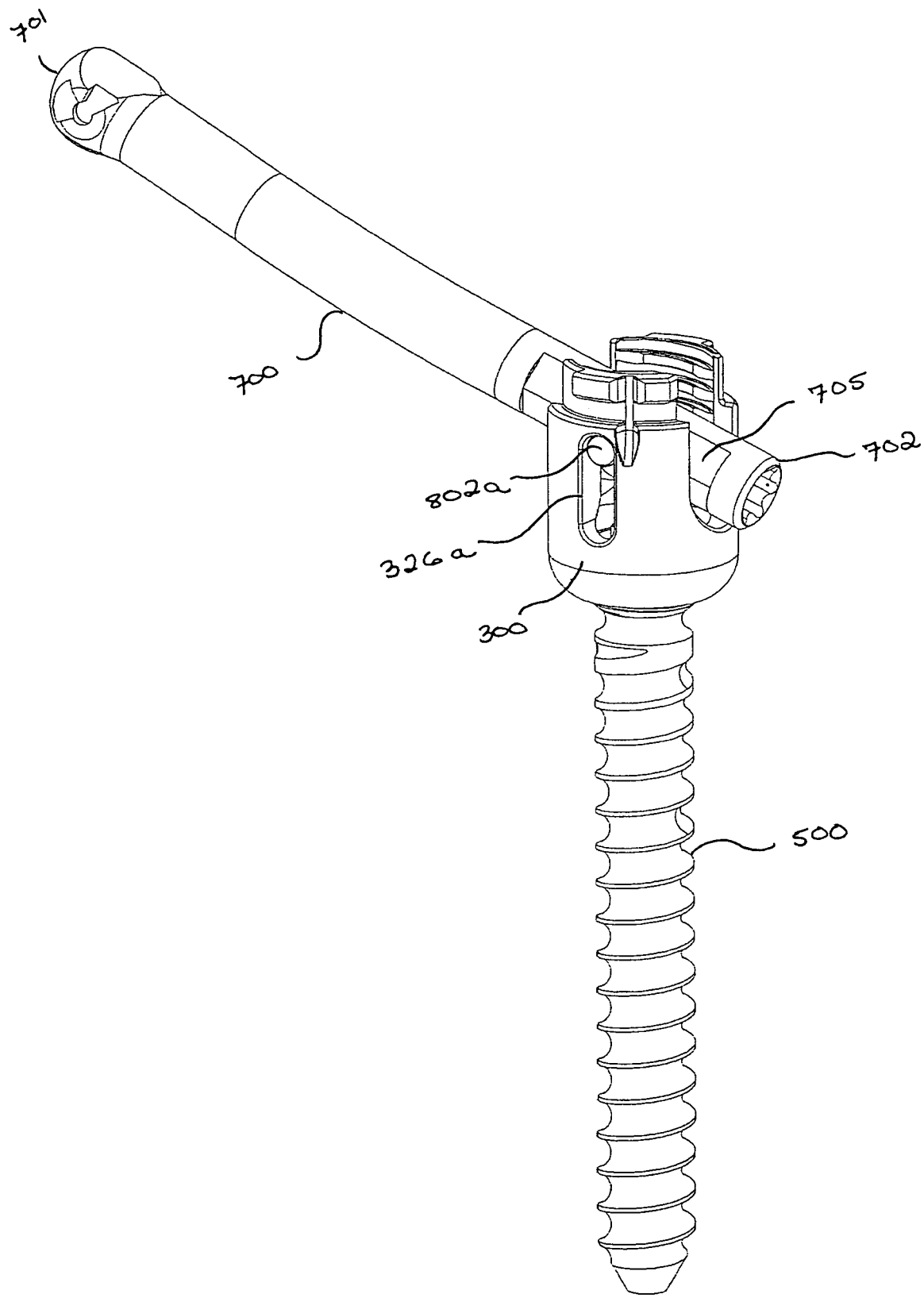
FIG. 13 is a perspective view of the rod, anchor and head assembly of FIG. 11 where the drive mechanism of the rod has been disengaged from the anchor and rotated within the head.

FIG. 13 shows rod 700 in the process of being translated from the in-line orientation such as would occur when rod 700 is being rotated for mating with a rod-capturing head assembly (not shown). The procedure and tool used for this translation will be described hereinafter. Note that during this translation, ears 802*a* and 802*b* (not shown) move upward in opening 326*a* while rod 700 is free to move laterally with respect to head 300 via flats 705 riding in the slide ring.

Figures 14, 16:
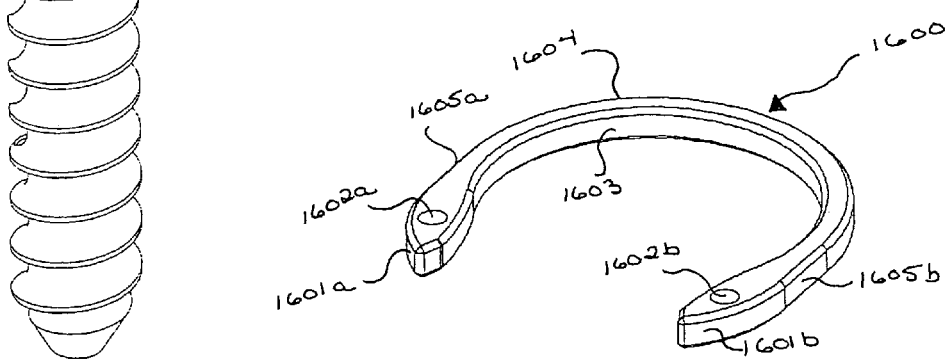
FIG. 14 is a perspective view of an embodiment of a capturing head mounted to an anchor in accordance with the present invention.
FIG. 16 is a perspective view of an embodiment of a clip ring used with the capturing head of FIG. 15.

FIG. 14 shows a poly-axial rod-capturing assembly 100 having rod-capturing head 1500 positioned on anchor 500. Clip ring 1600 is shown positioned in groove 1510 constructed on the inside face of body 1401. Ring 1600 opens by moving backwards as force is applied to it by mating end 701 of rod 700 (not shown). Once end 701 passes into housing 1401, ring 1600 resumes its normal dimensions thereby preventing rod end 701 from coming out of body 1401 resulting in rod end 701 being captured by head 1500. The force required to deform ring 1600 and the returning of ring 1600 back to its original position yields a tactile as well as audible sensation which can be felt and heard by the surgeon performing the procedure, allowing the surgeon to know that the rod has be placed in the proper position in head 1500. Note that the back wall of clip ring groove 1510 is of a greater diameter than outer diameter 1604, shown in FIG. 16, of clip ring 1600. Therefore, clip ring groove 1510 has room to allow for the expansion of clip ring 1600 into the groove to allow spherical portion 711 of rod 700 from FIG. 7 to pass by clip ring 1600.

FIG. 15 shows head 1500 having threaded spherical portion 1520 for mating with anchor 500 as discussed above with respect to head 300. Reduced area 1521*a* and 1521*b* form a groove with ledge 1501 acting as a stop. This grove accepts an extension, such as the extension shown in FIG. 30-32. Body 1401 includes a horseshoe opening 1522 and interior surfaces 1506*a* and 1506*b*. Horseshoe opening 1522 is sized to accept body 703 of rod 700 from FIG. 7, while being smaller than spherical portion 711 of rod 700, preventing rod 700 from pulling out of head 1500.

Above surface 1501 there are two arms, 1521*a* and 1521*b*. Arms 1521*a* and 1521*b* include torquing surfaces 1523*a* and 1523*b* which allow delivery of a counter-torque when held by a tool as will be described with reference to FIG. 66*a*. When final tightening is given to locking cap 1800, surfaces 1523*a* and 1523*b* mate with the tool as will be described. Key way 1507 allows for uni-directional assembly of head 1500 on the extension insuring proper orientation of the extension in relation to head 1500. Threads 1508 are designed to receive locking cap 1800. On the far side of housing 1401 channel 1509 allows for assembly of the extension. Slots 1511 and 1512 are positioned on arm 1521*b* to accept a locking slider, described with reference to FIGS. 30 and 37 from the extension.

FIG. 16 illustrates clip ring 1600 that mates inside clip ring groove 1510 of head 1500 as discussed. Clip ring 1600 has an outer diameter 1604 and an inner diameter 1603 and keeping arms 1601*a* and 1601*b*. These keeping arms have flat surfaces 1605 *a, b* for preventing rotation of the clip ring in the groove. Clip ring 1600 splays apart as the spherical end portion of rod 700 exerts a force on clip ring 1600 as it enters head 1500. When the spherical portion 711 of rod 700 enters head 1500 the spherical portion contacts inner diameter 1603 of clip ring 1600 and requires the expansion of 1601*a* and 1601*b* away from one another to allow the spherical portion to pass. Once that portion has passed, there is a tactile snap that is felt when 1601*a* and 1601*b* return to their proper position. Holes 1602*a* and 1602*b* allow for installation of clip ring 1600 into snap ring groove 1510 of head 1500.

Clip ring 1600 also acts to prevent the spherical portion 711 of rod 700 from passing upward out of head 1500. As mentioned, rod 703 cannot pull out of channel 1522 because channel 1522 has a smaller diameter than does spherical portion 711 of rod 700. The capturing of rod 700 in rod-capturing head 1500 allows the surgeon to then perform other activities that could take many minutes, all while knowing that rod 700 is captured properly, even though locking cup 1800 has not yet been either installed or tightened with the final tightening force. Rod end 701 cannot pull out of head 1500 laterally, nor can it lift vertically. In addition to allowing the surgeon to perform other procedures before locking the assembly, this system allows the rod to be traversed to adjust for a compression or distraction without worry that the rod will become dislodged from head 1500.

Figure 17:
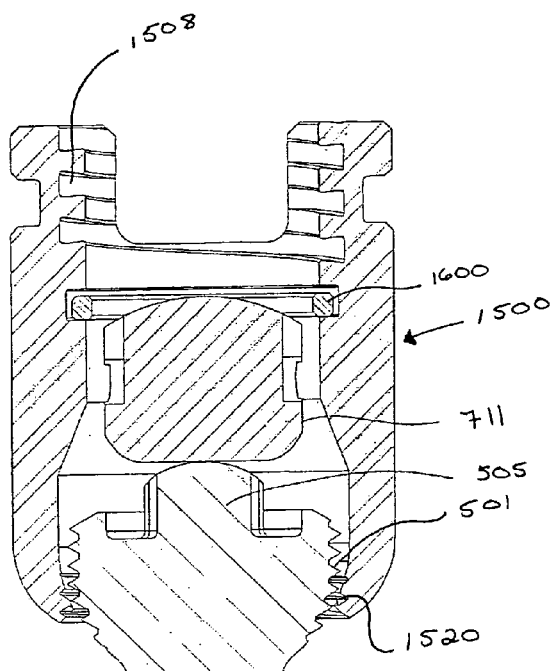
FIG. 17 is a cross-section view of a capturing head mounted on an anchor with a locking cap inserted in the capturing head.

FIG. 17 is a cross-section of screw assembly 100 showing threads 1508 for receiving locking cap 1800 and also showing threads 1520 of head 1500 corresponding to threads 501 of anchor 500. Also the relationship between clip ring 1800, spherical portion 711 of rod 700, and drive mechanism 505 of anchor 500 are shown when rod 700 is in the captured position before locking cap 1800 is installed.

FIG. 18 shows details of locking cap 1800 with threads 1803 for mating with threads 1508 of head 1500 or head 300. Cap 1800 has boss 1801 for applying force to a captured rod. Driving mechanism 1802 for tightening the cap is also shown.

Figure 19:
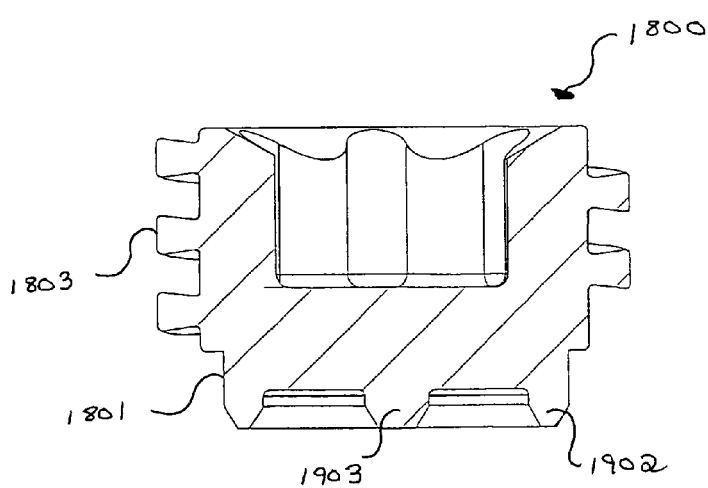
FIG. 19 is a cross-sectional view of the locking cap of FIG. 18.

FIG. 19 is a cross-sectional view of cap 1800 illustrating threads 1803 which can be, for example, the type shown in U.S. application Ser. No. 10/805,967, filed Mar. 22, 2004 and entitled CLOSURE MEMBER FOR A MEDICAL IMPLANT DEVICE, hereby incorporated by reference herein. Also shown are extruded appendages 1902 and 1903 for the purpose of reducing surface area, therefore increasing pressure when locking cap 1800 comes to bear on a rod.

FIG. 20 shows locking cap 1800 screwed into head 1500 such that threads 1803 are mated with threads 1508 of head 1500.

FIG. 21 illustrates the thread interaction of a helical dovetail interlocking thread 2101 as described in the above-mentioned application Ser. No. 10/805,967. Thread 2101 is on cap 1800 while mating threads 2102 is on head 1500 (300). As described in the referenced application, the dovetail threads act to pull the thread of the head inward, instead of acting to place an outward force, causing the walls of the head to splay outwardly as would occur using normally shaped threads.

FIG. 22*a* shows the relationship between rod 700, which is positioned in slide ring 800, both positioned in head 300, locking cap 1800 and anchor 500. Appendage 1903 on locking cap 1800 exerts a force on locking surface 704 of rod 700 when locking cap 1800 is tightened into head 300. Surface 804 of slide ring 800 in turn exerts a force on drive mechanism 505 of anchor 500. The force of tightening locking cap 1800 therefore, exerts the necessary forces on the elements of assembly 200 to hold the elements rigidly in place relative to one another.

FIG. 22*b* similarly shows the relationship between spherical end 711 of rod 700, locking cap 1800 and anchor 500. Appendage 1903 on locking cap 1800 exerts a force on locking surface 714 of rod 700 when locking cap 1800 is tightened into head 1500. Surface 710 of rod 700 in turn exerts a force on drive mechanism 505 of anchor 500. The force of tightening locking cap 1800 therefore, exerts the necessary forces on the elements of assembly 100 to hold the elements rigidly in place relative to one another.

Figure 23:
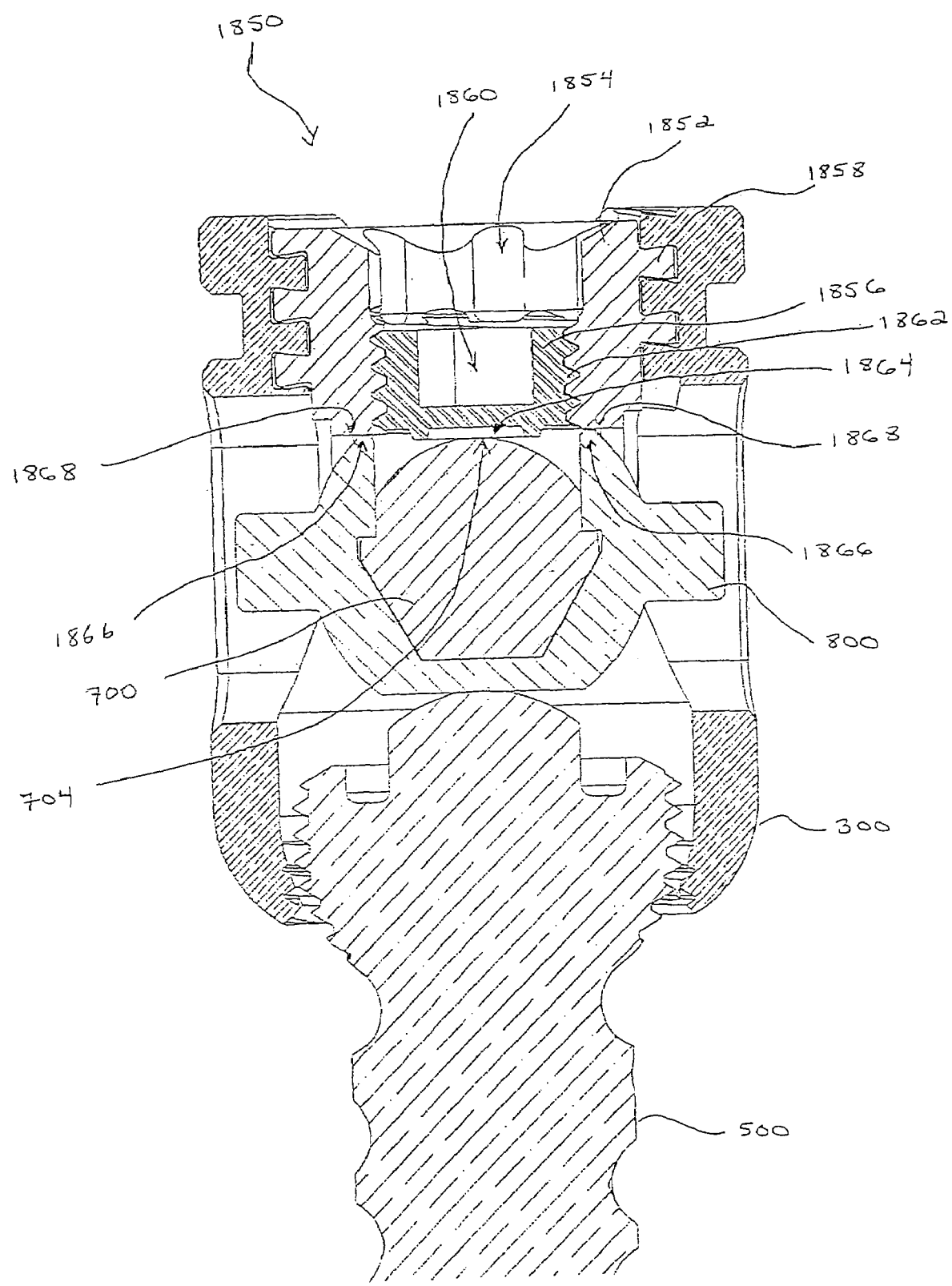
FIG. 23 is a cross sectional assembly showing an alternate embodiment of a locking cap in relation to a poly-axial head, anchor, rod, and slide ring assembly in accordance with the present invention.

FIG. 23 is a cross sectional view showing an alternate embodiment of a locking cap 1850 in relation to rod 700, slide 800, and poly-axial head 300. Where locking cap 1800 of FIG. 18 is a single body which is threaded into a poly-axial head, such as head 300 or head 1500, and engaged surface 704 or 714 on rod 700 from FIG. 7 as appropriate, locking cap 1850 is formed by two distinct elements, namely locking ring 1852 and compression cap 1856. Locking ring 1852 threads into poly-axial head 300, which could also be poly-axial head 1500, by means of threads 1858. Threads 1858 are described in greater detail with reference to FIG. 21. Locking ring 1852 also includes drive mechanism 1854 which accepts a male drive mechanism head such as the one shown in FIG. 66*b* attached to drive shaft 6505. Locking ring 1852 is inserted first, after rod 700 is properly positioned, and acts to compress guide ring 800, through surface 1868 of the locking ring mating with surface 1866 of the slide ring, which in turn causes guide ring 800 to compress anchor 500. This results in immobilizing head 300 relative to anchor 500, eliminating the poly-axial movement of head 300 and anchor 500. Locking ring 1852 locks the head/anchor assembly together but does not compress rod 700 when it is installed allowing the rod to slide in guide ring 800 allowing assemblies 100 and 200 from FIG. 1 to move relative to one another so that the positioning of the entire assembly can be finalized.

Once the positioning of the assemblies is finalized, and any other tasks needed before the rod is compressed and made rigid, are finished, compression cap 1856 can be installed in locking ring 1852. Compression cap 1856 is threaded into locking ring 1852 by means of threads 1862 and drive mechanism 1860. When compression cap is tightened into place, surface 1864 contacts surface 704, or 714 for assembly 100 from FIG. 1, and compresses rod 700, causing rod 700 to lock into place with respect to guide ring 800 and become rigid, or immobile in the same manner described with reference to locking cap 1800 in FIGS. 22a and b.

Locking cap 1850 has advantages over locking cap 1800 in that it allows assembly 100 or 200 to be locked together in two phases instead of the single phase of locking cap 1800. The first phase, the insertion of locking ring 1852, allows the poly-axial motion of the assembly to removed, holding head 300 rigid with respect to anchor 500, but not compressing rod 700 so that rod 700 retains the ability to slide within slide ring 800. The second phase, the installation of the compression cap, compresses rod 700 with slide ring 800, thereby causing them to be held rigidly in place and preventing any further motion with respect to rod 700 and guide ring 800. This two phase approach allows for adjustments to be made while the assemblies are held rigidly in place but rod 700 is still free to slide laterally within guide ring 800, allowing for greater flexibility in the delivery of the stabilization system.

Figure 24:
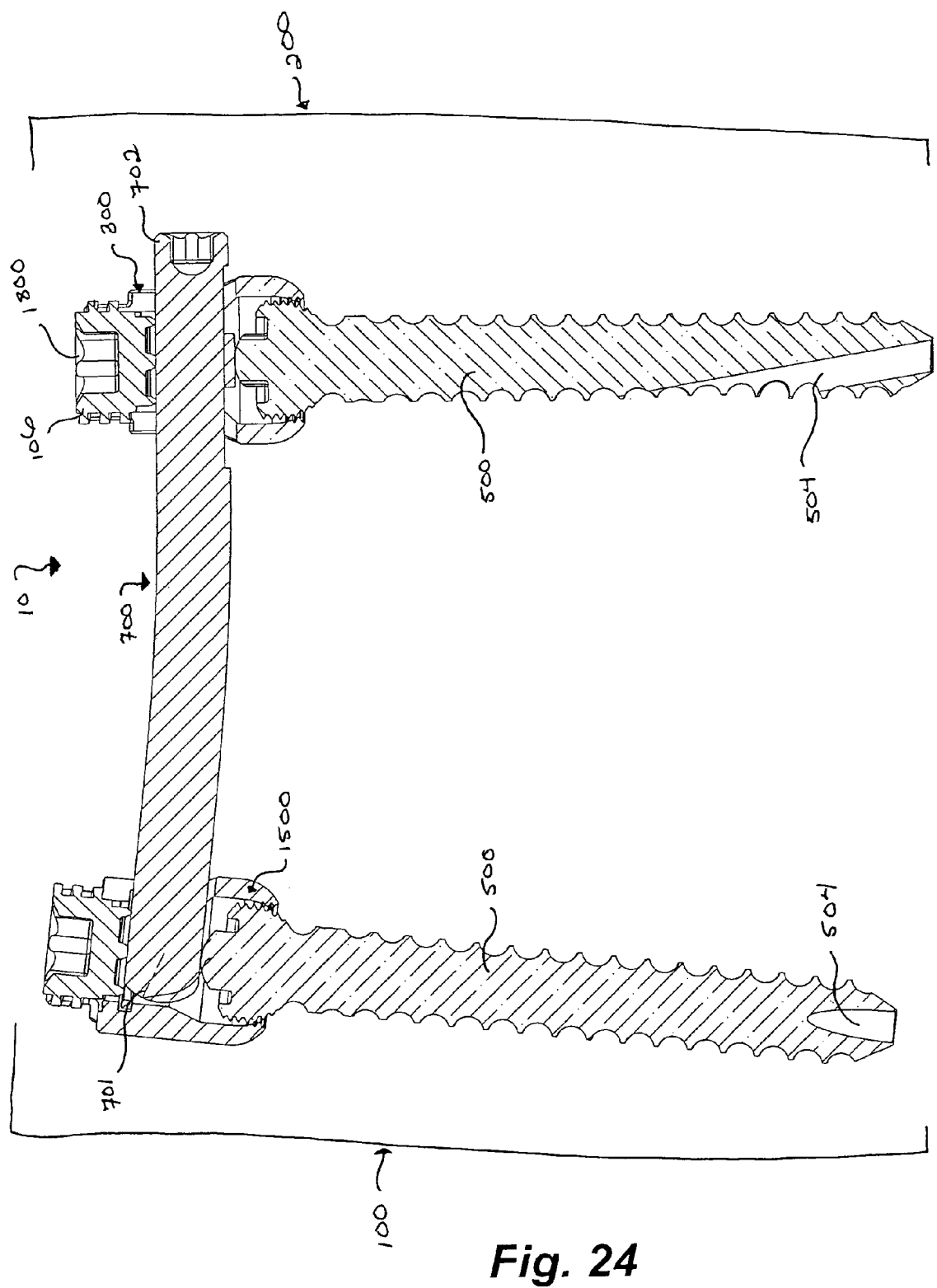
FIG. 24 is a cross-section view of the stabilization system of FIG. 1.

FIG. 24 is a cross-section view of system 10 (FIG. 1).

Figure 25:
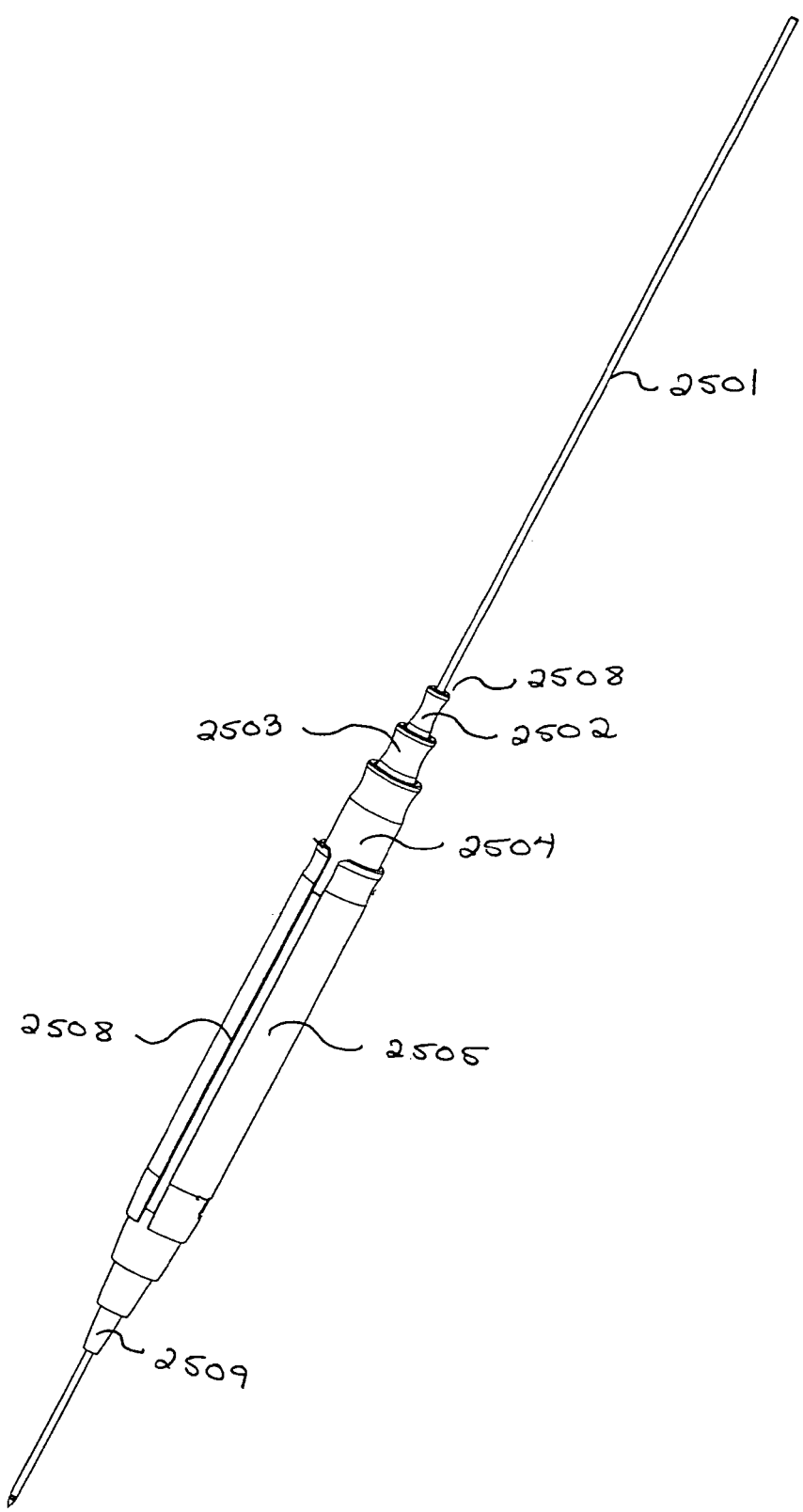
FIG. 25 is a perspective view of guide wire passing through multiple dilations.

FIG. 25 shows guide wire 2501 intended to be positioned in a pedicle (not shown). Dilators 2502, 2503, 2504, 2505 are positioned over guide wire 2501 in consecutive larger dimensions, with approximately 1 inch separation in height from each. The first dilator 2502 has hole 2508 longitudinally therethrough which allows dilator 2502 to pass over guide wire 2501. Dilator 2502 has distal end 2509 which is tapered to allow for ease of assembly and insertion through the tissue. Dilator 2503 is then passed over dilator 2502. Dilator 2504 is passed over dilator 2503 and then dilator 2505 is passed over dilator 2504. Note that dilator 2505 has slot 2508 down one side to allow for the removal of wire 2501 and guiding a screw to the bone as discussed above.

Figures 26, 27:
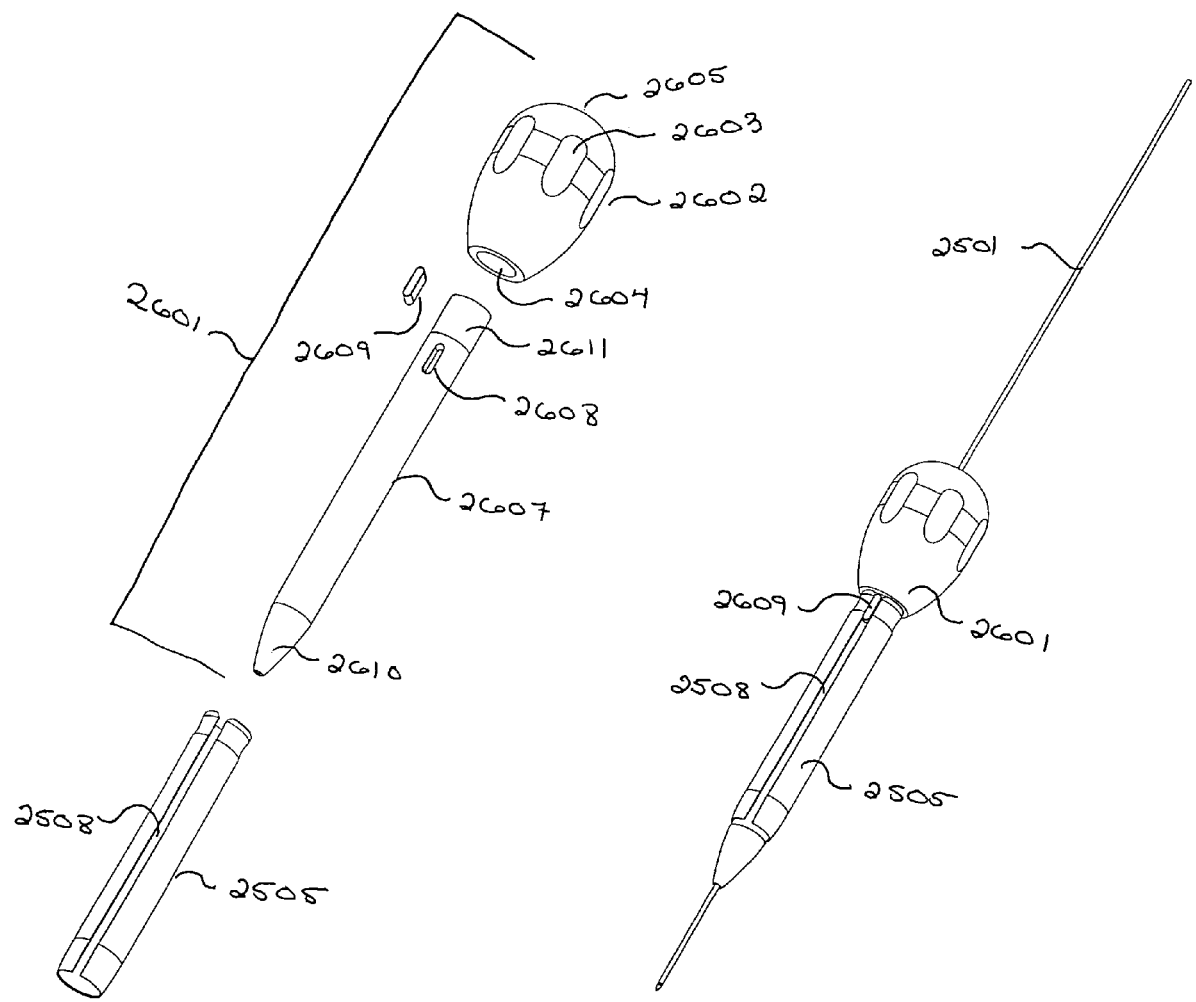
FIG. 26 is an exploded perspective view of an obturator in accordance with the present invention.
FIG. 27 is a perspective view of the obturator shown in FIG. 26.

FIG. 26 is an alternate method for inserting working cannula 2505 that uses what is called an obturator, such as obturator 2601, which includes three parts. Part 1 is handle 2602 which has a driving surface or palm gripping surfaces 2603, and also has a hole 2605 which goes down the length of the handle for passing over guide wire 2501. Handle 2602 also has hole 2604 for the purposes of receiving tube 2607 which is part 2. Tube 2607 has distal end 2610 which is tapered for passing the obturator through the tissue. Obturator 2601 acts as the first three dilators and has key way hole 2608 which allows key 2609 to be pressed into cannula 2608. The key way acts to center guide wire 2505 when obturator 2607 passes over the guide wire. Proximal end of tube 2607 has radial surface 2611 which is pressed into hole 2604 of handle 2602. Part 3 is dilator 2505 with slot 2508 therein FIG. 27 shows dilator 2505 assembled with the obturator 2601. Key 2609 is mated within channel 2508.

Figures 28, 29:
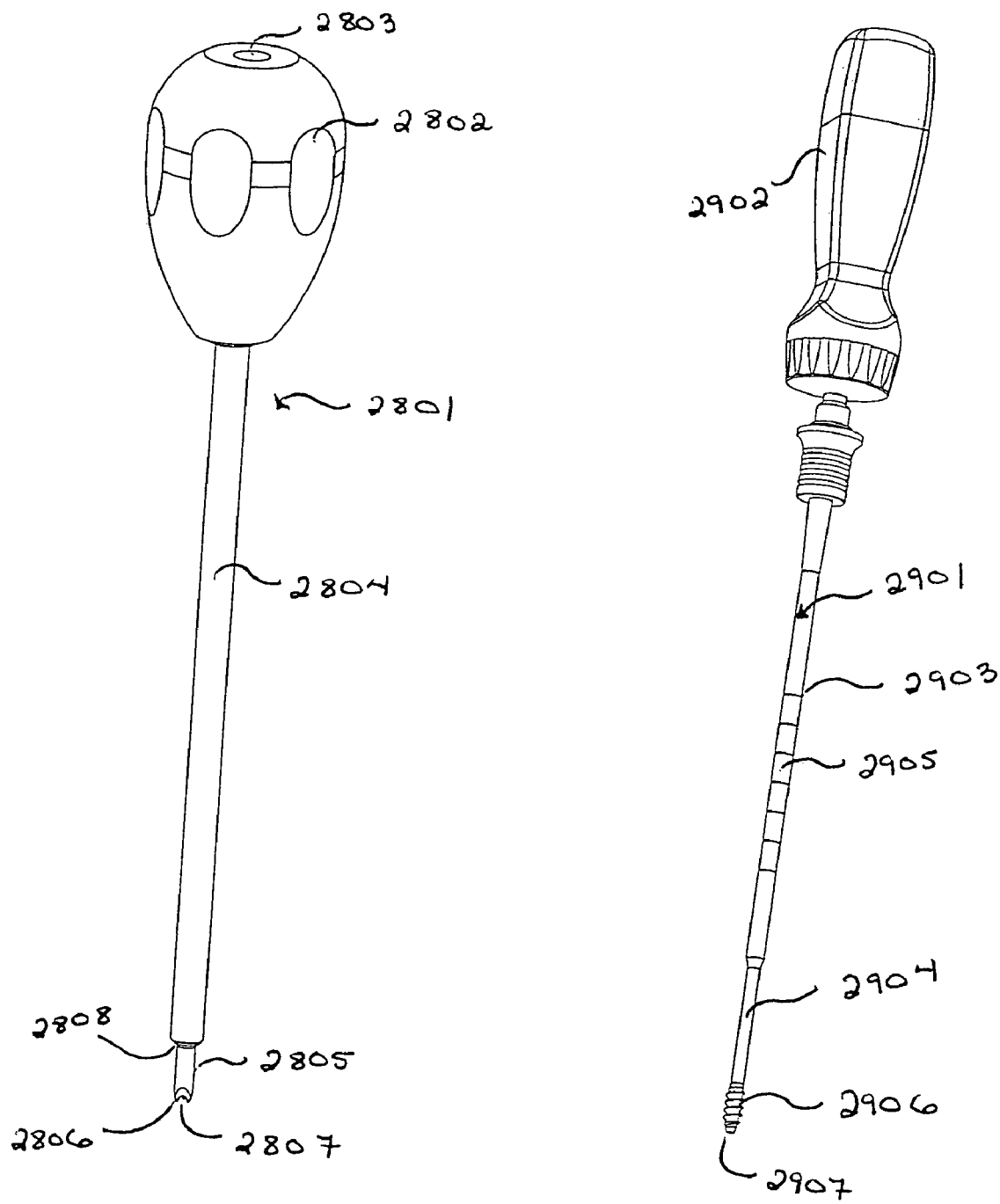
FIG. 28 is a perspective view of an awl in accordance with the present invention.
FIG. 29 is a perspective view of a tap in accordance with the present invention.

FIG. 28 shows awl 2801. As described above awl 2801 may be used to enlarge the hole in the pedicle formed by a bone biopsy needle, but it is not required where the bone biopsy needle, is large enough in diameter to make the awl unnecessary. The purpose of an awl is to break through the tough cortical bone that is present at the entrance to the pedicle. This is helpful for patients having high bone density. Awl 2801 has handle 2802 that is much like obturator handle 2602. Handle 2802 has opening 2803 therein for allowing the awl to pass over guide wire 2501 from FIG. 25. Awl 2801 also has tube 2804 with distal reduced diameter surface 2805. The distal end has cutting surfaces 2806, typically three but any number will work. These surfaces are serrated around exit opening 2807. The awl is passed over the guide wire and then rotated down into the bone until shoulder 2808 contacts the bone. The awl is then pulled out, leaving a hole in the bone. Awl 2801 may also be used to create an indentation at the bone entry point, the purpose of which is to facilitate the seating of the tip of anchor 500 from FIG. 5 at the anchor entry point FIG. 29 shows tap 2901 for creating threads in the bone using threads 2906. The diameter of the tap is typically anywhere from a half of a millimeter to 1 millimeter undersized from the thread size of the screw that will be placed in the bone. The actual size depends on bone density. The greater difference in the tap size to the screw size determines how much fixation and pull-out strength the screw will have. Preferably, one would use a half millimeter undersized tap. Thus, for a 6.5 millimeter screw, a 6 millimeter tap would be used. The tap has indicators 2903 on main body 2905 which identify how deep the surgeon has gone. Lines 2903 typically are in 10 millimeter increments. Body 2905 has reduced diameter portion 2904 at the distal end. At the extreme distal end are cutting surfaces and threaded surfaces 2906 which are in the shape of an acorn. The acorn shape facilitates easier tapping and traveling down the middle of the pedicle rather than using a tap having longer straight threads which tend to follow the trajectory of the guide wire. The acorn tap tends to be more forgiving and finds the center of the pedicle because it seeks the softest bone. The guide wire passes out of awl 2901 via opening 2907.

The tap, as shown, is a fully cannulated tool. At the proximal end, handle 2902 is typically a straight ratchet handle. This could be a non-ratchet or a T handle and it mounts to tap 2901 for the purposes of ease of insertion of the tap. The tap has a tapered distal end 2904 so as to facilitate proper seating within the hole so that the tap is started easily.

After the pedicle has been tapped to the desired depth, the tap is removed and the guide wire remains inside the largest cannula, which is cannula 2505 shown in FIGS. 25, 26, and 27. Before the screw can be inserted, an extension must be attached to the head assembly 100 (200) to create a communication channel from outside the skin to head 300 or 1500 as appropriate.

Figures 30, 31, 32:
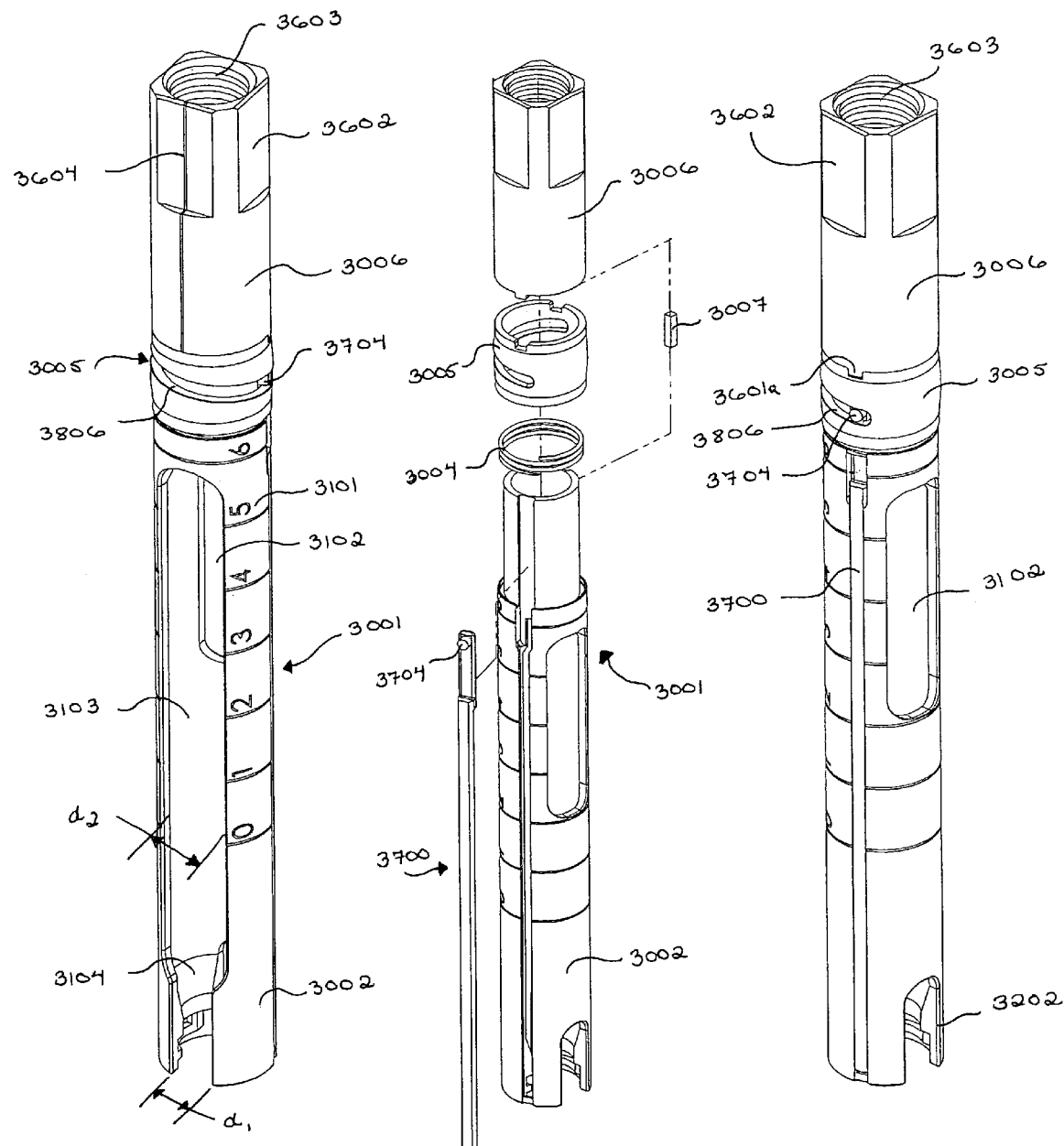
FIG. 30 is an exploded perspective view of an extension, cannula assembly in accordance with the present invention.
FIG. 31 is a perspective view of the assembly of FIG. 30.
FIG. 32 is a perspective view of the assembly of FIG. 31 rotated 90 degrees.

FIG. 30 shows an embodiment of an extension used to facilitate the insertion and assembly of the stabilization system and method described in accordance with the present invention. Extension assembly 3001 includes tube 3002 which attaches at one end to a poly-axial head, such as poly-axial head 300 or 1500. Over the opposing end of tube 3002 a locking ring is installed with spring 3004. Drive head 3006, which is used to tighten the extension to a poly-axial head, and to provide attachment for an anti torque handle, attaches to locking ring 3005 and tube 3002 using torque key 3007 for proper positioning. Extension assembly 3001 also includes slide 3700 which fits into a slot on tube 3002 and engages locking ring 3005 by means of pin 3704.

FIGS. 31 and 32 shows extension assembly 3001 assembled. Starting at the proximal end, thread 3603 in drive head 3006 acts as a mechanism for mating the driver guides which are part of the drive assemblies shown in FIGS. 48 through 55, to be described hereafter. Torque flats 3602 are used with anti-torque handle shown is FIG. 66a, as will be described. Drive head 3006 mates with locking ring 3005. Locking ring 3005 provides the mechanism for locking the extension to the poly-axial head assembly, such as the ones shown in FIG. 11 or 14. Locking ring 3005 includes slot 3806 which is formed in locking ring at an angle by having the slot begin at one end below the midline of the locking ring and end at the other end above the midline. Slide 3700 is coupled to slot 3806 of locking ring 3005 by means of pin 3704 and extends down tube 3002 where it can engage with a poly-axial head connected to the extension.

Figure 37:
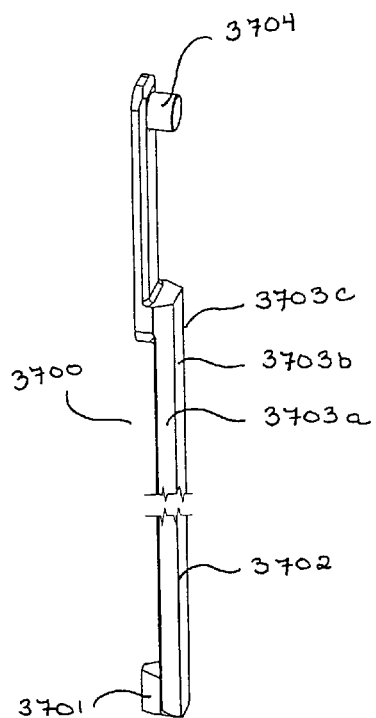
FIG. 37 is a perspective view of the slide from FIG. 30.

While slide 3700 will be shown in greater detail with reference to FIG. 37, its purpose is to lock a poly-axial head with the extension. It accomplishes this by sliding up and down the tube in response to the twisting of the locking ring 3005. Twisting locking ring 3005 causes slot 3806 to move from its low end to its high end or vise versa. Pin 3704 coupled to slot 3806 translates the twisting motion of the locking ring 3005 into a linear up and down motion by slide 3700 as pin 3704 traverses slot 3806 from low to high or high to low. A locking extension at the end of slide 3700 proximal to the poly-axial head, shown in FIG. 37 as element 3701, locks the poly-axial head in place by engaging with slots 332 and 334 of head 300 from FIG. 3 or slots 1511 and 1512 of head 1500 from FIG. 15. The poly-axial head is unlocked by moving the locking extension of slide 3700 out of the referenced slots by twisting locking ring 3005 such that pin 3704 moves to the high position in slot 3806.

Tube 3002 includes numbers and lines 3101 positioned in 10 millimeter increments, which are used, if desired, to determine the depth the anchor has been threaded into the bone. Tube 3002 remains constant and the screw turning tool is inside the tube. If a surgeon desires to go down 40 millimeters then he/she would take a tool with a mark on it and move the mark, for example, from 1 to 5. Tube 3002 has several openings. The first opening is 3103. It is the largest opening with a distance d2. The second opening is opening 3104 having a reduced distance d1. This change of distance is important during rod transfer (rotation from in-line to horizontal) because the rod proximal end enters tube 3001 at 3103 and is guided into the poly-axial head held by tube 3002 by the reduced opening formed by distance d2.

Figure 38:
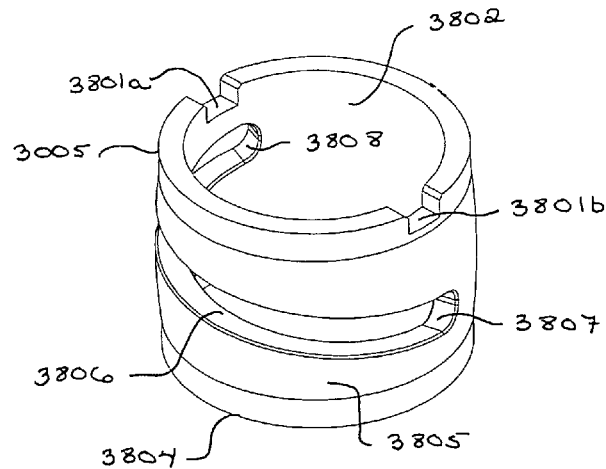
FIG. 38 is a perspective view of twist ring 3005.

Protuberance 3601a, shown in FIG. 32, interacts with indentions 3801a and 3801b from FIG. 38 on twist ring 3005. These indentions prevent the twist ring from inadvertently twisting thereby raising slider 3700 causing the assembly to unlock. In operation, to unlock the assembly twist ring 3005 is pushed down freeing latch 3801a from latch 3601a. Spring 3004 holds the twist ring upward into a latched position. Window 3202 allows the rod to back out of the attached head during its transfer. Window 3102 is used for inserting multipedicle systems as will be discussed in greater detail with reference to FIGS. 67-77.

Figure 33:
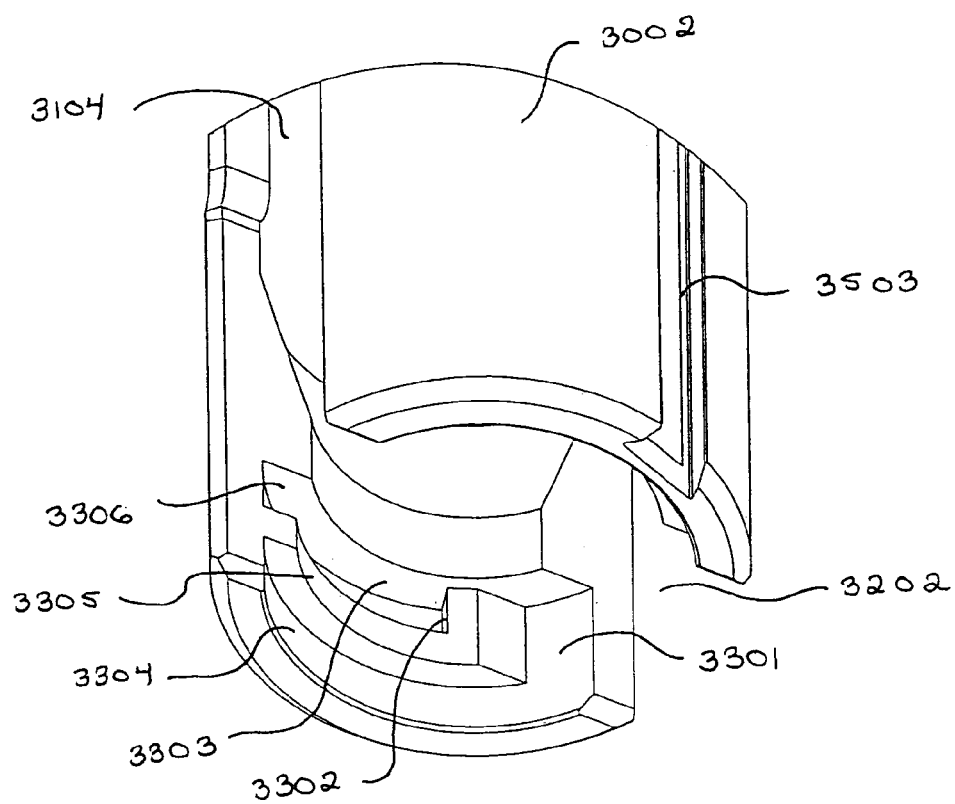
FIG. 33 is a perspective view of the tube end of the assembly shown in FIG. 30.

FIG. 33 describes details of the distal end of tube 3002 of FIG. 30. Starting at the top here is dovetail slide groove 3503. Opening 3202 is below the slide groove next to opening 3301 adapted for receiving head 300 or 1500. Also shown is channel groove 3306 having top surface 3303. Grove 3306 creates radial surface 3305, which is also a surface for keying onto head 300 (1500). Bottom surface 3304 is adapted for contacting the head as well. Torquing surface 3302 connects to the head to allow for torque transfer from the extension to the head when the pedicle screw is being tightened, as will be discussed.

Figure 34:
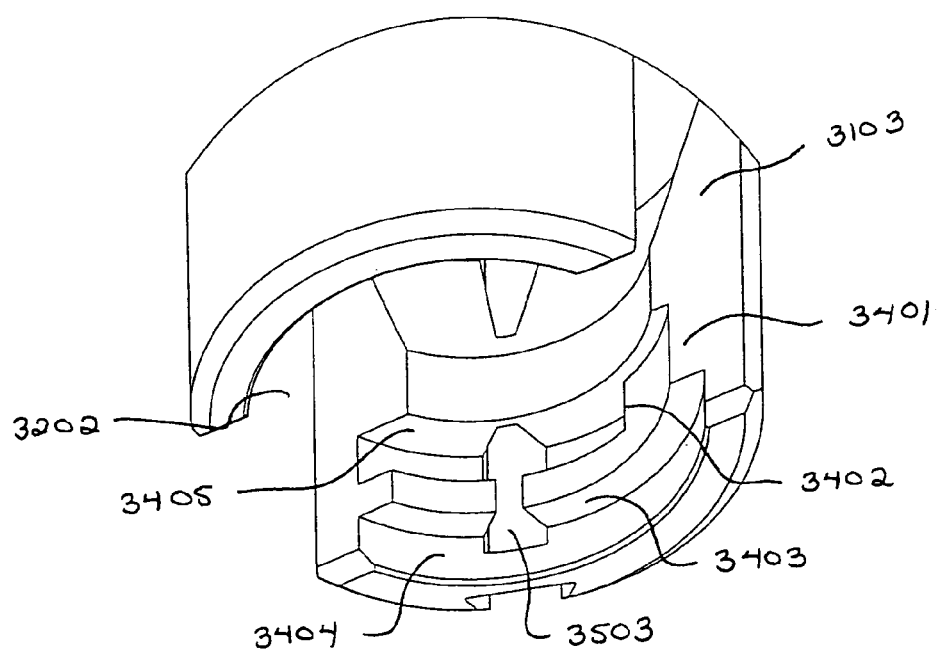
FIG. 34 is a perspective view of the tube end of FIG. 33 rotated clockwise approximately 90 degrees.

FIG. 34 shows openings 3103 and 3202 with key 3401 adapted to engage the head as will be discussed hereinafter. Opposite side torquing surface 3402 is shown as is surface 3405 which is a groove similar to groove 3306 (FIG. 33). Triangular cut 3503 and surfaces 3403 and 3404 are adapted for mating with the head. Reduced diameter portion 3404 mates to the head as well. These parts are designed to prevent a radial motion between the parts when slider 3700 is down and mating the groove of the head. Groove 3405 which mates to a portion on the head functions to prevents separation that could be caused by an upward force on extension 3001.

Figure 35:
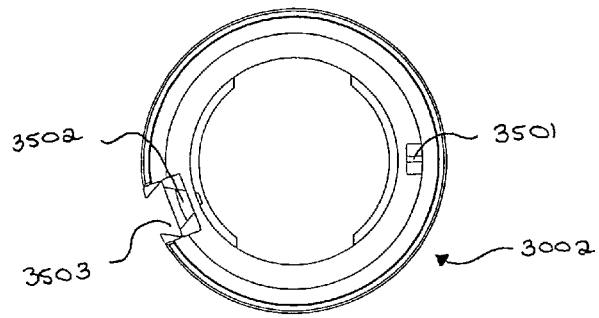
FIG. 35 is a bottom view of the tube end of FIG. 33 illustrating a dovetail channel.

FIG. 35 is a top down view looking down at tube 3002 illustrating dovetail channel 3503, as will later be described, for receiving sliding member 3700 from FIG. 30. Triangular portion 3502 receives key 3701 of slider 3700 shown in FIG. 37. Also shown in FIG. 35 is key way cut 3501 for receiving torque key 3007 shown in FIG. 30. Torque key 3501 mates with slot 3605 from FIG. 36, to be described hereinafter, for the purposes of transferring torque so that when countertorque is applied against flat 3602 shown in FIG. 30 such that transmission of torque is allowed from top proximal member 3006 from FIG. 31 through torque key 3007 to the lower portion of extension 3002.

Figure 36:
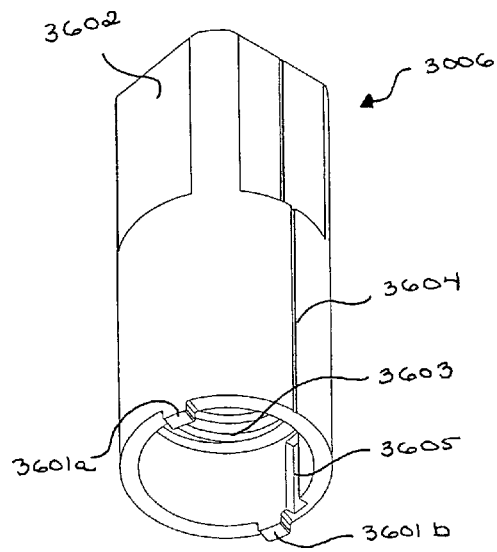
FIG. 36 is a prospective view of the drive head from FIG. 30.

FIG. 36 shows that the proximal end of head 3006 has surfaces 3602 for the transmission of the torque as described. Line 3604 shown in FIG. 36 is an alignment line used to align the extensions relative to one another. Thread 3603 is used to accept a tool as will be described. Torque key groove 3605 is where key 3007 of FIG. 36 mates. The torque goes between groove 3605 and slot 3501, shown in FIG. 35, such that the one side surface is against the back wall of slot 3501, and the other surface is against the back wall of slot 3605. Protuberances 3601a and 3601b, as described hereinafter, serve to lock the position of twist ring 3005 (FIG. 30) in the desired position.

FIG. 37 shows slide 3700 having at its proximal end pin 3704. Body 3702 has three surfaces, 3703a, 3703b and 3703c. These surfaces go into the three mating sides of dovetail 3503 of body 3002 as shown in FIG. 35. Triangular element 3701 is positioned at the distal end of slider 3700 and acts to lock head 300 onto the extension as has been described.

FIG. 38 shows twist ring 3005 having slots 3801a and 3801b for receiving protuberances 3601a, 3601b of top portion 3006 from FIG. 36. Ring 3005 has central bore 3802 wherein it is positioned over the top portion of tube 3002 which is shown in FIGS. 30 and 35. Ring 3005 also has middle body 3805 and distal surface 3804. Within middle body 3805 there is slot 3806 which is a helical pattern with ends 3807 and 3808 which are positioned approximately 180 degrees from one another. Slot 3806 receives pin 3704 of slider 3700. Since slider 3700 is fixed in rotational position, when the twist ring is rotated it forces slider 3700 to move up or down as pin 3704 travels inside slot 3806. The down position would be when pin 3704 is against stop 3807 and the up position would be when pin 3704 is against stop 3808.

Figure 39:
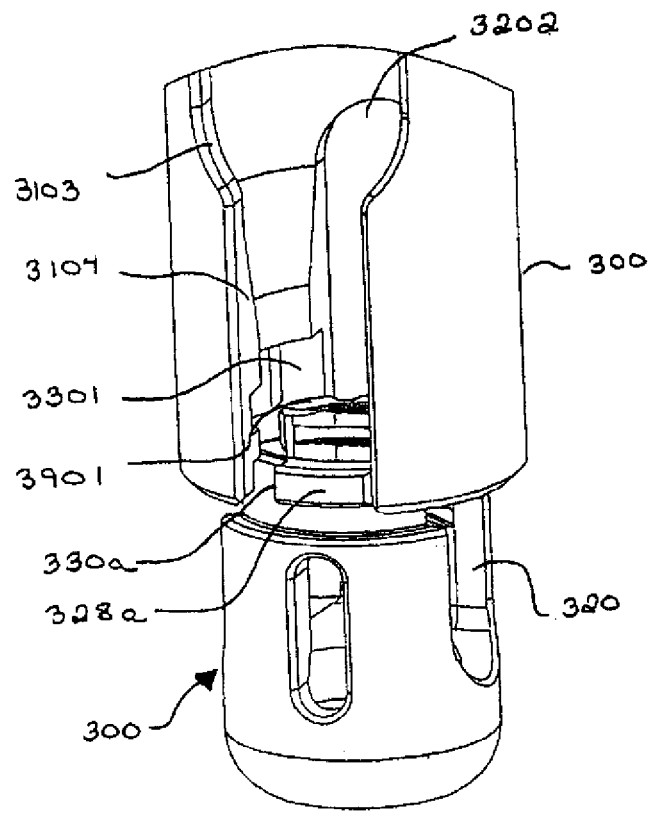
FIG. 39 is a perspective view of the head of FIG. 3 in relation to the tube of FIG. 30.
Figure 40:
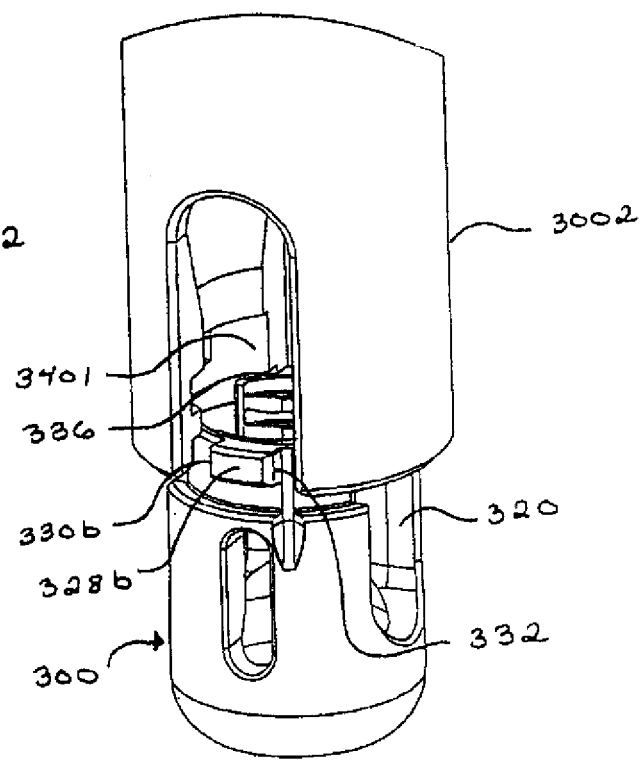
FIG. 40 is a perspective view of the assembly of FIG. 39 with the tube rotated 180 degrees.

FIGS. 39 and 40 show head 300 with channel 320. Key 128a is adapted to mate with tube 3002. When the parts are mated part 3901 is locked into extension 3002. On the opposite side male surface 3401 of extension 3002 is mated with female portion 336 of head 300 as well as 328b and the torquing surface 330a. Torquing surface 330b is also shown in FIG. 39. FIG. 40 shows channel 320 as well as slider mating surface 332 of head 300. This forces the head into the extension in only one direction.

Figure 41:
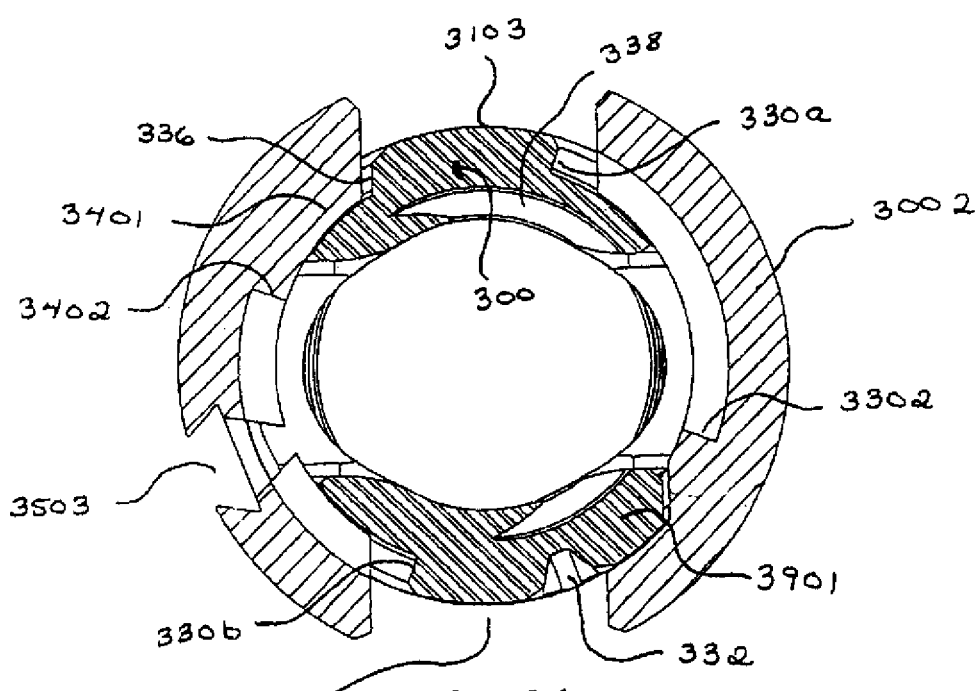
FIG. 41 is a cross-sectional bottom view of the assembly of FIG. 39.
Figure 42:
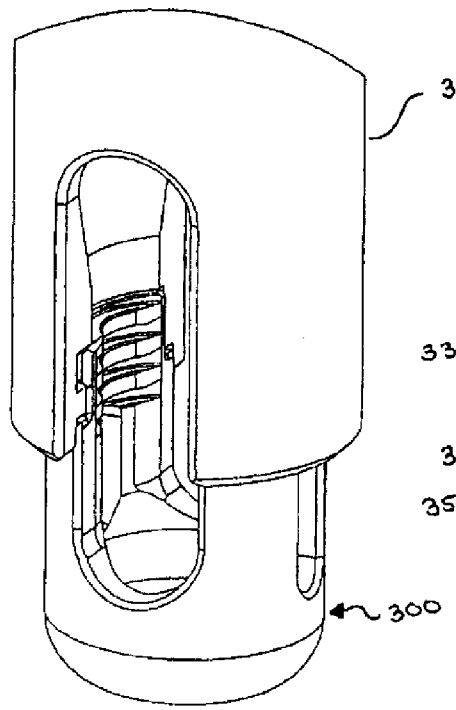
Figure 43:
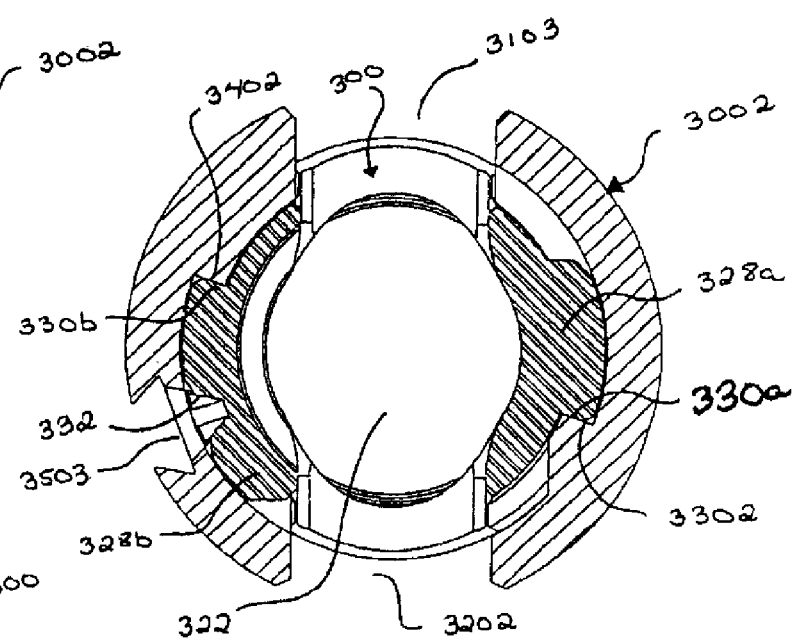
Figure 44:
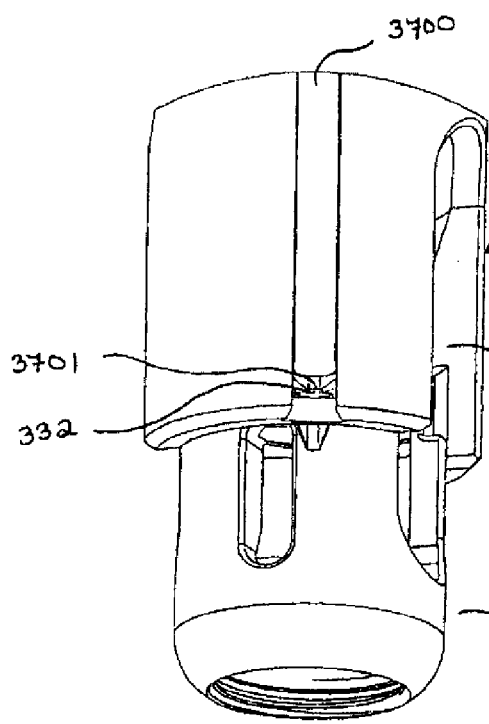
Figure 45:
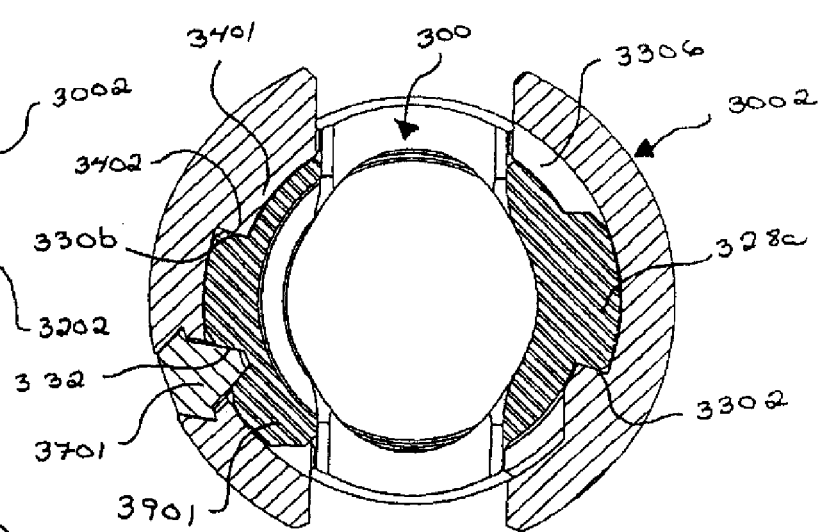
Figure 59:
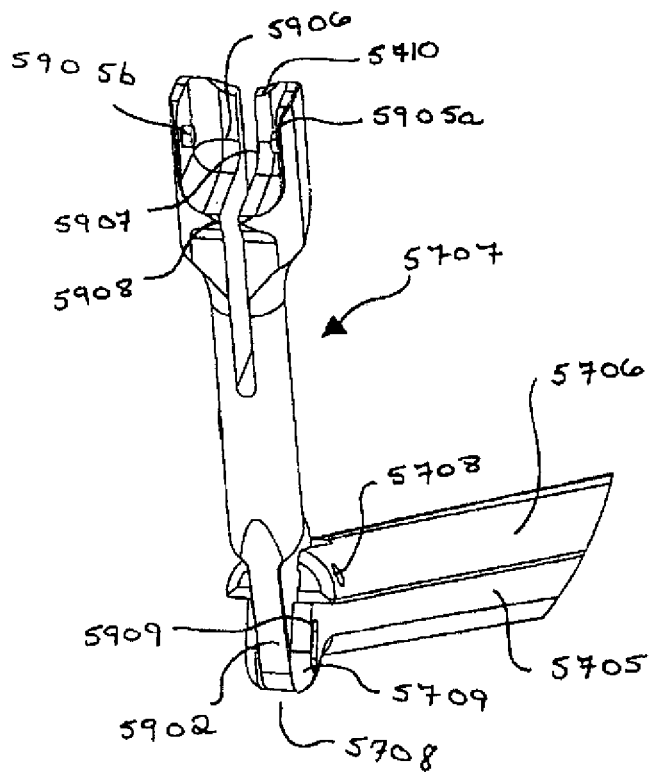
Figure 60:
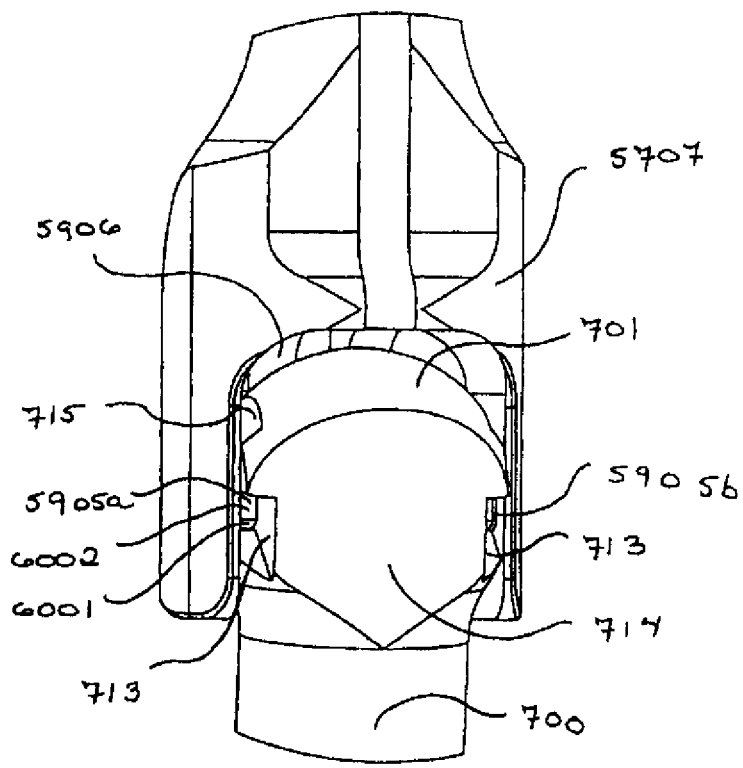

FIG. 41 shows a cross-section when top section 328a of the poly-axial head is inserted until it is in contact with surfaces 3306 and 3405 of the extension. Opening 3103 is shown illustrating torquing surface 330b there and 330a on the opposite side. Opening 3202 of the extension is shown at the bottom. One important part of this figure is that portion 3401 is shown interacting with portion 336, and portion 3901 of head 300 is mated with portions 330b and 330a of extension 3002. This makes this a one-way device that can not go in the other direction, and a clockwise rotation of the head or a counter-clockwise rotation of the extension would bring surfaces 330*b* and 3302 and surfaces 330*a* and surface 3402 into contact, thereby trapping the head in a vertical position.

Figure 42:
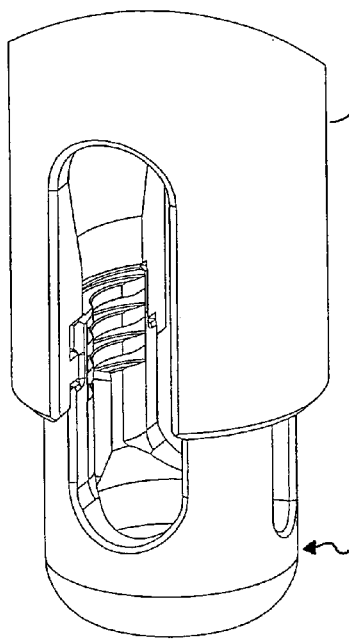
FIG. 42 is a perspective view of the assembly of FIG. 39 with the tube fully engaged with the head.

FIG. 42 shows head 300 being twisted into locking position with respect to extension 3002.

Figure 43:
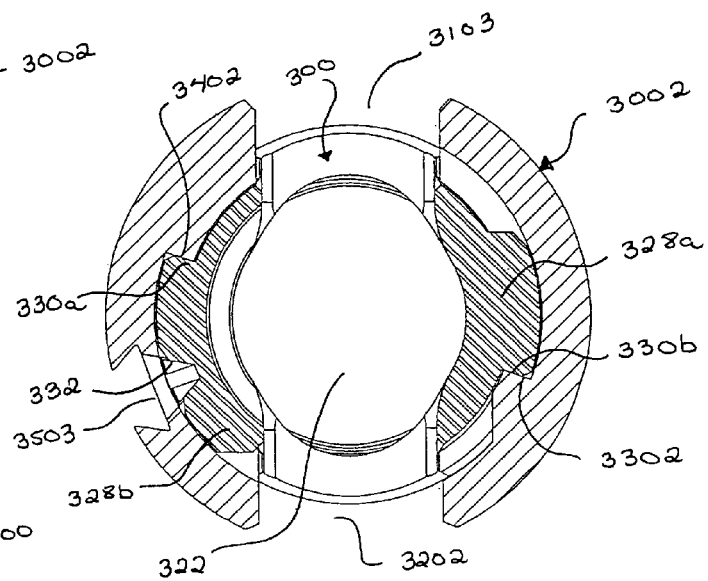
FIG. 43 is a cross-sectional bottom view of the assembly of FIG. 42.

FIG. 43 is a cross-section through the midline of the 3303 groove from FIG. 33. With rotation, 330*a* and 330*b* are in contact with portions 3402 and 3302 respectively. Opening 3202 is shown as well as opening 3103. Channel 332 of head 300 is positioned at the same position as channel 3503 so as to be in position to receive slider 3700, tab 3701. Portion 328*a* is positioned in its locked position as shown with portion 330*b* stopped against stop 3302 and with 330*a* stopped against stop 3402. FIG. 42 shows that there is an actual axial trapping by using the male/female key way.

Figure 44:
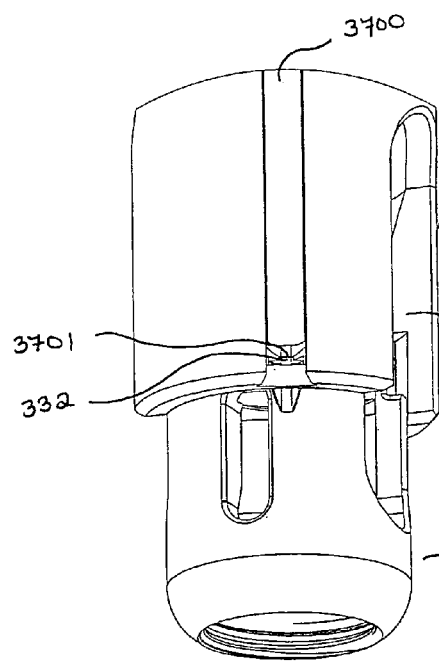
FIG. 44 is a perspective view of the assembly of FIG. 42 rotated clockwise 90 degrees.

FIG. 44 shows slider 3700 pushed down into locking position by twisting the twist ring (not shown) to reposition the twist ring into its lower position forcing slider 3700 down so that element 3701 from FIG. 37 engages in groove 332.

Figure 45:
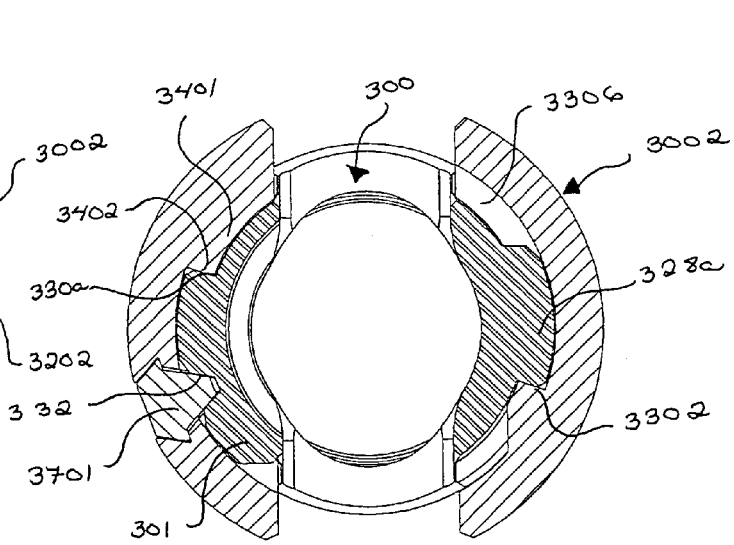
FIG. 45 is a cross-sectional bottom view of the assembly of FIG. 44.

FIG. 45 shows this operation in cross-section with locking element 3701 of slider 3700 engaged with groove 332 in head 300. At this point the head is locked axially and cannot rotate out of its axial position.

FIG. 46 shows one embodiment of a measurement tool, such as tool 4600, having legs 4602 and 4603 and indicator arm 4605 that moves in relation to arm 4604 having the actual measurements thereon. Indicator arm 4605 has indictor 4613 thereon showing distance between screws displayed in lines of numbers 4612. Handle 4606 is an extension to leg 4603 and has a bend for finger insertion. Leg 4602 has handle 4607. As the handles move apart so do the legs, pivoting around pin 4608. Fixed portion 4620 pivots around pin 4609 connected to leg 4603 while indicator arm 4605 pivots around pin 4610 attached to leg 4602. Both parts then pivot about pin 4611 so that as the distal ends 4615 and 4614 separate from one another, legs 4603 and 4602 pivot about pins 4608 and 4611 causing arm 4605 to move across the path of the radius of the arc between pedicle screws. The radius in this case being the length from pin 4611 to the numbers on measuring arm 4604. This then reads the distance at the distal end of the tool. The numbering on arm 4604 is adjusted to account for the variance between the implanted pedicle screw and the arm.

Tool 4600 has two openings 4616 and 4617 at the bottom of legs 4603 and 4602, respectively. These openings are to engage whatever features they are to measure the distance between. This measurement tool would be typically used once one screw is positioned. Also, measurements can be taken across two guide wires between pedicles so that a rod length can be selected.

FIG. 47 shows tool 4600 inserted in cannula 3001 in contact with the head of the first implanted screw such as assembly 100, from FIG. 1. Distal end 4617 of tool 4600 comes to rest on top of drive 505 and mates with drive 505. Leg 4603 is then positioned over guide wire 2501 and slipped down the guide wire to the base of the pedicle. This then allows the surgeon to read the pedicle to pedicle distance on the tool. The measurement tool can also be used to measure cross connector lengths, or another distance within the limits of the scale of the measurement tool.

FIGS. 48 and 49 describe one embodiment of a driver, such as driver 4800. Driver 4800 has three components as shown in FIG. 49. Component 4804 is the distal end which mates with proximal end 701 of rod 700. This mating is primarily via surface 710, but can also be with flats 712*a* and 712*b*, for the purposes of delivering torque from the user's hand down through the driver to the rod and through the rod to the screw.

FIG. 49 shows tool 4800 in an exploded view. Top portion 4802 is the proximal end, and has flats 4913, top 4912 and ring 4911. Male screw threads 4910 engage with female screw threads 4905 of lower portion 4804. Middle section 4909 has knurled surface 4909, driver guide 4908 with threaded portion 4907 which mates with the drive head of an extension assembly from FIGS. 30 through 32. Section 4803 has bore 4906 extending therethrough. Threads 4910 mate with threads 4905 and lock top portion 4802 to lower portion 4804. Section 4803 can then rotate about section 4802 and can move laterally with respect thereto for the purpose of locking and latching itself to threads 3603 of extension 3006 from FIG. 36. Lower portion 4804 has drive head 4901 which includes distal surface 4902 and pocket 4904 for receiving spherical portion 741 of rod 700 shown in FIG. 9. Drive head 4901 has opposite flats 4903 and 4902 for engaging flats 712*a* and 712*b* of rod 700 shown in FIG. 7.

Figure 50:
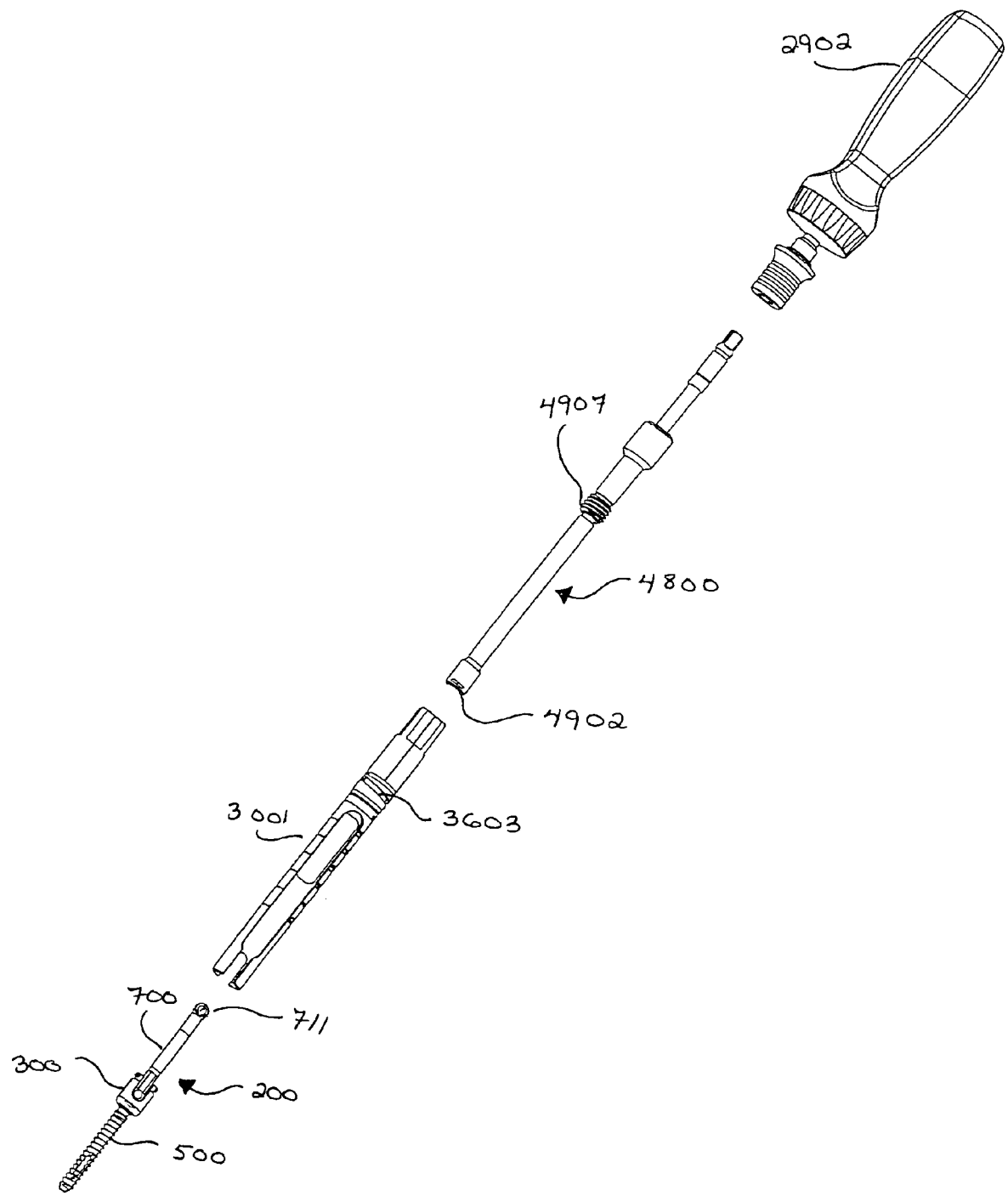
FIG. 50 is an exploded perspective view of the assembly of FIG. 11 in relation to the assembly of FIG. 30 in relation to the driver of FIG. 48, and a handle assembly in accordance with the present invention.

FIG. 50 shows screw assembly 200 from FIG. 1 inside extension 3001 with tool 4800 about to go inside extension 3100. Handle 2902 will mate with tool 4800. Portion 3001 has been latched onto head 1500 as described above. Tool 4800 is then passed down inside the extension and mated with the proximal end of rod 700. Then threads 4907 are threaded into threads 3603 of extension 3001 forcing distal end 4902 against rod end 711. The threads are used to compress the assembly completely, such that a rigid assembly occurs, allowing the surgeon, using ratchet handle 2902 on proximal surfaces 4913 and 4911 of tool 480, to rotate anchor 500.

Figure 51:
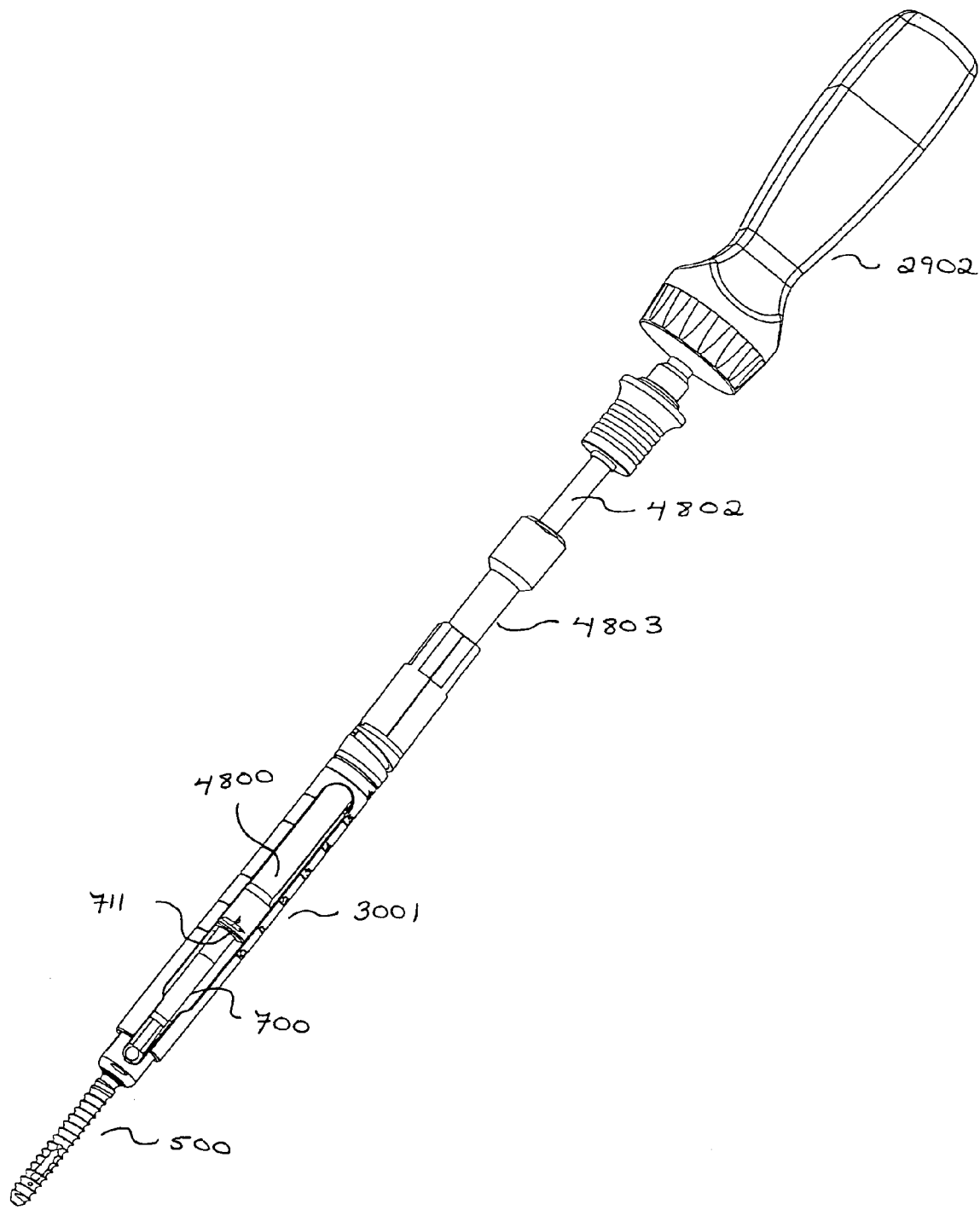
FIG. 51 is a perspective view of the assemblies of FIG. 50 mated together in accordance with the present invention.

FIG. 51 shows spherical surface 711 captured by distal end 4902 of tool 4800 inside extension 3001. As portion 4802 turns, threaded sleeve 4803 does not turn since portion 4802 turns inside bore 4906 of thread sleeve 4803. When tool portion 4802 turns, the rod 700 turns and turns anchor 500. During this time, rod 700 is effectively part of the anchor driving mechanism. By forming the poly-axial rod-assembly head 300 in this manner, rod 700 is part of the anchor assembly and does not need to be inserted after the anchor assembly has been put in place. This means that the rod does not have to be delivered from outside the extension into the patient after the anchor assembly has been set.

FIG. 52 shows one example of a tool, such as tool 5200, used to drive in the screw associated with assembly 100 from FIG. 1. This differs from tool 48 FIG. 48 by replacing drive head 4901 which is designed to mate rod 700 with drive head 5205 which is designed to mate with drive mechanism 505 of anchor 500 in assembly 100. Tool 5200, therefore, is designed to go all the way down and interact with the drive means on the anchor itself. At the distal end there is distal driving member 5203 and drive head 5205 ending in driver 5204 which connects with the drive means of the screw. The upper portions of tool 5200 operate as does tool 4800.

FIG. 53 is an exploded view of tool 5200, and differs from the tool of FIG. 49 only in the choice of drive heads.

Figure 54:
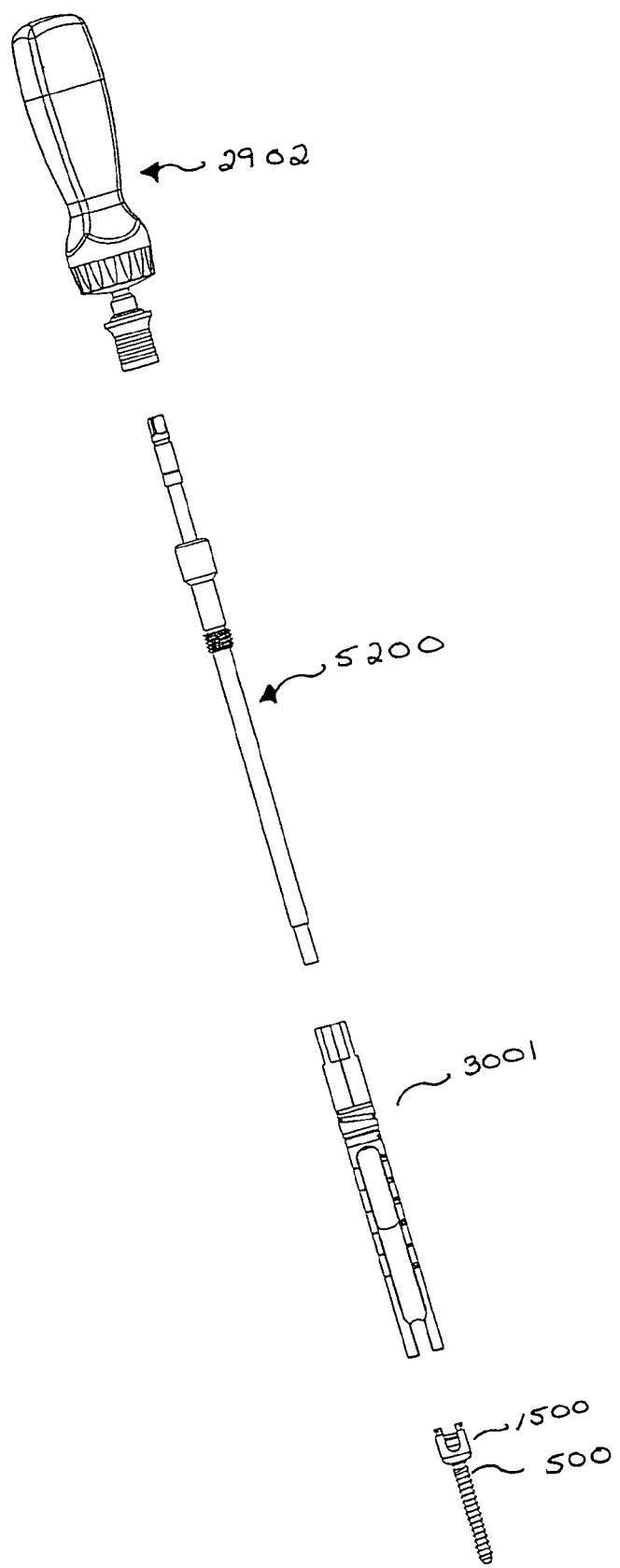
FIG. 54 is an exploded perspective view of the assembly of FIG. 14 in relation with the assembly of FIG. 30, the drive tool of FIG. 48, and a handle assembly in accordance with the present invention.

FIG. 54 shows screw assembly 100 from FIG. 1, extension 3001, screwdriver 5200 which is passed down through extension 3001 to engage the top of the drive mechanism (not shown) of anchor 500 inside head 1500.

Figure 55:
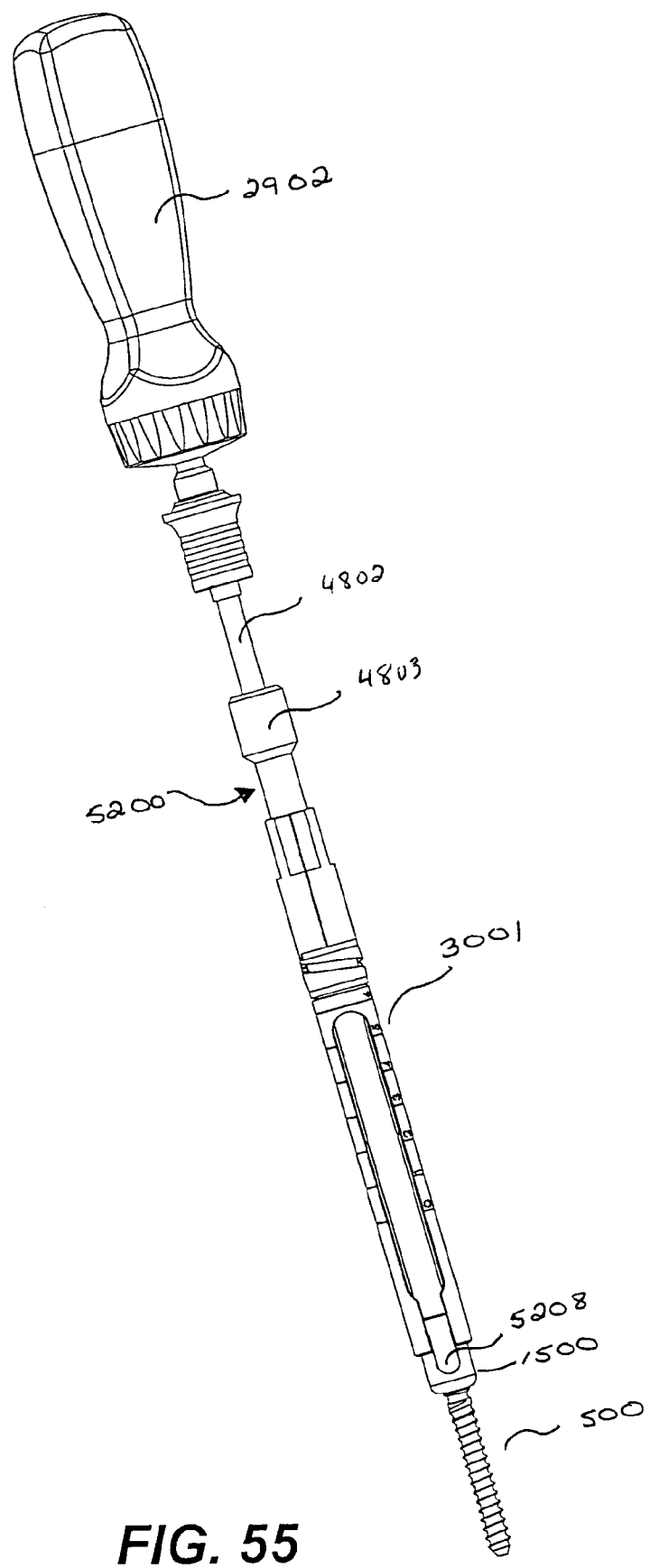
FIG. 55 is a perspective view of the assemblies of FIG. 54 mated together in accordance with the present invention.

FIG. 55 shows the assembly of anchor 500, head 1500, extension 3001, tool 5200 and handle 2902. This assembly is then sent down into the bone after the tap (over the guide wire on the off axis screw guide, if desired) so that anchor 500 can be embedded in the pedicle. The guide wire is pulled out and retracted and then the screw is able to overtake the axis that the guide wire had and is then turned down into the waiting tapped hole.

Figure 56:
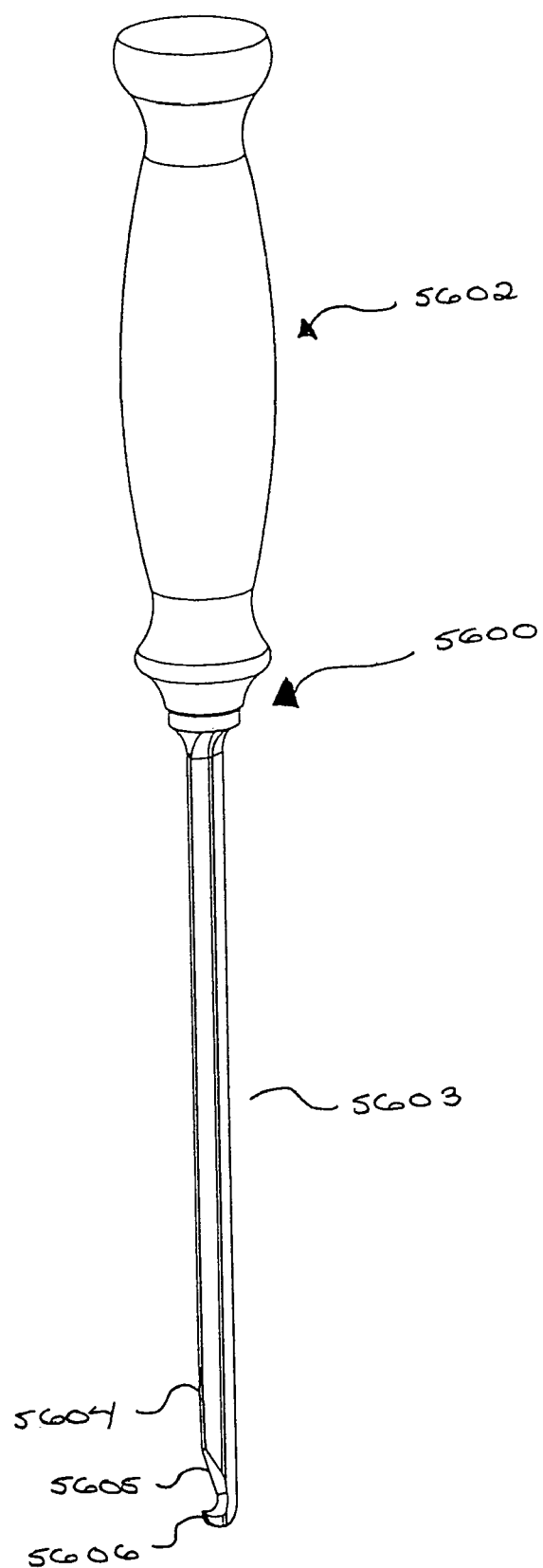
FIG. 56 is a perspective view of a tool for locating a second pedicle in accordance with the present invention.

FIG. 56 illustrates one instrument for the procedural step of separating muscle and fascia tissue between the first and second assemblies 100, 200. Tool 5600 has handle 5602 and blade 5603. Blade 5603 has a sharp cutting portion 5604 and also has tip 5606. On the inside of that tip 5606 is cutting surface 5605. After the pedicle is tapped, tool 5600 is used to open a channel from the screw to the next pedicle. This is done by working through the tissue and separating the muscle. Tool 5600 is not intended to be a cutting instrument, but rather a separating instrument. However, if the distal end gets caught on a piece of deep fascia, the surgeon pulls up and the blade tip 5606 cuts that deep fascia. This allows the surgeon to work over to the second pedicle, creating a separated plane of tissue.

After the second guide wire is inserted and dilation has occurred, an inter-pedicle measurement is taken as discussed above so that a proper length rod can be selected. The rods could be 25, 30, 35, 40 millimeters, or greater, in increments of 5 mm or any other increment that would be appropriate. Once the rod is selected it is added to the assembly discussed with respect to FIG. 11.

Figure 58:
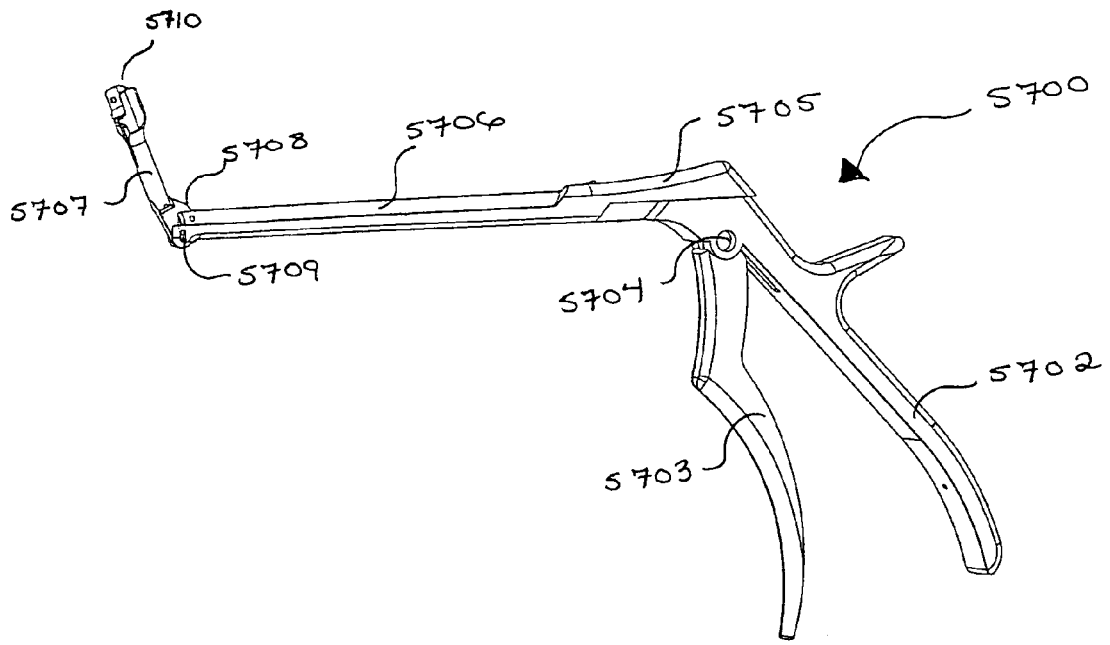
FIG. 58 is a perspective view of the rod transfer tool of FIG. 57 with the distal arm bent upward.

FIGS. 57 and 58 illustrate one example of a rod transfer tool 5700. The handle is a "pistol grip" having elongated portion 5702 and an elongated portion 5703 which rotates about pin 5704 to form a trigger. The trigger pushes sliding member 5705 which moves along elongated portion 5706. Movement of portion 5706 operates to rotate distal end portion 5707 about pin 5708. As slider 5705 moves forward, distal arm 5707 rotates about pin 5708 as shown in FIG. 58. Pin 5709 allows for partial pushing motion between slider 5705 and end portion 5707. Distal end 5710 transcribes on arc as it rotates upward as is shown in FIG. 58.

FIG. 59 shows details of arm 5707 partially rotated about pin 5709. Racetrack cut 5909 allows pin 5709 in the proximal end of arm 5707 to move from the up position to the down position and then back up to the top. Flat area 5902 of arm 5707 engages slider 5705 and handle 5706. Rod transfer tool 5700 is designed to grasp rod 700 at proximal end 701 and pulls rod 700 along the path to poly-axial rod capturing assembly 1500, at which point rod transfer tool 5700, by means of cam 5908 pushes rod 700 out of arm 5707 and toward head 1500. At no time does rod transfer tool 5700 apply pressure to the sides, top or bottom of rod 700.

Distal end 5710 has bore 5906 which is a pocket having cut 5910 for purposes of pushing the rod and urging the rod down into poly-axial rod-capturing assembly 100 from FIG. 1 when the rod is being transferred. End 5710 also has two tines 5905*a* and 5905*b* in pocket 5906. Channel cut 5907 allows tines 5905*a* and 5905*b* to be sprung away from one another when they are being inserted onto the spherical portion 711 of rod 700. Raised radial surface 5908 acts as a cam to push the rod away from arm 5707 when the rod meets the particular exit angle as will be described hereinafter.

FIG. 60 shows pocket 5906 of arm 5707 as well as spherical portion 701 of rod 700. Note that channels 713 in the rod end allow tines 5905*a* and 5905*b* to exit from rod end 701 when the rod is rotated into position. The tines enter via opening 715 which is sloped to act as a ramp to facilitate entrance of the tines. Tines 5905*a* and 5905*b* have partially radial surfaces 6001, interrupted by flat cut surfaces 6002.

FIG. 61 shows how instrument 5700 operates, reference will be made to rod 700 and its features shown in detail in FIG. 7. Once poly-axial rod assembly 200 from FIG. 1 is inserted into the bone with extension 3001 connected to head 300, instrument 5700 is inserted down the bore of extension 3001 as shown. Distal end 5710 of tool 5700 engages proximal end 701 of rod 700 causing tines 5905*a* and 5905*b* to splay apart as they engage the ramp at the proximal end of the rod, as discussed above. When the tines get to lip 722 of ramp 715 they drop into recess 713. The shape of tines 5905*a* and b insure that they remain in recess 713 until the end of tool 5700 is rotated into the release position. Tines 5805*a* and *b* have a large diameter which is perpendicular to exit ramp 716 and larger than the transition from recess 713 to exit ramp 716. Tines 5905*a* and b also have a small diameter which becomes perpendicular to exit ramp 716 upon the rotation of rod 700 in tool 5700. The small diameter of tines 5905*a* and *b* is smaller than the transition to exit ramp 716 allowing tines 5905*a* and *b* to exit their engagement with rod 700 at the proper orientation.

Once the rod 700 is engaged with tool 5700, upward pulling force is exerted by the surgeon which lifts rod 700 out of mating relationship with anchor 500 by disengaging drive mechanism 706 of rod 700 from drive 505 of anchor 500 as described in FIG. 5. Pulling up moves slide ring 800 to the top of channel 326*a, b* (FIG. 11) so that the distal end of the rod clears the top of drive mechanism 505 as it rotates over. By squeezing the trigger 5703 of tool 5700, the surgeon begins the rotation of arm 5707 which, in turn, causes rod 700 to pass through open slot 3103 portion of extension 3001 from FIG. 31.

Figure 62:
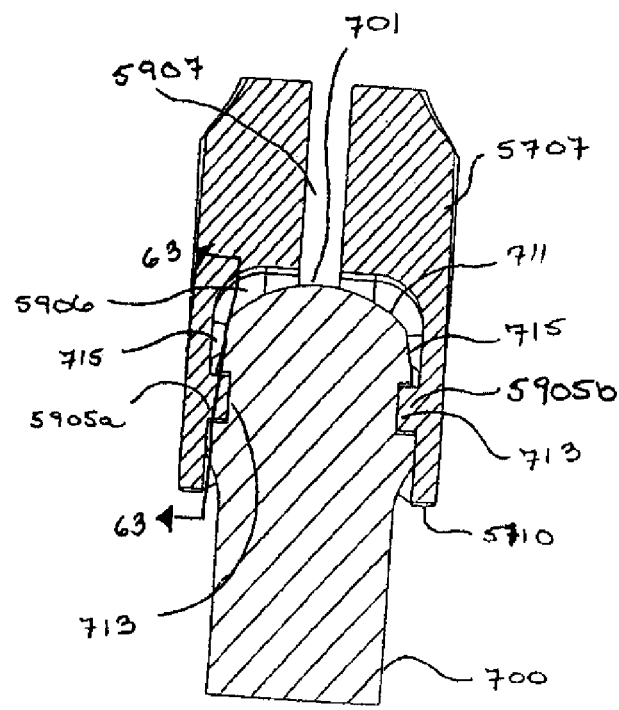
FIG. 62 is a section view taken through lines 62-62 of FIG. 61.

FIG. 62 is a section taken through lines 62-62 of FIG. 61 illustrating ramp 715, channel cut 5907 and arm 5707. Tines 5905*a* and 5905*b* are snapped into cylindrical recesses 713 on rod 700. The rod is captured and can be pulled up as discussed above.

Figure 63:
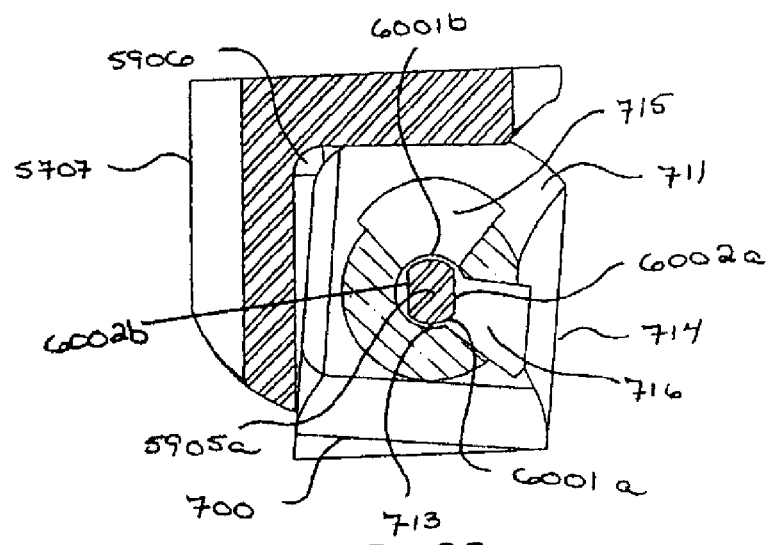
FIG. 63 is a cut-away view illustrating the orientation of a tine of the rod transfer tool of FIG. 57 with the distal end of the rod of FIG. 9.
Figure 70:
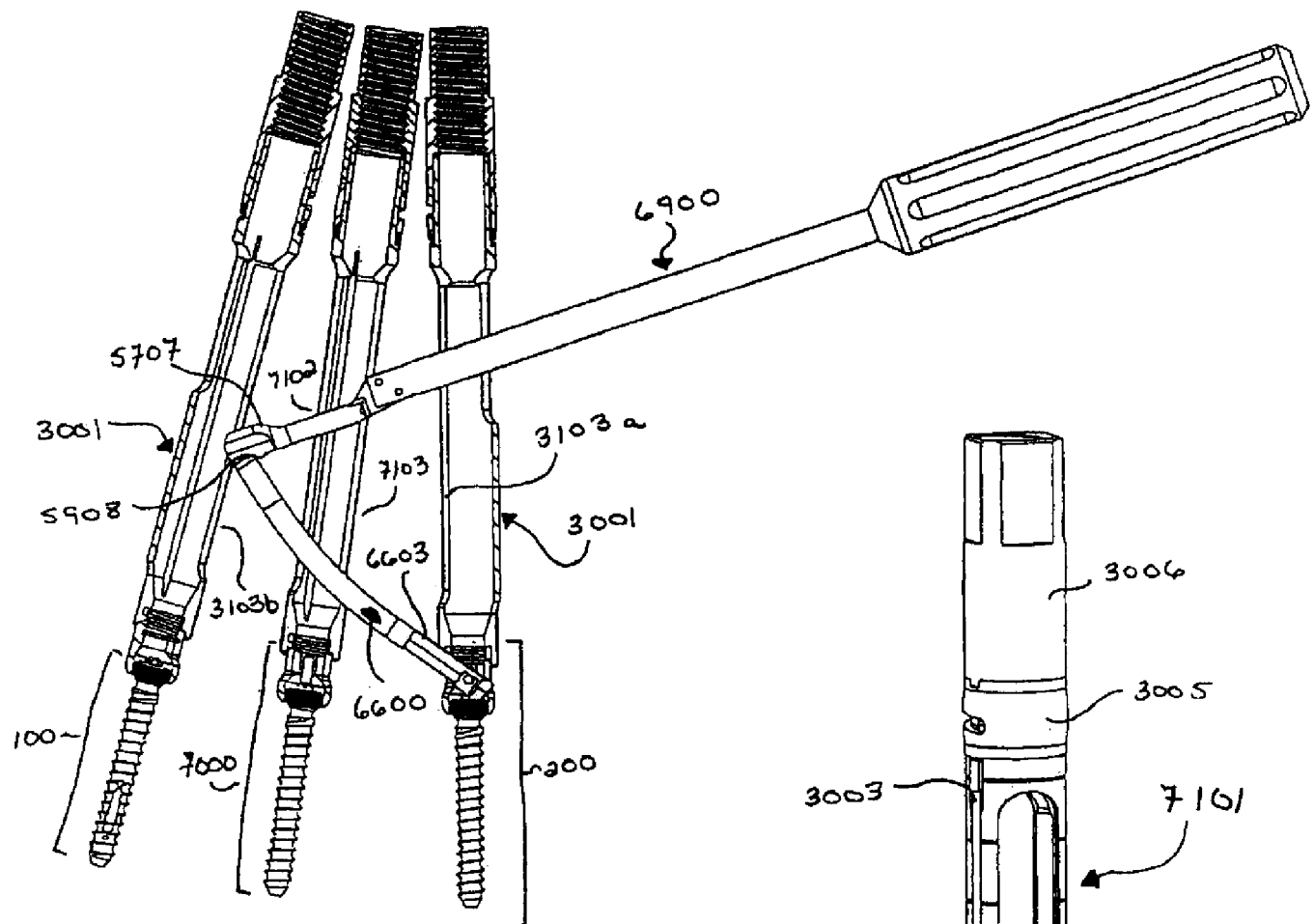
Figure 71:
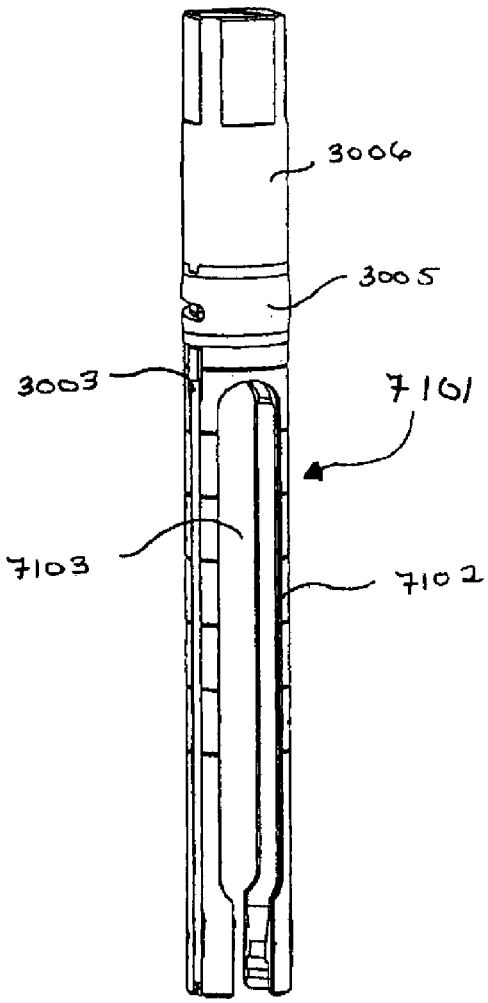
Figure 74:
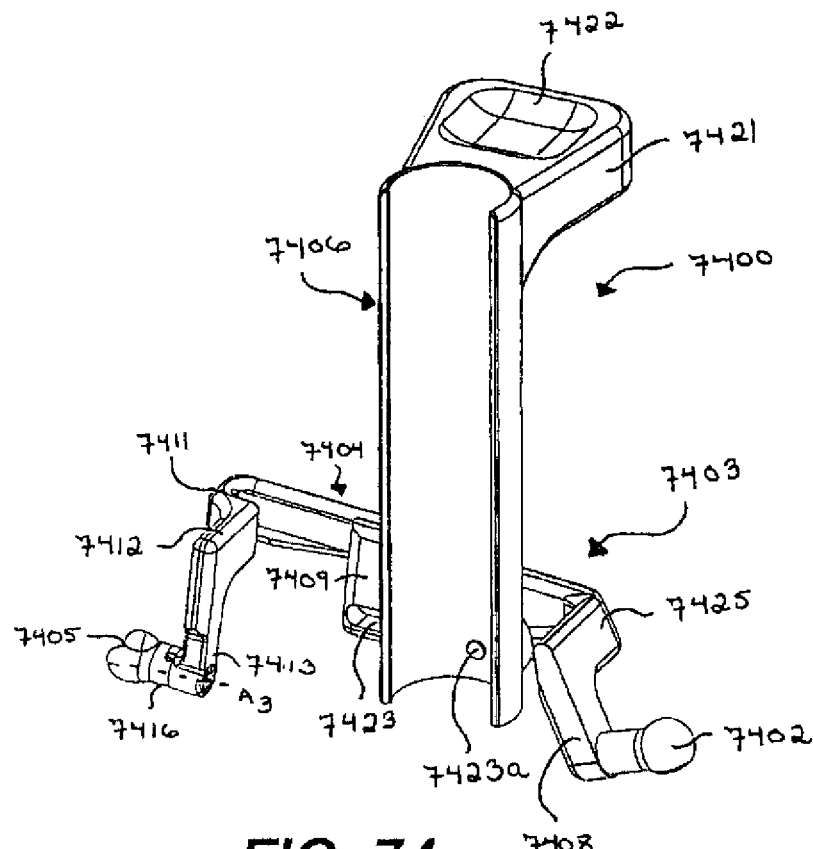
Figure 75:
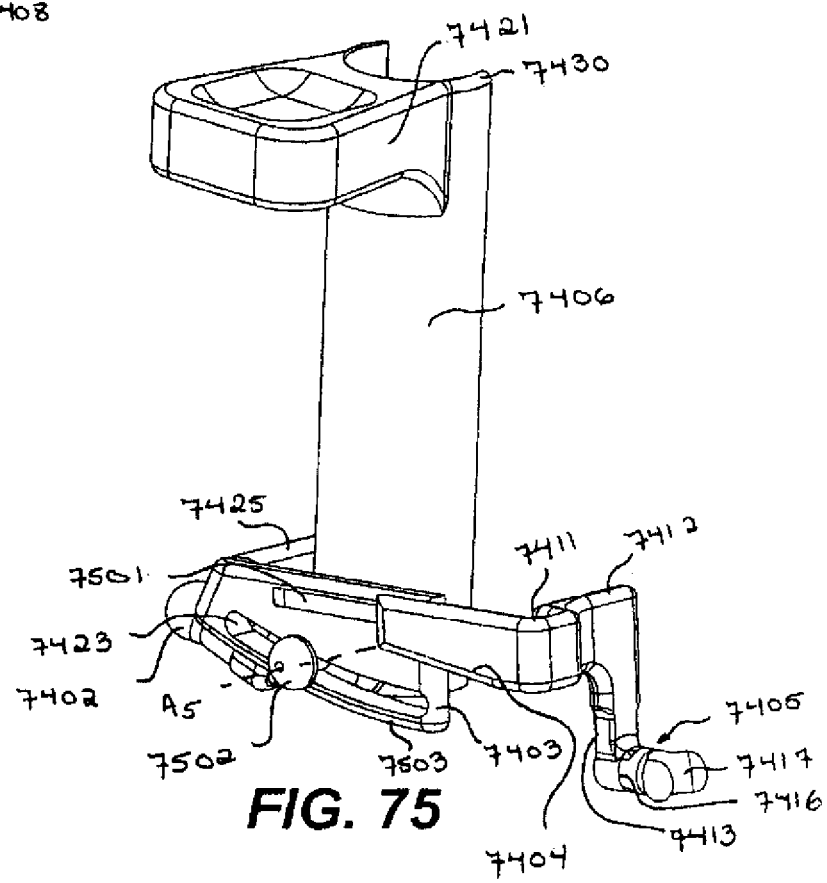
Figure 76:
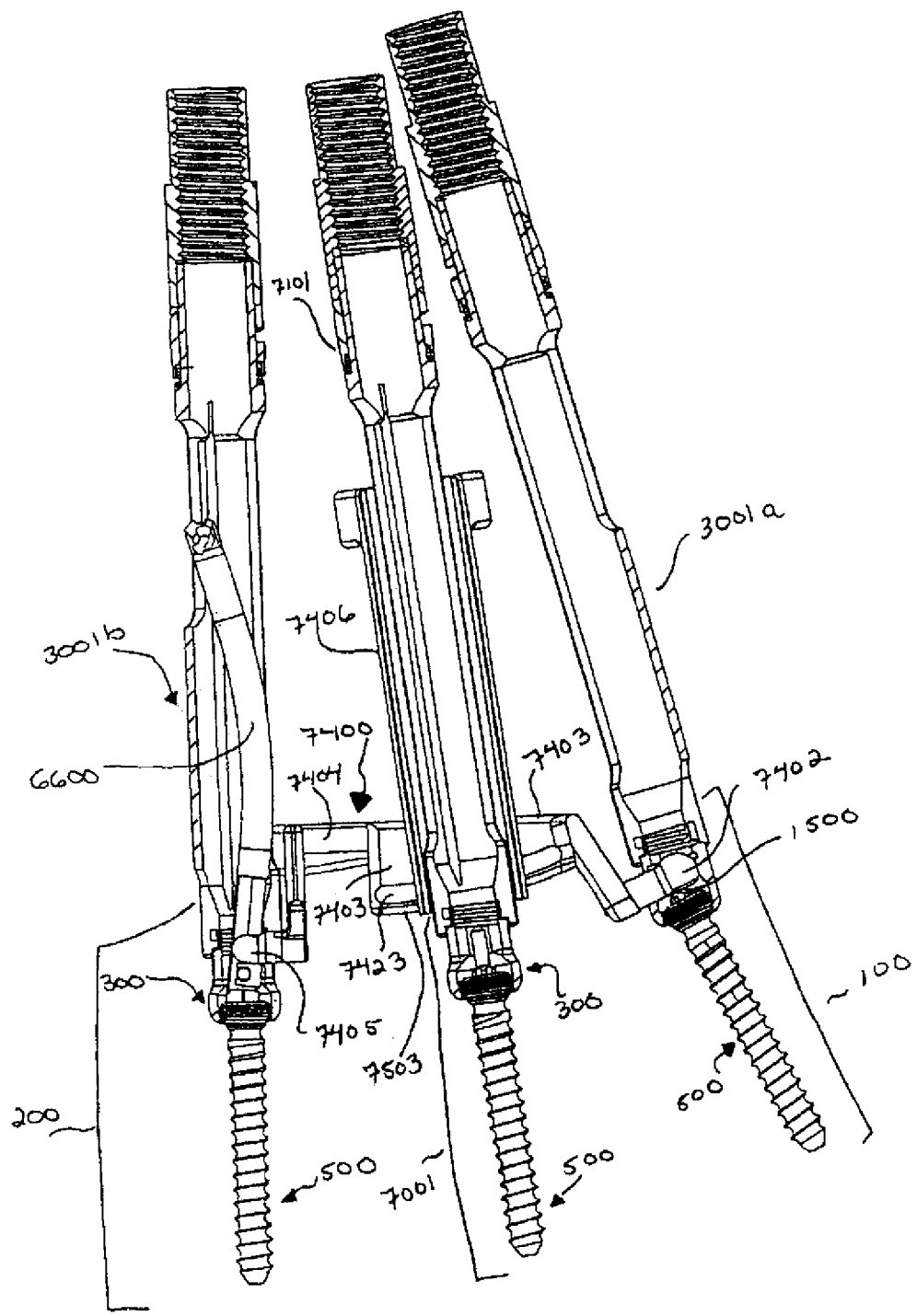
Figure 77:
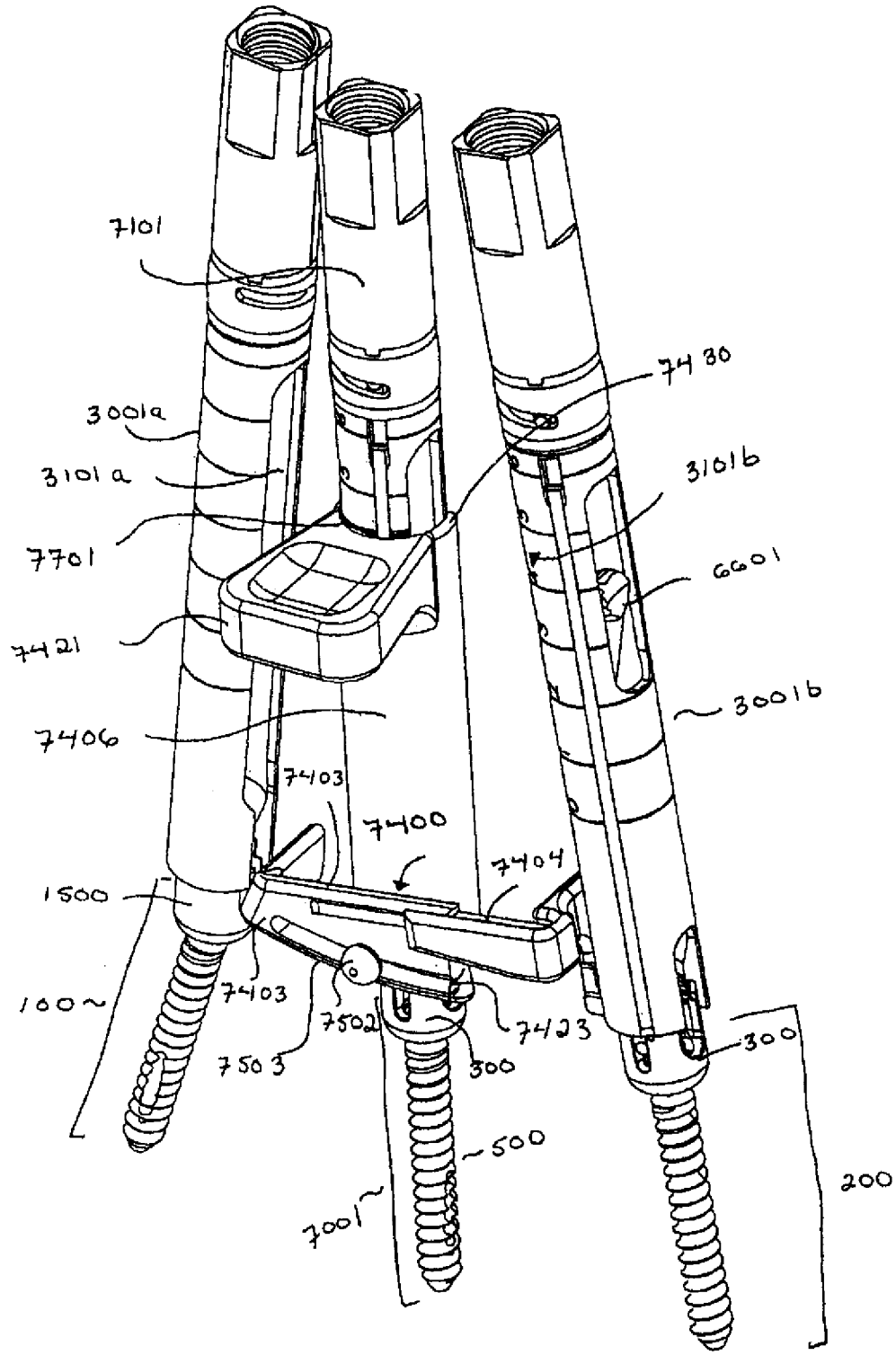

FIG. 63 is a cut-away view illustrating the orientation of tine 5905*a* in rod hole 713. Rod arm 5707 has pocket 5906 around rod 700. Tines 5905*a* and b (b not being shown) entered via ramp 715. Tines 5905*a* and has four surfaces. It has flat surfaces 6002*a* and 6002*b* on the small diameter and curved surfaces 6001*a* and 6001*b* on the large diameter. As stated, once the tines snap into the holes they cannot come out until arm 5707 is rotated so that the flats on the tines line up with exit slot 710. This can only occur when arm 5707 moves through an arc of approximately 90°.

FIG. 64 illustrates tool 5700 in operation with arm 5707 rotating rod 700 from extension 3001*a* into extension 3001*b*. Note the angle that arm 5707 of tool 5700 is making with respect to the proximal end of rod 700. The design is such that once the rod end enters wide opening 3103 of extension 3001*b*, the tine flats will line up with the exit ramps (as discussed with respect to FIG. 63) and with the help of cam 5908 will release therefrom.

FIG. 65*a* shows a cross-section through section 65*a*-65*a* of FIG. 64 and illustrates tines 5905*a* and 5905*b* in pocket 5906 but radial surfaces 6001*a* and 6001*b* can now pass through exit slots 716. FIG. 65*b* is a cross section through section 65*b*-65*b* of FIG. 65*a* and again shows the small diameter of tines 5905*a* and be aligned to pass through the transition between recesses 713 and exit slots 716. Cam 5708 is also shown which, as it rotates, operates to push the rod end out of pocket 5906.

Figures 66A, 66B:
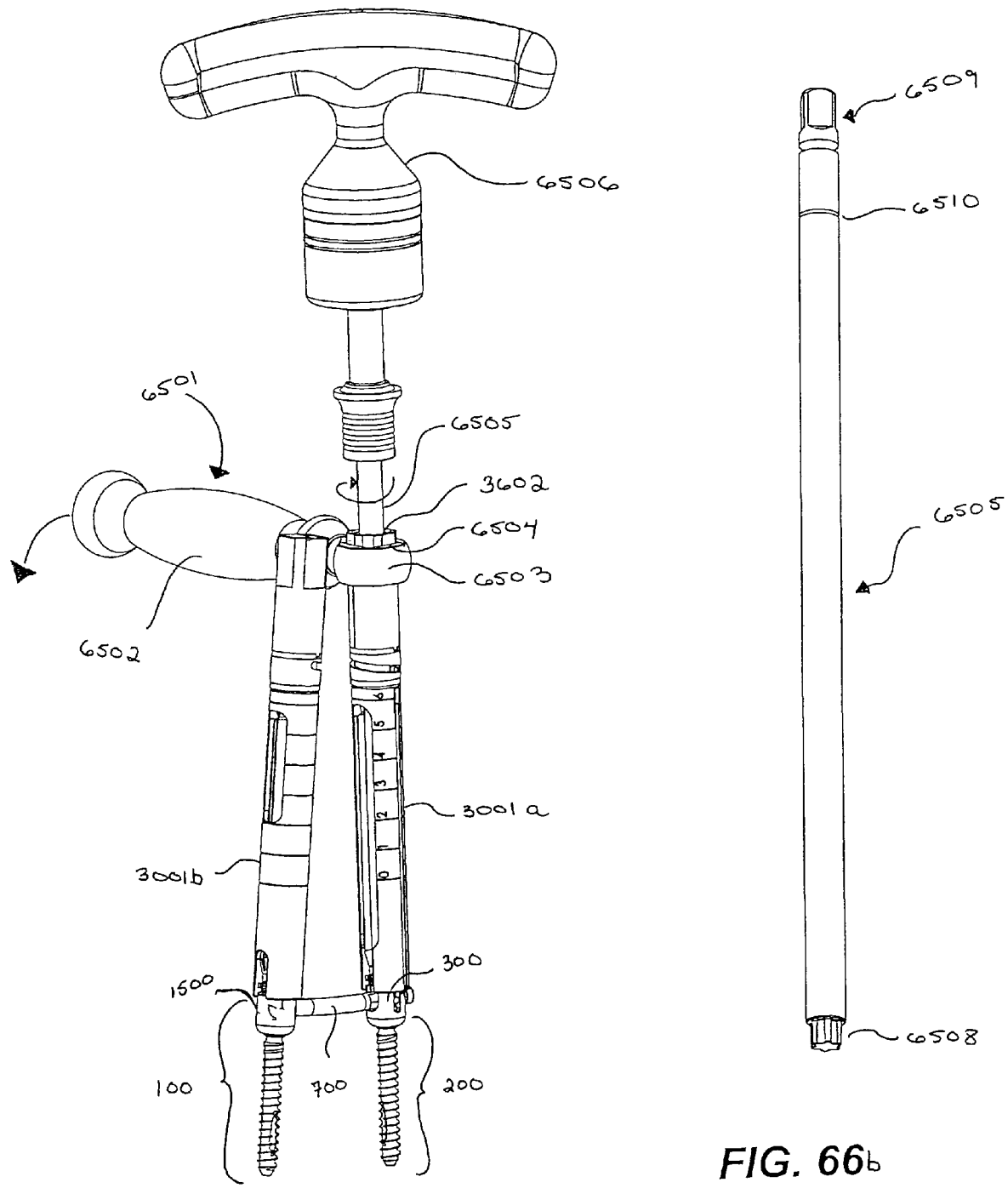
FIG. 66a is a perspective view of a drive tool and a counter torque handle in accordance with the present invention, where the drive tool is used to install the locking caps of FIG. 18.
FIG. 66b is a perspective view of a drive mechanism in accordance with the present invention.

FIG. 66*a*, shows the assembly for inserting and tightening the locking caps 1800 from FIG. 18 into the poly axial head assemblies 100 and 200, after rod 700 is rotated into place. Once rod transfer tool 5700 from FIG. 57 is removed from extension 3001*a*, rod 700 needs to be locked into the rigid position shown by FIGS. 22 and 23 by the installation of locking caps 1800. Locking caps 1800 are installed by the drive shaft 6505 attached to handle 6506 and using drive mechanism head 6508. A locking cap is positioned on drive mechanism head 6508 where drive mechanism head 6508 is sized to hold locking cap in place until it is tightened into a head assembly. Drive mechanism shaft 6505 with a locking cap is inserted down the extensions 3001*a* and *b* in turn and handle 6506 is twisted to seat locking cap 1800 into the poly-axial head assembly.

Used alone, drive mechanism shaft 6505 would not only screw locking cap 1800 in place but would also tend to place a torque on the poly-axial head assembly due to the friction between the threads of the locking cap 1800 and the treads of the poly-axial head assembly. This force would load the poly-axial head assembly, with such a load remaining after the end of the procedure potentially leading to problems with the assembly. To prevent this torque from being placed on the poly-axial head assembly, the system of the present invention uses anti-torque handle 6501 to place an opposing force on the poly-axial head assembly to the force applied by drive mechanism shaft 6505. Anti-torque handle 6501 includes handle 6502 and ring 6503 which has flats 6504 dimensioned to mate with the flats of the drive head of extension 3001. As the locking cap is tightened in one direction, for example clockwise, by drive mechanism shaft 6505, an equal force to the force applied to the poly-axial head assembly is applied in the opposite direction, for example counter clockwise, preventing any load from being introduced into the poly-axial head assembly.

FIG. 66*b* shows an embodiment of a drive mechanism shaft 6505 having a driving end 6508 and flats 6509 at the proximal end with quick connect ring 6510. As described, a locking cap, such as cap 1800 (FIG. 18) is placed on drive mechanism head 6508 of drive mechanism shaft 6505. End 6508 is a tapered surface so it taper locks with the locking cap so that the cap will not fall off. The length of tool 6505 is such that end 6508 reaches assembly 200 as shown in FIG. 66*a* which end 6509 comes out of the patient's skin. Handle 6506 is connected to the proximal end of tool 6505 which is rotated using handle 6506 to tighten locking cap 1800 thereby locking the assembly together.

Anti-torque handle 6501 can also be used to disconnect extension 3001*a* from assembly 200 by rotating assembly 3001*a*. Once released, assembly 3001*a* is removed from the patient's body and the incision can be closed leaving the assembly of FIG. 1.

Figure 67A:
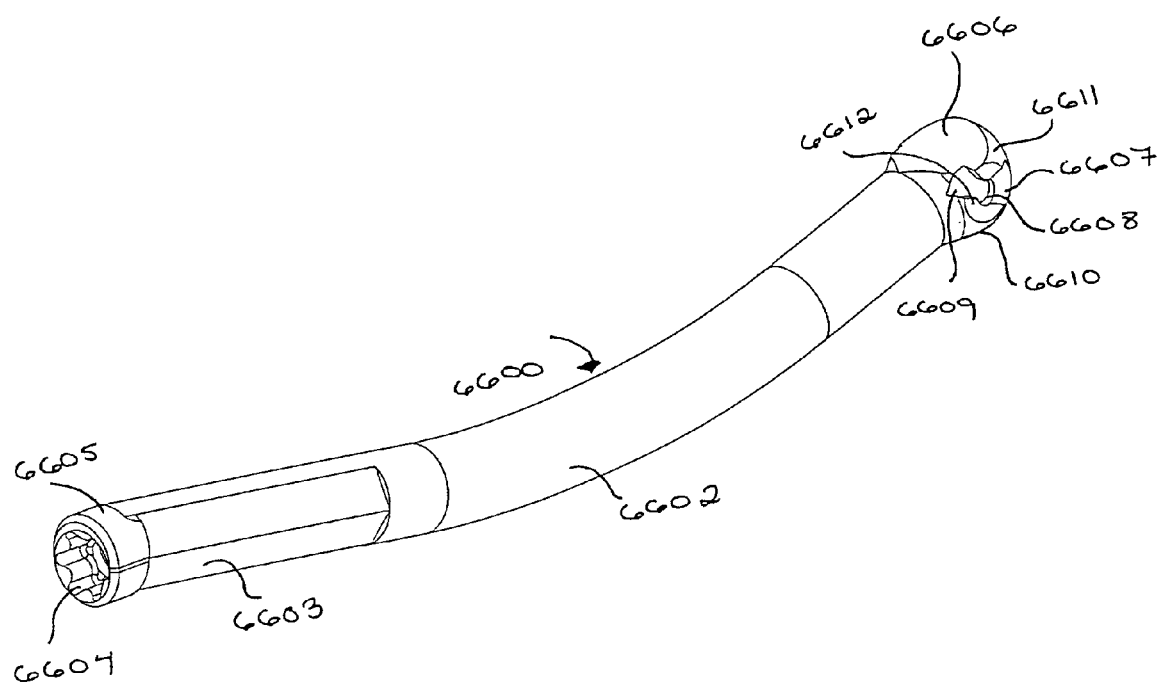
FIG. 67a is a perspective view of an embodiment of a rod intended to span three pedicles according to the present invention.

FIGS. 67*a* and *b* show a rod for use in a multi-level procedure where more than two pedicle screws are used. Rod 6600 has an arched or bent portion, 6602, so that rod 6600 has an arc that best fits the spine curvature. Slide ring surface 6603 and distal end driving surface 6604 are the same as discussed for rod 700 (FIG. 7) except that driving surface 6604 is at an angle because portion 6605 is angled with respect to slider 6603.

At the proximal end of rod 6600 there is top surface 6606 where the locking cap will engage. Entrance ramp 6607 and spherical portion 6611 performs exactly as it does for rod 700 (FIG. 7). Exit ramp surface 6609 leads away from cylindrical surface (hole) 6608 that is the same as on rod 700. The entire proximal end works exactly as does the proximal end of rod 700, except for the use of surface 6701 to be explained with respect to FIG. 67.

Figure 67B:
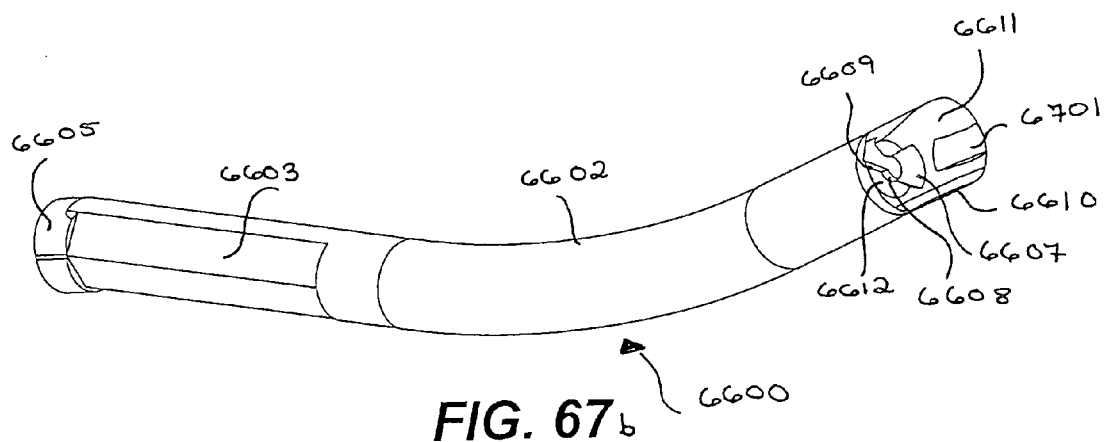
FIG. 67b is a perspective view of the rod of FIG. 67a rotated 180 degrees.

Distal angled portion 6605 is shown in FIG. 67*b* and illustrates bent or arched portion 6602 of rod 6600. Surface 6701 gives more purchase for turning the pedicle screw and works in addition to flats 6612. Flat surface 6610 is on spherical end 6611. Flat surface 6610 will connect with the drive features of the driver just like in the single level.

Figure 68:
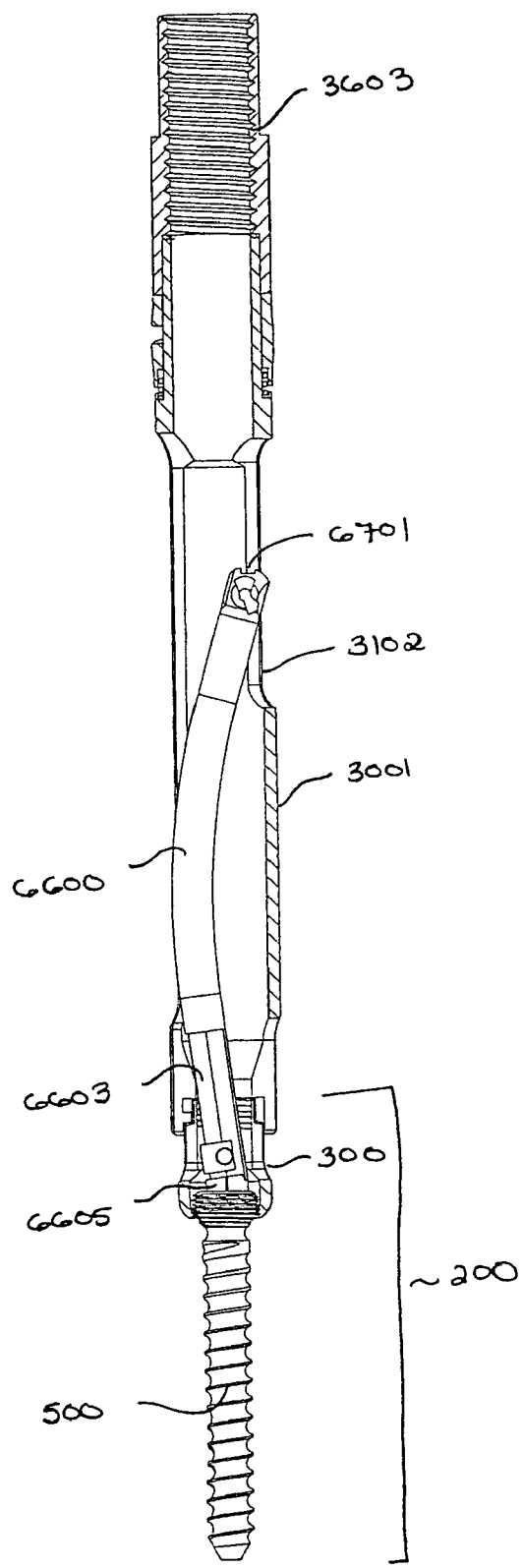
FIG. 68 is a side view of the rod of FIG. 66 mounted to a head and anchor assembly which is mounted to a guide assembly.

FIG. 68 illustrates the relationship of rod 6600 with extension 3001 when rod is mated with anchor 500 and poly-axial head assembly 300. Because rod 6600 is longer than rod 700 to allow it to span three vertebrae, and has additional curvature to match the natural curvature of the spine, an angle of end 6605 is required to allow rod 6600 to fit inside extension 3001 as shown in FIG. 68. This required angle in end 6605 allows the drive mechanism in the distal end to match up with the drive mechanism of anchor 500. Opening 3102 allows the rod transfer tool used in multi-pedicle systems, shown in FIG. 69, to enter extension 3001. The distal end of the rod transfer tool operates in the same manner as the rod transfer tool of FIG. 57, and mates with end 6701 in the same manner as described with reference to the two pedicle system.

Figure 69:
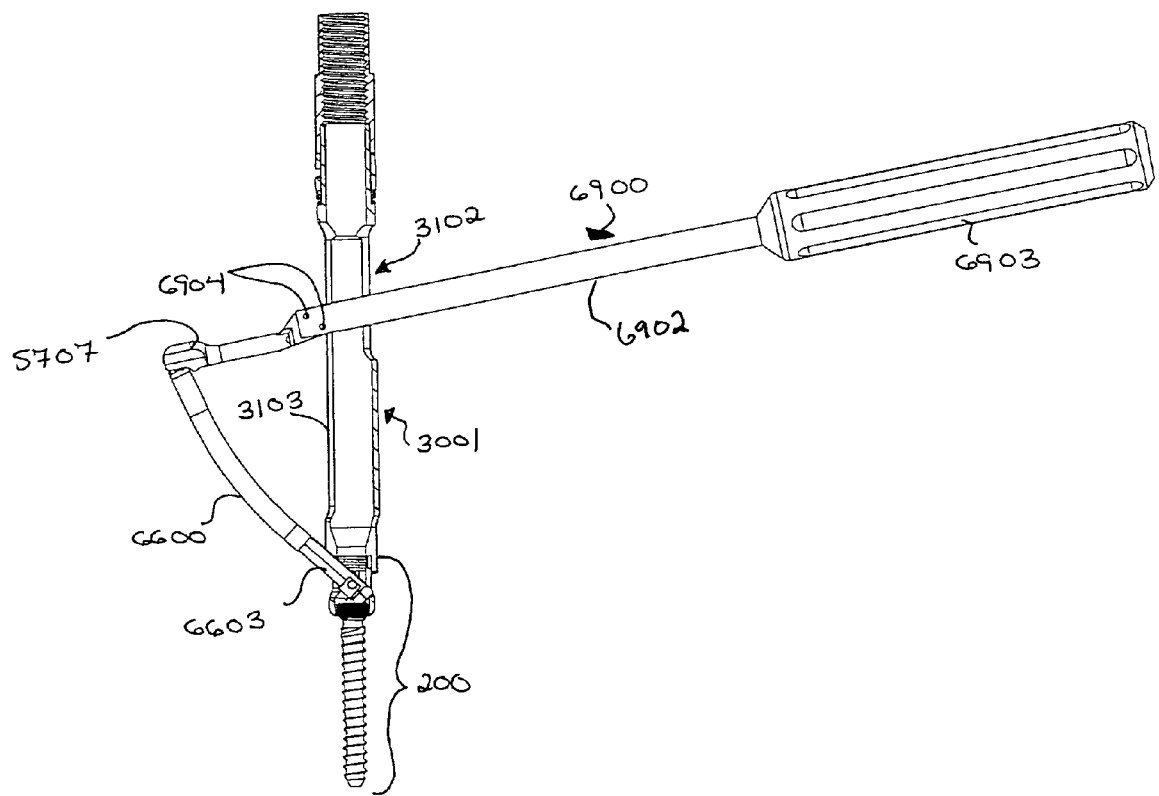
FIG. 69 is a side view of the assembly of FIG. 68 with a tool shown rotating the rod into position.

Rod transfer tool 6900 is shown in FIG. 69. Tool 6900 has shaft 6902 and handle 6903. It has distal arm 5707 connected to shaft 6902 by pivots 6904, which is the same as discussed above with respect to tool 5700 from FIG. 57. Tool 6900 and shaft 6902 are designed to span three or more pedicles through three extensions as shown in FIG. 70.

In operation, distal arm 5707, which is part of the multi-level rod transfer device 6900, is placed through window 3102 and then tines of arm 5707 are snapped onto the proximal end of rod 6600 as discussed above. Then the instrument is lifted to disengage the rod/screw drive mechanism. Next, using handle 6903, the rod is pushed out of extension 3001 via opening 3103.

Figure 70:
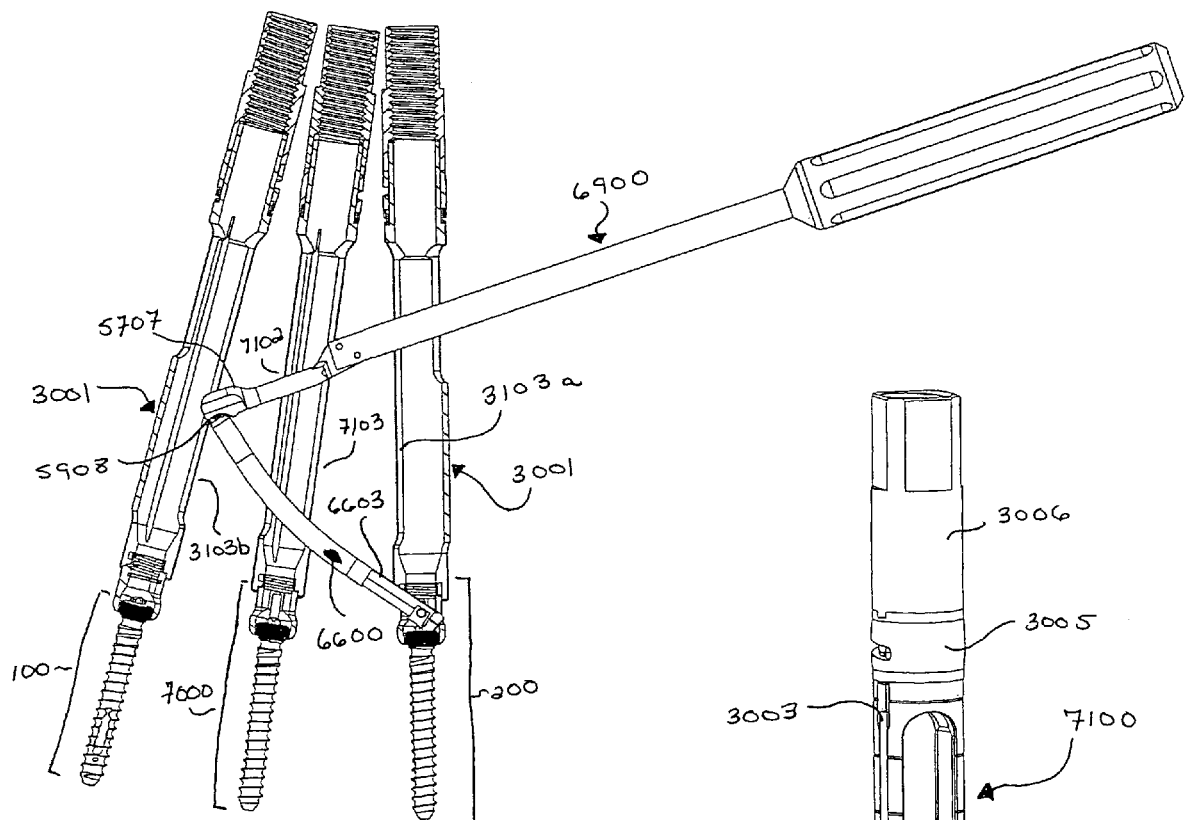
FIG. 70 is a side view of a three pedicle assembly according to the present invention.
Figure 71:
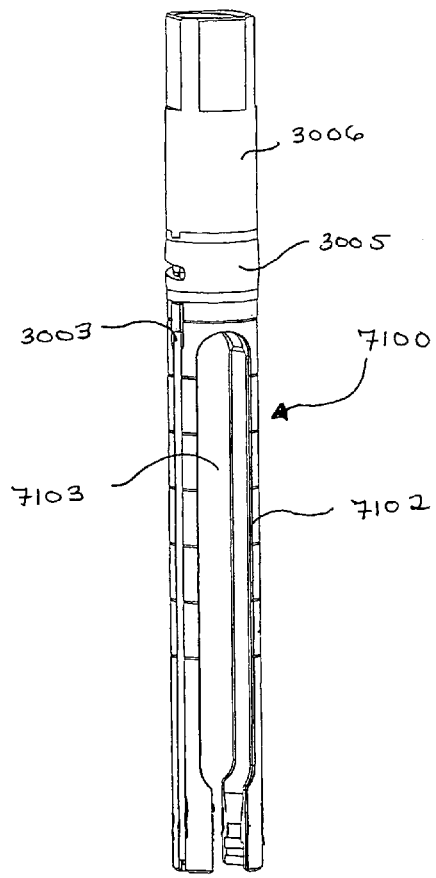
FIG. 71 is a perspective view of an embodiment of a cannula for the three pedicle rod according to the present invention.

FIG. 70 shows, in cut-away, a multi-level setup where assembly 7000 has been added to a center pedicle between assemblies 100 and 200. Assembly 7000 is the same as assembly 100 except that slider 800 is omitted as it is not required.

FIG. 71 shows extension 7100 in greater detail. Extension 7100 is used instead of extension 3001 for the center assembly of the multi-pedicle system. Extension 7100 includes longitudinal cuts 7102 and 7103 on both sides of the body. These cuts allow the rod to pass through extension 7100 so that end 5908 can be positioned in assembly 100. Referring back to FIG. 70, when end 5905 is within extension 3001 of assembly 100, the tines come out of the rod, as discussed above, and tool 6901 can be removed leaving rod 6600 positioned from assembly 200, through assembly 7000 to assembly 100.

Figure 72:
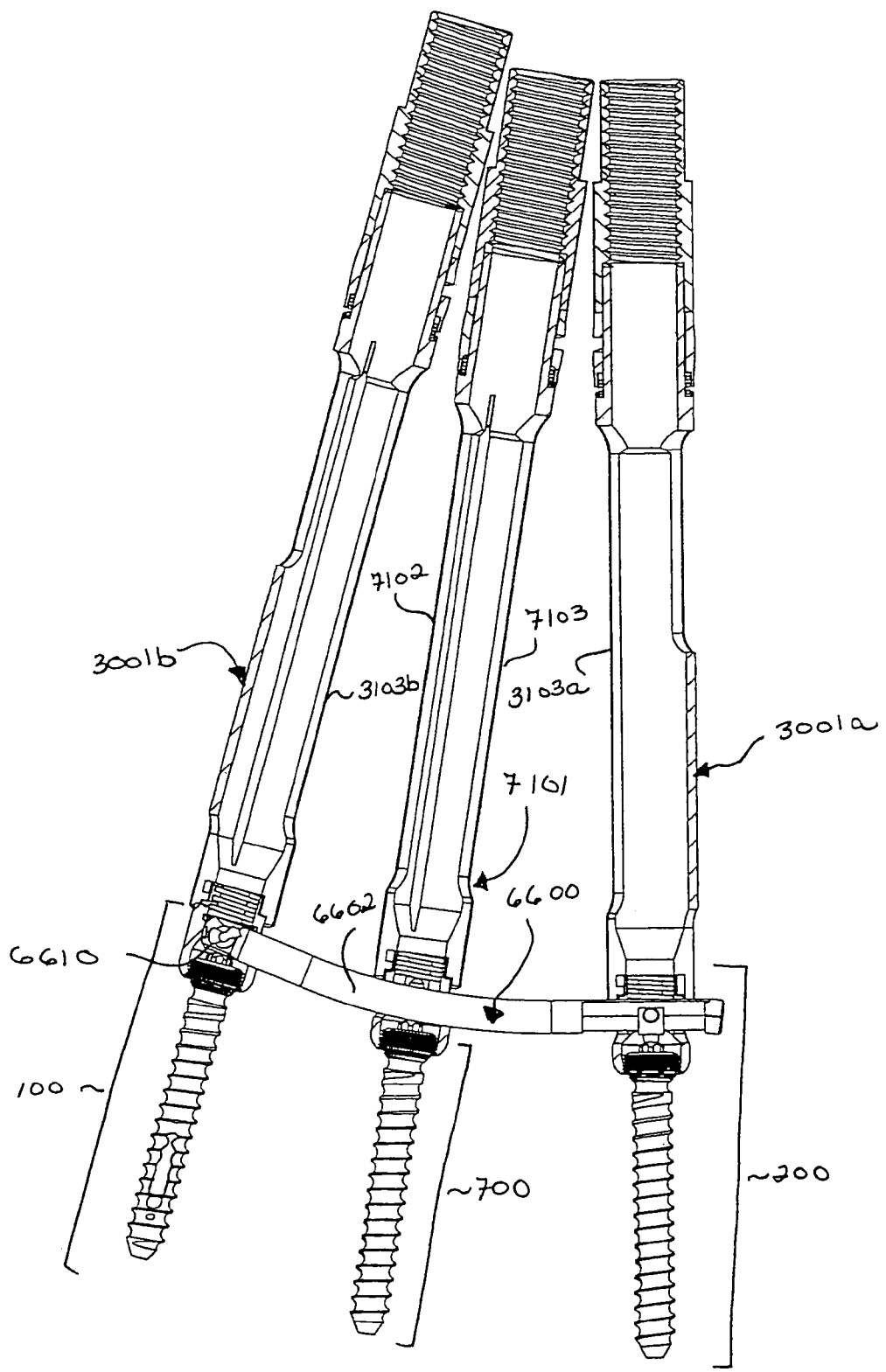
FIG. 72 is a perspective view of the assembly of FIG. 70 with the rod spanning three anchor assemblies.

FIG. 72 shows the entire assembly with extensions. Rod 600 is in its down position ready to accept locking caps, such as caps 1800, FIG. 18, in the manner as discussed above.

FIG. 73 shows multi-level system 7300 locked down. Heads 300 and 1500 are not necessarily in line with its respective anchor 500 because of the axial nature of the connection between the head and the screw. However, once cap 1800 is tightened, the rod, the poly-axial head, and the anchors are held in a rigid, immovable relationship to one another.

The bend in rod 6600 is predefined and can be different for rods of different lengths. By way of example, one could have a 65 millimeter rod, a 75 millimeter rod and an 85 millimeter rod, all having different bends. What is presently done in multi-pedicle systems is not to have a rod with a predefined bend, but rather to set all three pedicle screws and then bend a rod, lay it in and take a fluoroscope shot to see how the rod lines up with the three screws. If it is not correct, it is pulled out, re-bent and again put in position and imaged again. If the rod is over-bent, it is often scrapped. If it is under-bent it is re-bent until it is right. However, in order to allow for use of a pre-bent rod, the screws must be installed in the proper arc. Thus, instead of bending the rod to fit the arc defined by the screws, the screws are installed to fit a pre-defined arc. In operation, assembly 100 is put in first just as with the single level. Then a length is established to the other end pedicles, assembly 200 in FIG. 1, and rod 6600 is moved from the in-line position to the horizontal position. In so doing, a center portion of rod 6600 passes through one or more center extensions (FIG. 70) until end 5908 becomes engaged within extension 3001 of assembly 100.

Figure 74:
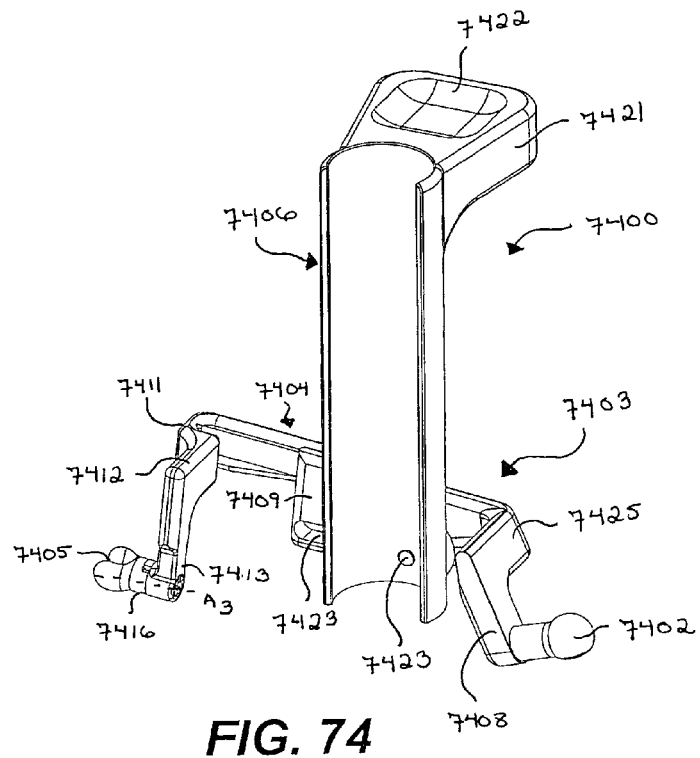
FIG. 74 is a perspective view of an arc defining instrument for use in multi-pedicle assemblies.
Figure 75:
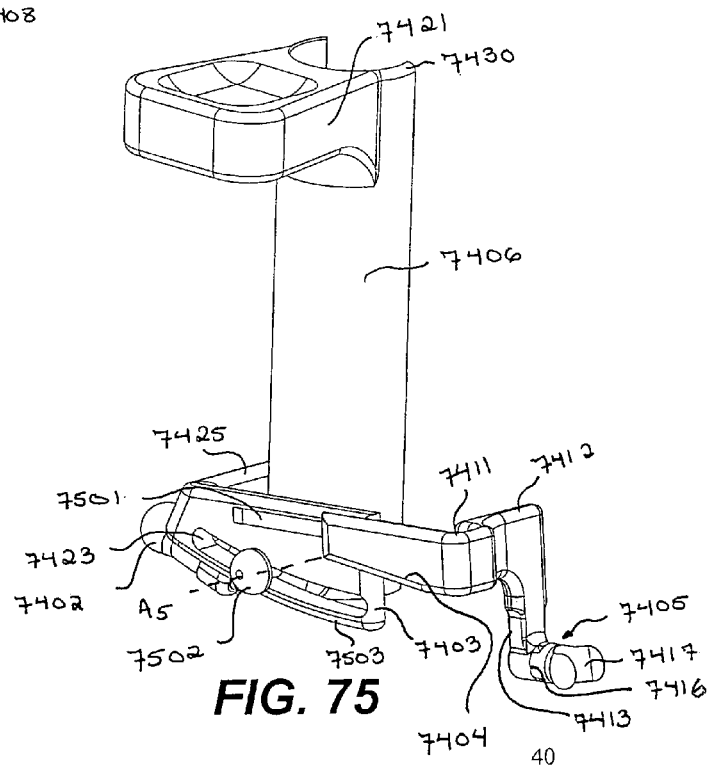
FIG. 75 is a perspective view of the back of the instrument shown in FIG. 74.

FIGS. 74 and 75 illustrate an example of an instrument, such as instrument 7400, that locates the center poly-axial head assembly in a three dimension space according to the arc defined by rod 6600 from FIG. 66 between the end point poly-axial head assemblies. Tool 7400 not only establishes the spacing between the end point assemblies for the center assembly, but also establishes a positional depth setting for the middle poly-axial head assembly. Spherical end 7402 is designed to be held by a poly-axial rod-capturing head, such as the one shown in FIG. 15, and therefore, includes a spherical portion the same diameter as the spherical portion of rod 6600. Thus, end 7402 can slide down extension 3001a to rest in the poly-axial rod-capturing head assembly. End 7405 is intended to be held in a poly-axial rod assembly head such as is described in FIG. 3 and is therefore shaped to fit around rod 6600 by means of u-shaped groove 7417. With the rod in an upright position, end 7405 slides down inside extension 3001b from FIG. 76 to rest on slide ring 800 inside the poly-axial head. End 7402 is held to instrument 7400 by arm 7408 formed with bend 7425 which connects to body 7403. End 7405 is connected to rotational member 7416 which is connected to arm 7413 and is able to rotate in relation to instrument 7400 about axis A3. Arm 7413 is connected to body 7404 by bend 7412 and 7411.

Extension mounting cylinder 7406 is connected to body 7403 by pivot 7423 which allows extension mounting cylinder 7406 to pivot in relation to body 7403. Extension mounting cylinder 7406 forms an arc just greater than 180 degrees and is sized such that its inner diameter is equivalent to the outer diameter of an extension such as extension 7100 of FIG. 71. This allows extension mounting cylinder to be mounted around an extension and hold the extension in place with respect to instrument 7400. Grip 7421 is formed with extension mounting cylinder 7406 and includes indention 7422 which allows grip 7421 to be held securely. Grip 7421 allows for the easy manipulation of instrument 7400 such as the positioning of the instrument over the hole of the center pedicle so that a determination can be made as to the position for the center poly-axial head assembly.

FIG. 75 shows the reverse side of instrument 7400 from FIG. 74. The relationship of bodies 7403 and 7404 can be seen. Bodies 7403 and 7404 can move in relation to one another along slot 7501. This movement is used to set the distance between end 7405 and 7402 so that the instrument can be placed in assemblies 100 and 200 which have already be anchored in their respective pedicles. FIG. 75 also shows slot 7423 in which resides pivot 7423 held in place by shoulder screw 7502. Slot 7423 allows extension mounting cylinder to be moved along the arc defined by slot 7423. The arc defined by slot 7423 corresponds exactly to the arc defined by rod 6600 of FIG. 66 allowing the center poly-axial assembly to be located in three dimensional space in relation to assemblies 100 and 200.

To set the center poly-axial assembly a guide wire is inserted as described with reference to the setting of assemblies 100 and 200. The hole is tapped and the screw is inserted into the hole attached to its head 300 as discussed above. This provides an axis for anchor 500 of assembly 7001 but there is only one plane that rod 6601 rod lays in. Instrument 7400 must position tube 7406 into that axis.

The hole in the center pedicle is tapped and the new anchor assembly is inserted into the pedicle in the manner discussed above for the other anchors. The anchor is positioned in the pedicle to hold it to get a relative positioning for new (middle) extension 7101. Tube 7406 is attached to the outside of extension 7101 and connectors 7404 are positioned on the patients skin surface and ends 7405 and 7402 are placed in their respective extensions. At this point, connectors 7404 can be inserted into the incision between the two extensions and worked down toward the spine. When each end 7405 and 7402 reaches its respective rod within its extension the device will stop moving into the body. Since connectors 7404 are free to adjust to the length and relative heights of each head and since the connector has the same arc as does the rod that will be implanted, top edge 7430 of extension mounting cylinder 7406 will be fixed relative to the desired arc which defines the desired location of the center poly-axial assembly.

Once the top edge of extension mounting cylinder 7406 is fixed with respect to the desired height of the new screw head assembly the screw assembly can be screwed further into the bone. A drive tool as described with reference to the two pedicle assembly, is inserted in side extension 7101 and middle anchor 500 is tightened down. This then brings extension 7101 down until a certain line 7701, shown in FIG. 77, on the extension lines up with the top edge of extension mounting cylinder 7406. This then positions middle head 300 at the proper height so that when the pre-bent rod is connected between the end heads the arc of the rod at the point where it passes through the middle head will pass with the head as discussed above.

While only a three pedicle assembly has been shown, the procedure will work for four or more pedicle assemblies in the same manner.

Figure 76:
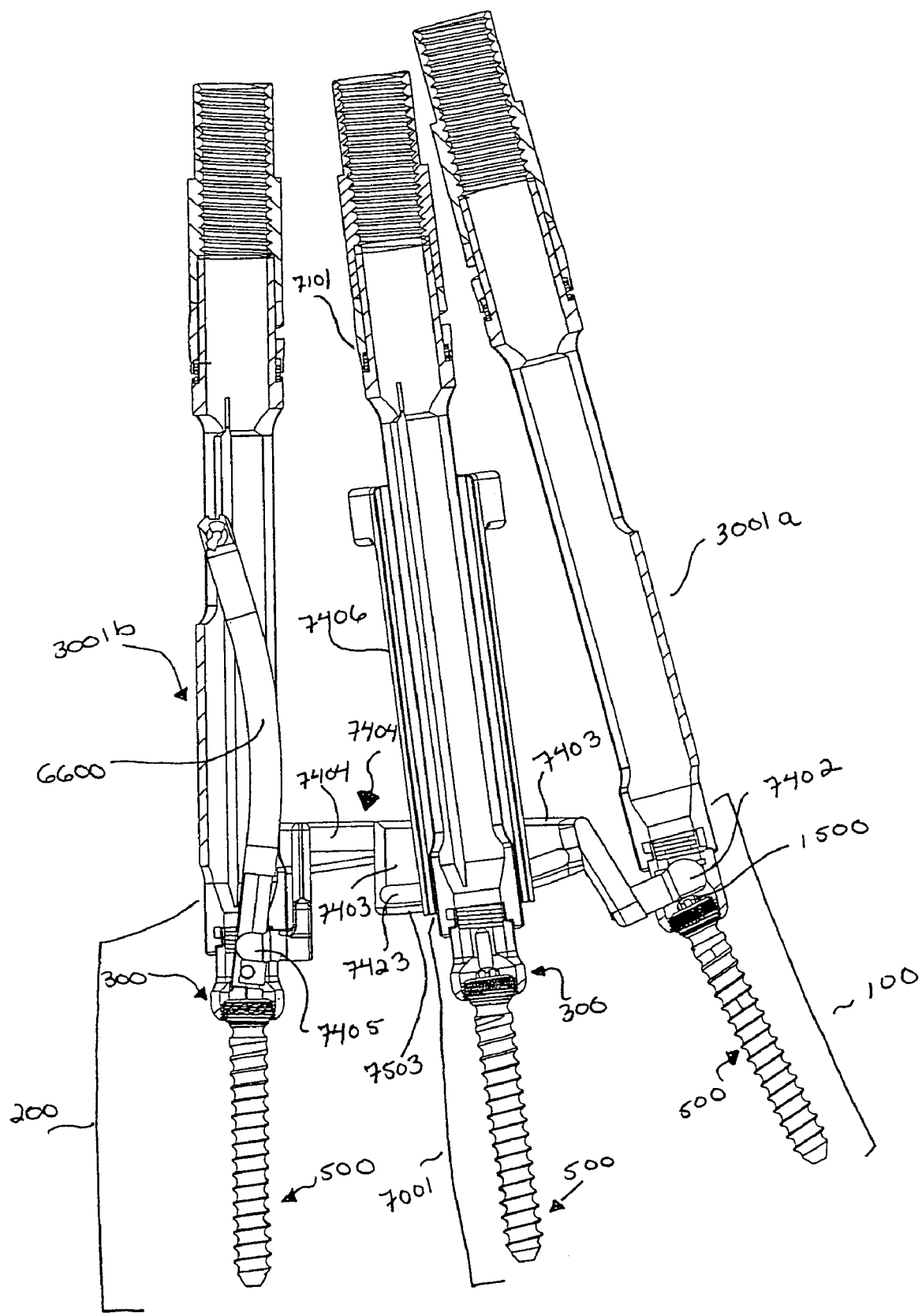
FIG. 76 is front view of the instrument of FIG. 74 with cut away views of extension and poly-axial head assemblies in accordance with the present invention.

FIG. 76 shows instrument 7400 in relation to all three poly-axial head assemblies 100, 200, and 7001, and their associated extensions 3001a, 3001b and 7101.

Figure 77:
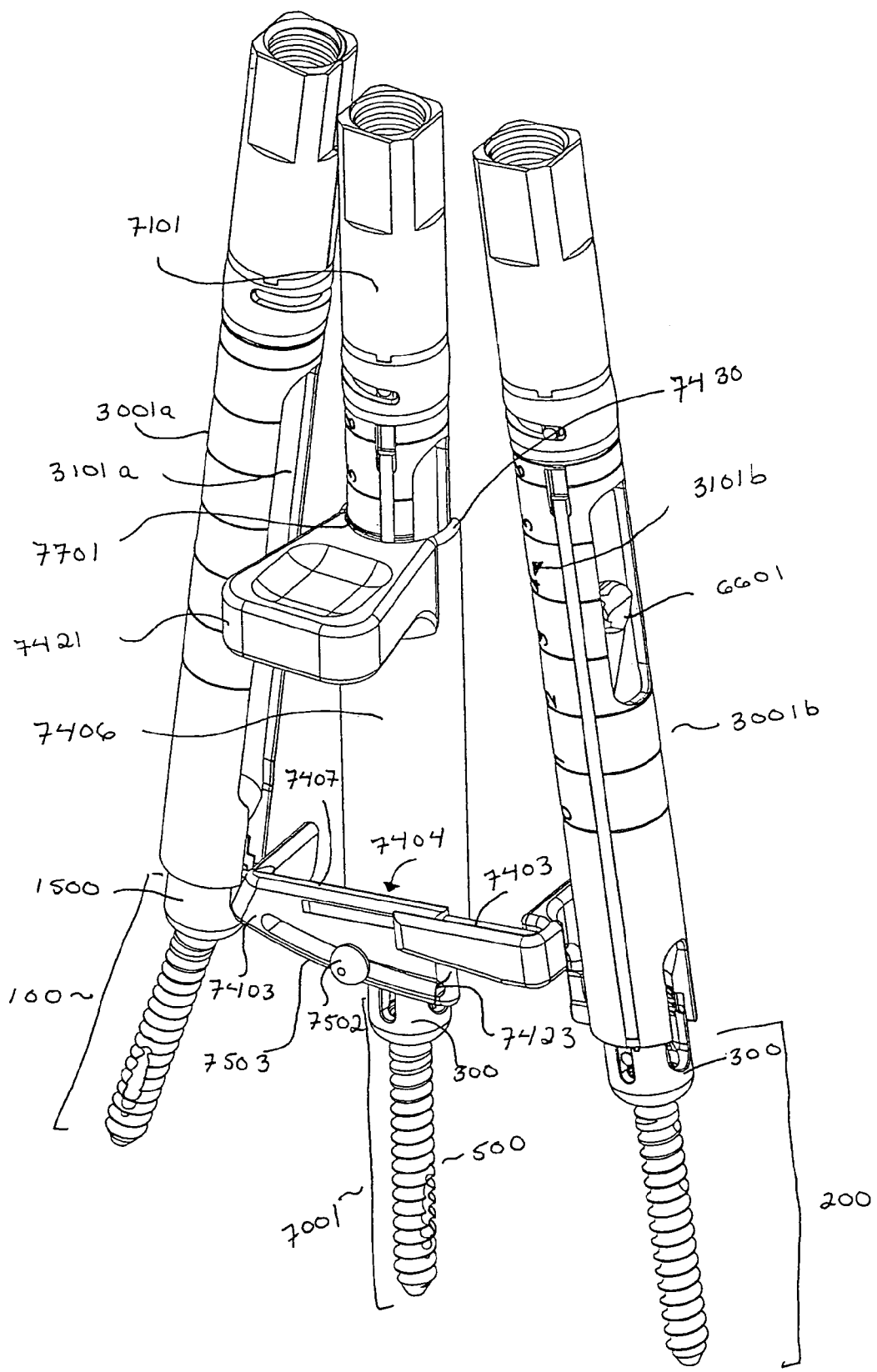
FIG. 77 is a perspective view of the instrument and extension and poly-axial head assemblies shown in FIG. 76.
Figure 7:
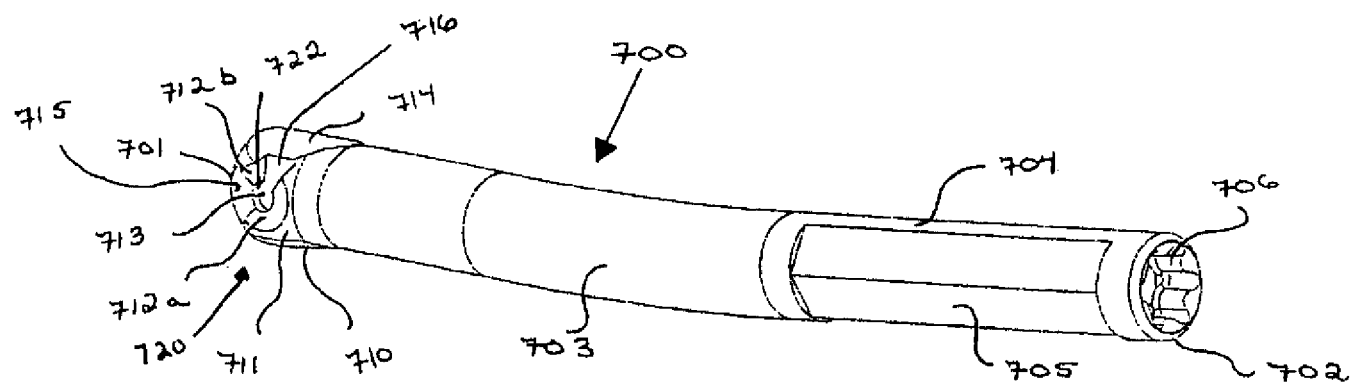
Figure 8:
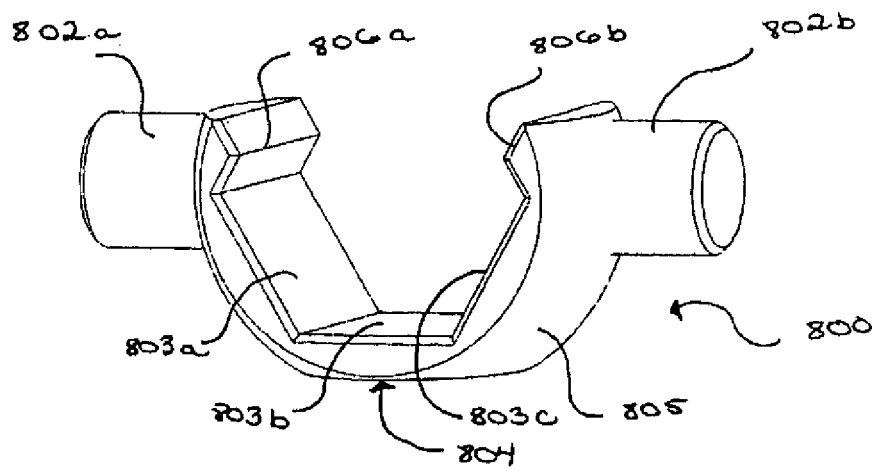
Figure 9:
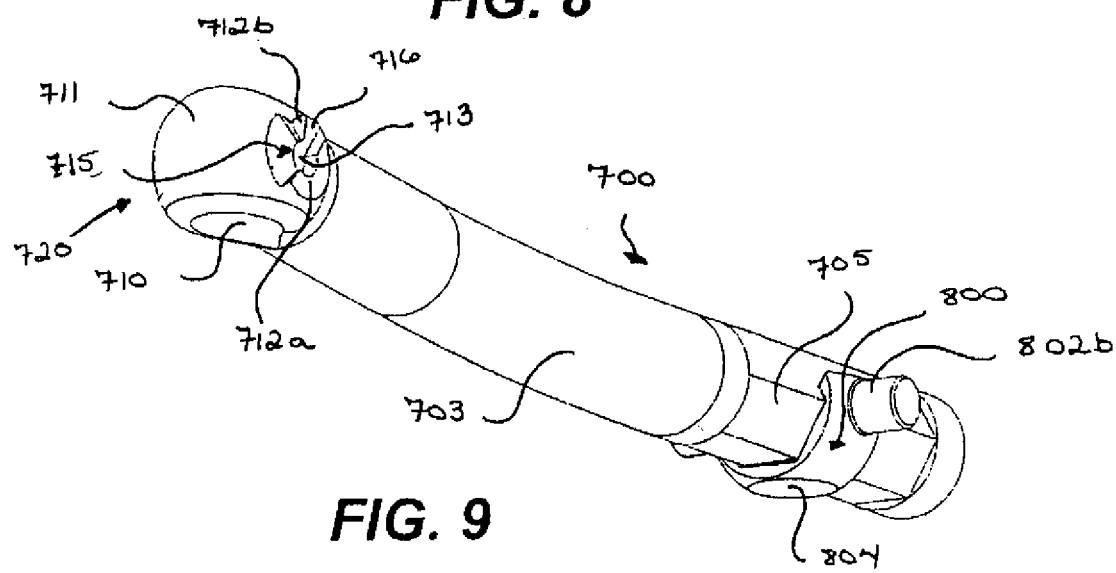
Figure 14:
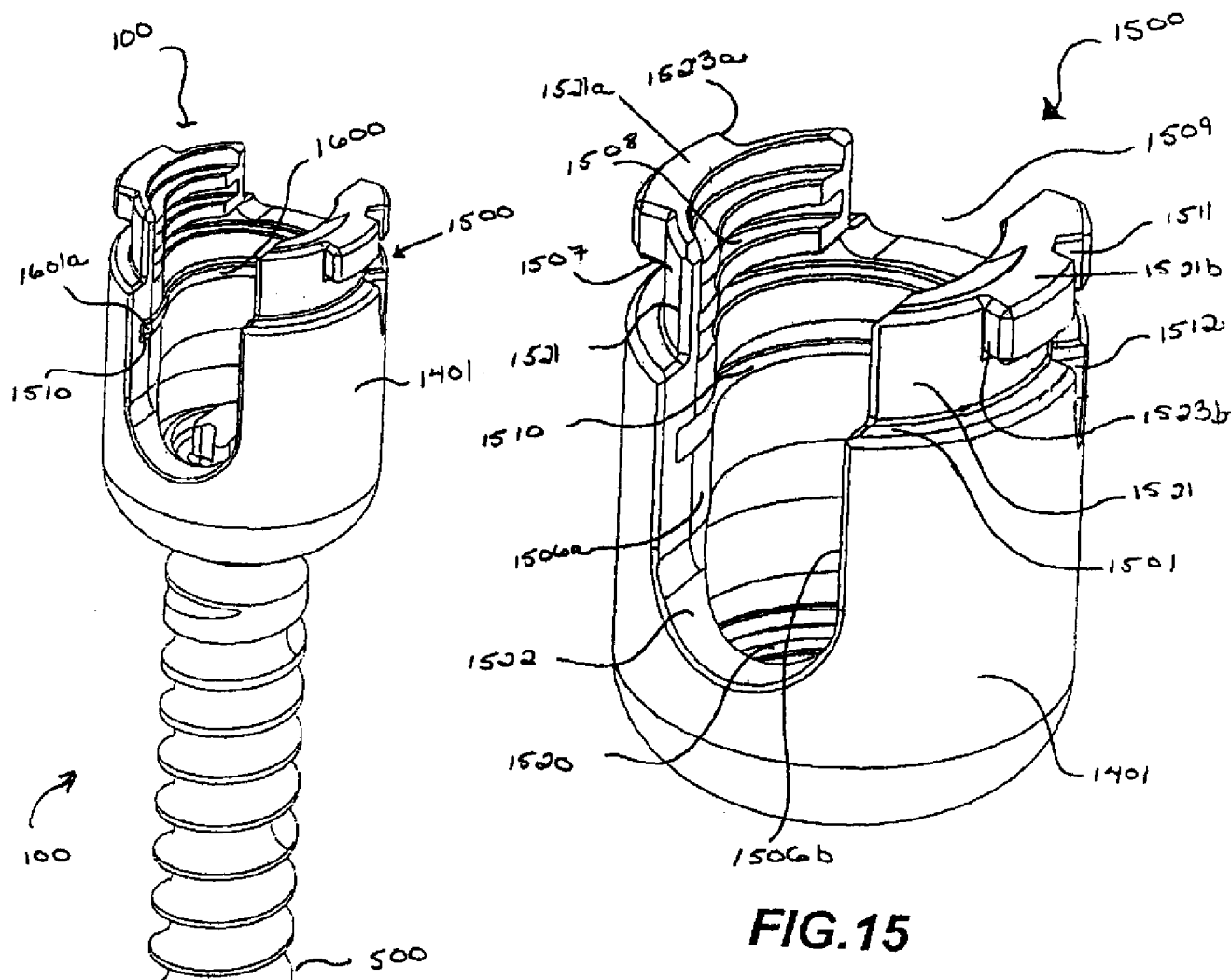
Figure 16:
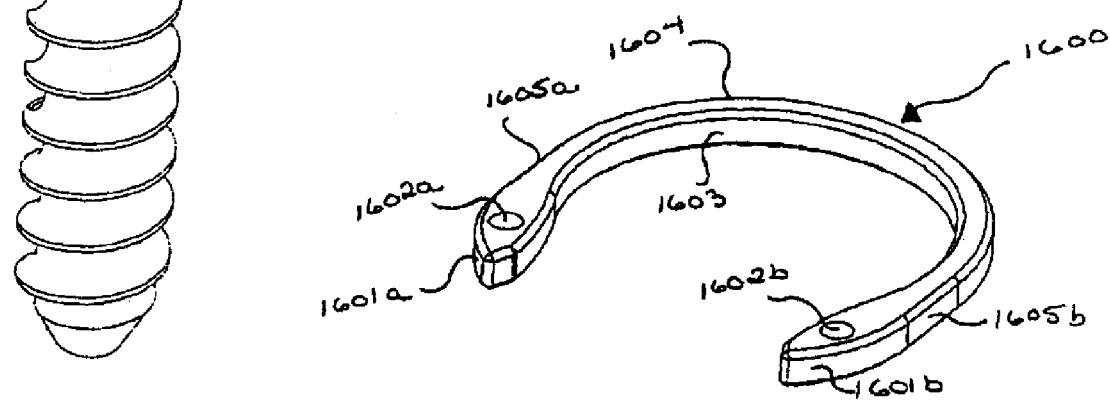

FIG. 77 shows the opposing side of the assembly shown in FIG. 76.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An assembly for use in spinal stabilization procedures, comprising:
    a first bone anchor assembly comprising:
        a first anchor
        a first poly-axial head mated with the anchor such that the anchor is movable in relation to the poly-axial head, the first poly-axial head including a cavity; and
    a second bone anchor assembly comprising:
        a second anchor;
        a second poly-axial head mated with the second anchor such that the second anchor is movable in relation to said second poly-axial head;
        a slide ring rotatably mated in the second poly-axial head;

a connector slidably mated in the slide ring along a distal end, and having a proximal end having an enlarged portion;

wherein the connector is movable from a first position axially inline with the second bone anchor to a second position wherein the enlarged portion of the connector rests in the cavity of the first poly-axial head, and wherein the first position is used to implant the first bone anchor assembly, and the second position used to hold the assembly in a fixed orientation; and a snap ring in the first poly-axial head, the snap ring holding the enlarged portion of the connector in the cavity.

2. The assembly of claim 1, further comprising locking caps inserted into the first and the second poly-axial heads, wherein the locking caps act to lock the elements of the first and second bone anchor assemblies into a fixed orientation.

3. The assembly of claim 2, wherein said locking caps comprise:

a locking ring insertable into said second poly-axial head and operable to hold said slide ring, said first poly-axial head and said first anchor in a fixed orientation; and a compression cap insertable into said locking ring and operable to hold said connector in a fixed orientation with said slide ring.

4. The assembly of claim 1, further comprising an extension removably attached to the first poly-axial head assembly, the extension allowing access to the first bone anchor assembly after implantation.

5. The assembly of claim 4 wherein the extension comprises:

a tubular body having an attachment mechanism for attaching to the first poly-axial head; and a locking mechanism for temporarily locking the extension with the first poly-axial head.

6. The assembly of claim 5 wherein the locking mechanism is a twist ring and a slider attached to the tubular body, the twist ring twistable to cause the slider to move between a first and second position, the first position temporarily locking the extension to the first poly-axial head, the second position allowing the extension to be disengaged from the first poly-axial head.

7. The assembly of claim 1 wherein the first anchor includes an off-axis guide from a tip of the first anchor out a side of the first anchor, the off-axis guide allowing the first anchor to be guided down a guide wire.

8. The assembly of claim 1 wherein the connector includes a drive mechanism mated to a drive mechanism of the second anchor when the connector is in the first position, the connector operable in the first position to transfer torque from a tool to the second anchor.

9. The assembly of claim 1 wherein the connector includes an engagement mechanism in the enlarged portion, the engagement mechanism for engaging with a connector transfer tool.

10. An assembly for use in spinal stabilization procedures, comprising:

a first bone anchor assembly comprising:
a first anchor
a first poly-axial head mated with the anchor such that the anchor is movable in relation to the poly-axial head, the first poly-axial head including a cavity; and a second bone anchor assembly comprising:
a second anchor;
a second poly-axial head mated with the second anchor such that the second anchor is movable in relation to said second poly-axial head;
a slide ring rotatably mated in the second poly-axial head;
a connector slidably mated in the slide ring along a distal end, and having a proximal end having an enlarged portion;
wherein the connector is movable from a first position axially inline with the second bone anchor to a second position wherein the enlarged portion of the connector rests in the cavity of the first poly-axial head, and wherein the first position is used to implant the first bone anchor assembly, and the second position used to hold the assembly in a fixed orientation; and
wherein the connector includes a drive mechanism mated to a drive mechanism of the second anchor when the connector is in the first position, the connector operable in the first position to transfer torque from a tool to the second anchor.

11. The assembly of claim 10, further comprising a snap ring in the first poly-axial head, the snap ring holding the enlarged portion of the connector in the cavity.

12. The assembly of claim 10, further comprising locking caps inserted into the first and the second poly-axial heads, wherein the locking caps act to lock the elements of the first and second bone anchor assemblies into a fixed orientation.

13. The assembly of claim 12, wherein said locking caps comprise:

a locking ring insertable into said second poly-axial head and operable to hold said slide ring, said first poly-axial head and said first anchor in a fixed orientation; and a compression cap insertable into said locking ring and operable to hold said connector in a fixed orientation with said slide ring.

14. The assembly of claim 10, further comprising an extension removably attached to the first poly-axial head assembly, the extension allowing access to the first bone anchor assembly after implantation.

15. The assembly of claim 14, wherein the extension comprises:

a tubular body having an attachment mechanism for attaching to the first poly-axial head; and a locking mechanism for temporarily locking the extension with the first poly-axial head.

16. The assembly of claim 15, wherein the locking mechanism is a twist ring and a slider attached to the tubular body, the twist ring twistable to cause the slider to move between a first and second position, the first position temporarily locking the extension to the first poly-axial head, the second position allowing the extension to be disengaged from the first poly-axial head.

17. The assembly of claim 10, wherein the first anchor includes an off-axis guide from a tip of the first anchor out a side of the first anchor, the off-axis guide allowing the first anchor to be guided down a guide wire.

18. The assembly of claim 10, wherein the connector includes an engagement mechanism in the enlarged portion, the engagement mechfanism for engaging with a connector transfer tool.

* * * * *

UNITED STATES PATENT AND TRADEMARK OFFICE
CERTIFICATE OF CORRECTION

PATENT NO. : 7,618,442 B2  
APPLICATION NO. : 10/990272  
DATED : November 17, 2009  
INVENTOR(S) : Spitler et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,618,442 B2
APPLICATION NO. : 10/990272
DATED : November 17, 2009
INVENTOR(S) : Spitler et al.

It is certified that error appears in the above-identified patent and that said Letters Patent is hereby corrected as shown below:

On title page 3, replace "EP 1604618 A1 11/2005" with --EP 1604618 A1 12/2005--

Replace drawing sheet 4 containing Figures 7-9 with the attached replacement drawing sheet containing Figures 7-9.

Replace drawing sheet 9 containing Figures 14-16 with the attached replacement drawing sheet containing Figures 14-16.

Replace drawing sheet 20 containing Figures 39-41 with the attached replacement drawing sheet containing Figures 39-41.

Replace drawing sheet 21 containing Figures 42-45 with the attached replacement drawing sheet containing Figures 42-45.

Replace drawing sheet 31 containing Figures 59 and 60 with the attached replacement drawing sheet containing Figures 59 and 60.

Replace drawing sheet 32 containing Figures 61-63 with the attached replacement drawing sheet containing Figures 61-63.

Replace drawing sheet 33 containing Figures 64-65b with the attached replacement drawing sheet containing Figures 64-65b.

Replace drawing sheet 38 containing Figures 70 and 71 with the attached replacement drawing sheet containing Figures 70 and 71.

Replace drawing sheet 41 containing Figures 74 and 75 with the attached replacement drawing sheet containing Figures 74 and 75.

Signed and Sealed this
Tenth Day of July, 2012

David J. Kappos
*Director of the United States Patent and Trademark Office*

CERTIFICATE OF CORRECTION (continued)
U.S. Pat. No. 7,618,442 B2

Replace drawing sheet 42 containing Figure 76 with the attached replacement drawing sheet containing Figure 76.

Replace drawing sheet 43 containing Figure 77 with the attached replacement drawing sheet containing Figure 77.

Column 2, Line 24: replace "approach" with --approaches--
Column 2, Line 33: replace "manipulation" with --manipulating--
Column 4, Line 50: replace "cross-section" with --cross-sectional--
Column 5, Line 5: replace "cross-section" with --cross-sectional--
Column 5, Line 7: insert --a-- after "of"
Column 5, Line 28: replace "prospective" with --perspective--
Column 6, Line 20: insert --of-- after "view"
Column 6, Line 56: insert --a-- after "is"
Column 6, Line 65: replace "and" with --an--
Column 7, Line 41: insert --to-- after "used"
Column 7, Line 43: replace "determining" with --determines--
Column 8, Line 6: replace "65c" with --66a--
Column 8, Line 17: replace "connection" with --connecting--
Column 8, Line 18: replace "my" with --may--
Column 8, Line 52: replace "and" with --an--
Column 9, Line 2: replace "rod capturing" with --rod-capturing--
Column 9, Line 5: replace "is" with --it--
Column 9, Line 44: replace "poly axial" with --poly-axial--
Column 9, Line 58: replace "then" with --than--
Column 9, Line 67: replace "treads" with --threads--
Column 10, Line 39: replace "an" with --can--
Column 12, Line 18: replace "22a" with --22a.--
Column 12, Line 23: insert --to-- after "reference"
Column 13, Line 4: replace "be" with --been--
Column 13, Line 12: replace "1521a and 1521b form" with --1521 forms--
Column 13, Line 56: replace "cup" with --cap--
Column 13, Line 67: replace "1800" with --1600--
Column 15, Line 19: insert --be-- after "to"
Column 15, Lines 44-45: insert --or dilator-- after "cannula"
Column 15, Line 53: replace "key way" with --key-way--
Column 15, Line 54: replace "cannula" with --key-way hole--
Column 15, Line 54: replace "key way" with --key-way--
Column 15, Line 55: replace "2505" with --2501--
Column 15, Line 55: replace "2607" with --2601--
Column 15, Line 58: replace "therein" with --therein.--
Column 15, Line 64: delete "," after "needle"
Column 16, Line 12: replace "point" with --point.--
Column 16, Line 32: replace "awl" with --tap--
Column 16, Line 60: replace "shows" with --show--

Column 16, Line 65: replace "is" with --in--
Column 17, Line 14: replace "vise" with --vice--
Column 17, Line 37: replace "tube" with --extension assembly--
Column 17, Line 39: replace "d2" with --d1--
Column 18, Line 4: replace "prevents" with --prevent--
Column 18, Line 11: replace "3501" with --3007--
Column 18, Line 23: replace "36" with --30--
Column 18, Line 51: replace "128a" with --328a--
Column 18, Line 52: replace "mated part" with --mated, portion--
Column 18, Line 53: replace "side" with --side,--
Column 18, Line 55: replace "330a" with --330b--
Column 18, Line 55: replace "330b" with --330a--
Column 18, Line 62: replace "330b" with --330a--
Column 18, Line 62: replace "330a" with --330b--
Column 18, Line 66: replace "of" with --to--
Column 19, Line 3: replace "330b" with --330a--
Column 19, Line 3: replace "330a" with --330b--
Column 19, Line 9: replace "3402 and 3302" with --3302 and 3402--
Column 19, Line 14: replace "3302" with --3402--
Column 19, Line 15: replace "3402" with --3302--
Column 20, Line 5: replace "4909" with --4803--
Column 20, Line 28: replace "480" with --4800--
Column 20, Line 43: replace "48" with --4800 in--
Column 20, Line 46: insert --Male screw threads 4910 engage with female screw threads 5305 of lower portion 5203.-- after "assembly 100."
Column 21, Line 43: replace "5910" with --5907--
Column 21, Line 56: insert --or ramp-- after "opening"
Column 22, Line 31: replace "5905a and has" with --5905a and b have--
Column 22, Line 51: replace "be" with --b--
Column 23, Line 31: replace "which" with --while--
Column 23, Line 56: replace "67" with --68--
Column 24, Line 28: replace "7100" with --7101--
Column 24, Line 29: replace "7100" with --7101--
Column 24, Line 30: replace "7100" with --7101--
Column 24, Line 32: replace "7100" with --7101--
Column 24, Line 34: replace "5905" with --5908--
Column 24, Line 36: replace "6901" with --6900--
Column 24, Line 40: replace "600" with --6600--
Column 25, Line 6: replace "66" with --67a--
Column 25, Line 28: replace "7423" with --7423a--
Column 25, Line 29: insert --about axis $A_5$-- after "7403"
Column 25, Line 32: replace "7100" with --7101--
Column 25, Line 48: replace "be" with --been--
Column 25, Line 49: replace "pivot 7423" with --pivot 7423a--

CERTIFICATE OF CORRECTION (continued)
U.S. Pat. No. 7,618,442 B2

Column 25, Line 53: replace "66" with --67a--
Column 25, Line 61: replace "rod 6601 rod" with --the rod 6600--
Column 25, Line 62: replace "tube" with --extension mounting cylinder--
Column 25, Line 67: replace "Tube" with --Extension mounting cylinder--
Column 26, Line 1: replace "connectors 7404 are" with --body 7404 is--
Column 26, Line 3: replace "connectors" with --body--
Column 26, Line 7: replace "connectors 7404 are" with --body 7404 is--
Column 26, Line 17: replace "in side" with --inside--
Column 26, Line 57: insert --;-- after "first anchor"
Column 27, Line 60: insert --;-- after "first anchor"
Column 28, Line 61: replace "mechfanism" with --mechanism--

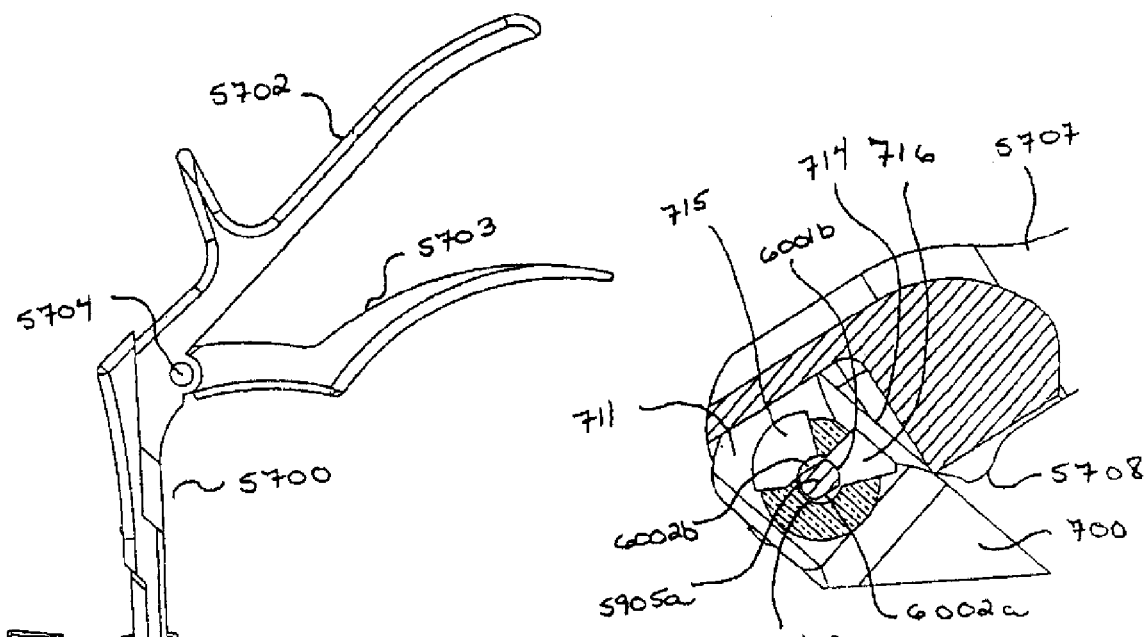
FIG. 65b
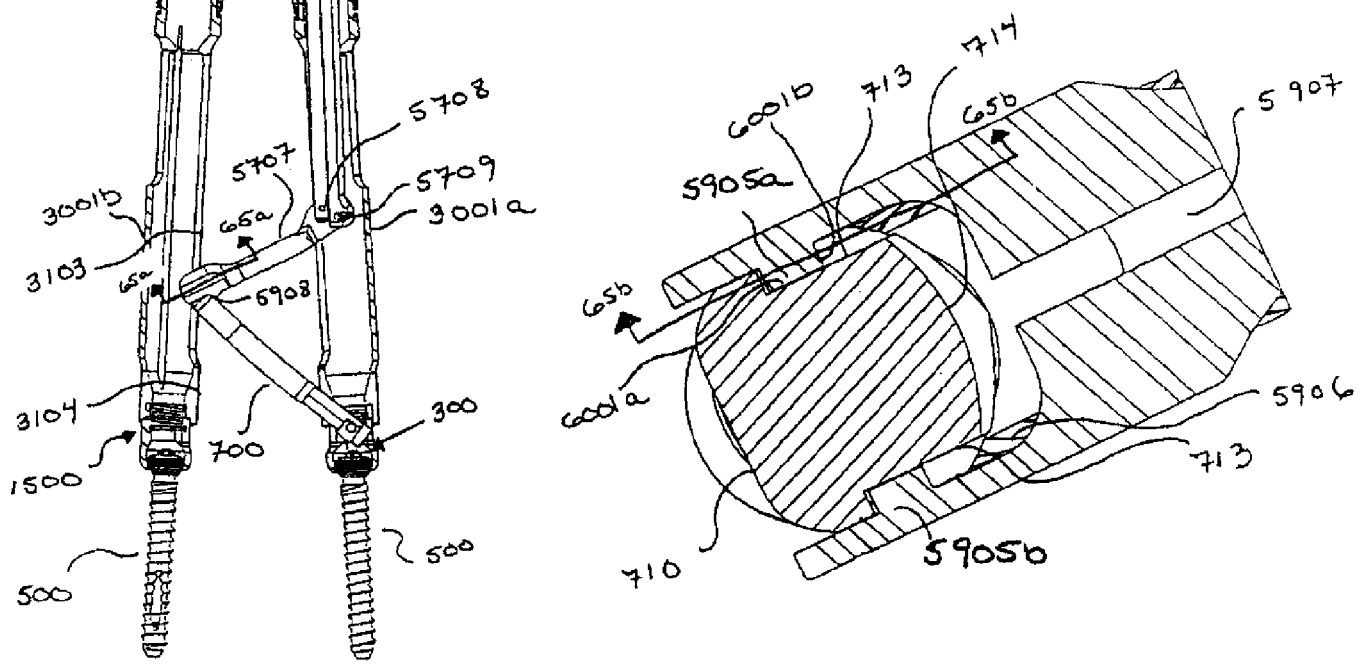
FIG. 65a
FIG. 64